US011267873B2

(12) United States Patent
Sasisekharan et al.

(10) Patent No.: US 11,267,873 B2
(45) Date of Patent: *Mar. 8, 2022

(54) ANTIBODIES THAT BIND ZIKA VIRUS ENVELOPE PROTEIN AND USES THEREOF

(71) Applicants: Massachusetts Institute of Technology, Cambridge, MA (US); National University of Singapore, Singapore (SG)

(72) Inventors: Ram Sasisekharan, Lexington, MA (US); Kannan Tharakaraman, Woburn, MA (US); Kuan Rong Chan, Singapore (SG); Satoru Watanabe, Singapore (SG); Subhash G. Vasudevan, Singapore (SG); Eng Eong Ooi, Singapore (SG)

(73) Assignees: Massachusetts Institute of Technology, Cambridge, MA (US); National University of Singapore, Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 16/341,845

(22) PCT Filed: Oct. 13, 2017

(86) PCT No.: PCT/US2017/056596
§ 371 (c)(1),
(2) Date: Apr. 12, 2019

(87) PCT Pub. No.: WO2018/071822
PCT Pub. Date: Apr. 19, 2018

(65) Prior Publication Data
US 2019/0315838 A1    Oct. 17, 2019

Related U.S. Application Data

(60) Provisional application No. 62/408,020, filed on Oct. 13, 2016.

(51) Int. Cl.
| | |
|---|---|
| *C07K 16/10* | (2006.01) |
| *C07K 14/18* | (2006.01) |
| *A61K 39/42* | (2006.01) |
| *A61K 39/395* | (2006.01) |
| *A61K 39/12* | (2006.01) |
| *A61P 31/12* | (2006.01) |
| *A61P 31/14* | (2006.01) |
| *A61K 39/00* | (2006.01) |
| *C12N 15/63* | (2006.01) |

(52) U.S. Cl.
CPC .......... *C07K 16/1081* (2013.01); *A61K 39/42* (2013.01); *C07K 14/1825* (2013.01); *A61K 39/12* (2013.01); *A61K 39/395* (2013.01); *A61K 2039/505* (2013.01); *A61P 31/12* (2018.01); *A61P 31/14* (2018.01); *C07K 16/10* (2013.01); *C07K 2317/21* (2013.01); *C07K 2317/33* (2013.01); *C07K 2317/565* (2013.01); *C07K 2317/76* (2013.01); *C07K 2317/92* (2013.01); *C12N 15/63* (2013.01); *C12N 2770/24111* (2013.01); *C12N 2770/24122* (2013.01); *Y02A 50/30* (2018.01)

(58) Field of Classification Search
CPC ...... C07K 16/1081; C12N 2770/24111; C12N 2770/24122
See application file for complete search history.

(56) References Cited

U.S. PATENT DOCUMENTS

| | | | |
|---|---|---|---|
| 10,829,545 B2* | 11/2020 | Sasisekharan | ....... A61K 39/395 |
| 2014/0056913 A1 | 2/2014 | Sasisekharan et al. | |
| 2018/0105583 A1 | 4/2018 | Sasisekharan et al. | |
| 2021/0009663 A1 | 1/2021 | Sasisekharan et al. | |

FOREIGN PATENT DOCUMENTS

| | | |
|---|---|---|
| WO | 2014/064943 A1 | 5/2014 |
| WO | 2016/012800 A1 | 1/2016 |
| WO | 2018010789 A1 | 1/2018 |
| WO | 2018/071822 A2 | 4/2018 |

OTHER PUBLICATIONS

Sela-Culang, I., et al., Oct. 2013, The structural basis of antibody-antigen recognition, Front. Immunol. 4, article 302, pp. 1-13.*
Nikoloudis, D., et al., Mar. 2014, A complete, multi-level conformational clustering of antibody complementarity-determining regions, PeerJ 2:e456, pp. 1-40.*
Xiang, J., et al., 1999, Light-chain framework region residue Tyr71 of chimeric B72.3 antibody plays an important role in influencing the TAG72 antigen binding, Prot. Engineer. 12(5):417-421.*
Liu, Z., et al., 1999, Fine mapping of the antigen-antibody interaction of scFv215, a recombinant antibody inhibiting RNA polymerase II from *Drosophila melanogaster*, J. Mol. Recog. 12:103-111.*
Winkler, K., et al., 2000, Changing the antigen binding specificity by single point mutations of an anti-p24 (HIV-1) antibody, J. Immunol. 165:4505-4514.*
U.S. Appl. No. 15/783,655, filed Oct. 13, 2017, Ram Sasisekharan.
U.S. Appl. No. 15/783,655, dated Jan. 3, 2020, J. Parkin.
U.S. Appl. No. 15/783,655, dated Apr. 2, 2019, J. Parkin.
U.S. Appl. No. 15/783,655, dated Oct. 31, 2018, J. Parkin.
Barba-Spaeth, G. et al., "Structural basis of potent Zika-dengue virus antibody cross-neutralization," Nature, vol. 536:48-53 (2016).

(Continued)

*Primary Examiner* — Jeffrey S Parkin
(74) *Attorney, Agent, or Firm* — McDonnell Boehnen Hulbert & Berghoff

(57) ABSTRACT

Isolated monoclonal antibodies which bind to Zika virus envelope protein and related antibody-based compositions and molecules are disclosed. Also disclosed are therapeutic and diagnostic methods for using the antibodies.

30 Claims, 13 Drawing Sheets
Specification includes a Sequence Listing.

(56) References Cited

OTHER PUBLICATIONS

Chan, K.R. et al., "Ligation of Fc gamma receptor IIB inhibits antibody-dependent enhancement of dengue virus infection," PNAS, vol. 108(30): 12479-12484 (2011).
Dai, L. et al., "Structures of the Zika Virus Envelope Protein and Its; Complex with a Flavivirus Broadly Protective Antibody," Cell Host & Microbe, vol. 19(5): 696-704 (2016).
Dejnirattisai, W., et al., "A new class of highly potent, broadly neutralizing; antibodies isolated from viremic patients infected with dengue virus," Nature Immunology, vol. 16 (2):170-177 (2014).
Deng, Y-Q., et al., "A Broadly Flavivirus Cross-Neutralizing Monoclonal Antibody that Recognizes a Novel Epitope within the Fusion Loop of E Protein," Plos One, vol. 6(1):e16059,8 pages (2011).
Heinz, F. et al., "The Antigenic Structure of Zika Virus and Its Relation to Other Flaviviruses: Implications for Infection and Immunoprophylaxis," Microbiology and Molecular Biology Reviews, vol. 81 (Issue 1): e00055-16, 27 pages (2017).
International Preliminary Report on Patentability, PCT/US2017/056596, dated Apr. 16, 2019, 9 pages.
International Search Report and Written Opinion, PCT/US2017/056596, dated Apr. 19, 2018, 20 pages.
Kam, Y-W., et al., "Cross-reactive dengue human monoclonal antibody prevents; severe pathologies and death from Zika virus infections," JCI Insight, vol. 2(8):1-10 (2017).
Li, J. et al., "Structure of dengue virus EDIII in complex with Fab 3e31," Full wwPDB X-ray Structure Validation Report, 15 pages (2014).
Li, P. et al., "Development of a Humanized Antibody with High Therapeutic Potential against Dengue Virus Type 2," PLoS Negl Trop Dis., vol. 6(5): e1636(13 pages) (2012) doi:10.1371/journal.pntd.0001636.
Li, X. et al., "Dengue virus envelope domain III immunization elicits predominantly cross-reactive, poorly neutralizing antibodies localized to the AB loop: implications for dengue vaccine design," Journal of General Virology, vol. 94: 2191-2201 (2013).
Lin, H-H et al., "Zika virus structural biology and progress in vaccine development," Biotechnology Advances, vol. 36: 47-53 (2018).
Liu, Z., et al., "Fine mapping of the antigen-antibody interaction of scFv215, a recombinant antibody inhibiting RNA polymerase II from Drosophila melanogaster," J. Mol. Recog., vol. 12:103-111 (1999).
Nikoloudis, D. et al., "A complete, multi-level conformational clustering of antibody complementarity-determining regions," Peer J 2:e456:1-40 (2014).
Pierson, T. et al., "Degrees of maturity: The complex structure and biology of flaviviruses," Curr Opin Virol., vol. 2(2): 168-175(2012).
Robinson, L. et al., "Structure-Guided Design of an Anti-dengue Antibody Directed to a Non-immunodominant Epitope," Cell, Cell Press, US, vol. 162(3):493-504 (2015).
Sapparapu, G. et al., "Neutralizing human antibodies prevent Zika virus replication and fetal disease in mice," Nature, vol. 540(7633): 443-447 (2016).
Sela-Culang, I. et al., "The structural basis of antibody-antigen recognition," Front. Immunol., vol. 4 (Article 302):1-13 (2013).
Soundararajan, V. et al., "Networks link antigenic and receptor-binding sites of influenza hemagglutinin: Mechanistic insight into fitter strain propagation," Scientific Reports, vol. 1(200) 7 pages (2011).
Tharakaraman, K. et al., "Rational Engineering and Characterization of an mAb that Neutralizes Zika Virus by Targeting a Mutationally Constrained Quaternary Epitope," Cell Host & Microbe, vol. 23: 618-627 (2018).
Tharakaraman, K. et al., "Redesign of a cross-reactive antibody to dengue virus with broad-spectrum activity and increased in vivo potency," Proc Natl Acad Sci U S A., vol. 110(17):E1555-1564, (2013) doi:10.1073/pnas.1303645110. Epub Apr. 8, 2013.
Vásquez, M. et al., "Connecting the sequence dots: shedding light on the genesis of antibodies reported to be designed in silico," MABS, vol. 11(5): 803-808 (2019).
Winkler, K., et al., "Changing the antigen binding specificity by single point mutations of an anti-p24 (HIV-1) antibody," J. Immunol., vol. 165:4505-4514 (2000).
Xiang, J. et al., "Light-chain framework region residue Tyr71 of chimeric B72.3 antibody plays an important role in influencing the TAG72 antigen binding," Prot. Engineer., vol. 12(5):417-421 (1999).
Zhang, S. et al., "Neutralization mechanism of a highly potent antibody against Zika virus," Nature Communications, vol. 7 (13679): 7 pages (2016).
Piao, et al., "Affinity-matured recombinant immunotoxin targeting gangliosides 3-isoLM1 and 3,6'-isoLD1 on malignant gliomas," mAbs, 5:5, 748-762, Sep./Oct. 2013.
Brown, M. et al., "Tolerance T single, but not multiple, amino acid replacements in antibody VH CDR 2: a means of minimizing B cell wastage from somatic hypermutation?," The Journal of Immunology, vol. 156 (9):3285-3291(1996).
Crill W D et al., "Localization and characterization of flavivirus envelope glycoprotein cross-reactive epitopes," Journal Of Virology, vol. 78(24): 13975-13986 (2004).
Rudikoff, S. et al., "Single amino acid substitution altering antigen-binding specificity," PNAS, vol. 79(6): 1979-1983 (1982).

\* cited by examiner

>anti-TDRD3:VH
EVQLVESGGGLVQPGGSLRLSCAASGFNLSSSYMHWVRQAPGKGLEWVASISSSYGSTYYADSVKGRFTISA
DTSKNTAYLQMNSLRAEDTAVYYCARTVRGSKKPYFSGWAMDYWGQGTLVTVSS
>VH.1
EVQLLESGGGLVQPGGSLRLSCAASGFSFSTYSMHWVRQAPGKGLEWVSAISGEGDSAYYADSVKGRFTISR
DNSKNTLYLQMNKVRAEDTAVYYCV----GGYSNFYYYTMDAWGQGTMVTVSS
>VH.2
EVQLLESGGGLVQPGGSLRLSCAASGFSFSTYSMHWVRQAPGKGLEWVSAISGEGDSAYYADSVKGRFEISR
DNSKNTLYLQMNKVRAEDTAVYYCV----GGYSNFYYYTMDAWGQGTMVTVSS
>VH.3
EVQLVESGGGLVQPGGSLRLSCSASGFSFSTYSMHWVRQAPGKGLEYVSAITGEGDSAFYADSVKGRFTISR
DNSKNTLYFEMNSLRPEDTAVYYCV----GGYSNFYYYTMDAWGQGTSVTVSS
>VH.4
EVQLLESGGGLVQPGGSLRLSCSASGFTFSTYSMHWVRQAPGKGLEYVSAITGEGDSAFYADSVKGRFTISR
DNSKNTLYFEMNSLRPEDTAVYYCV----GGYSNFYYYTMDAWGQGTSVTVSS
>VH.5
EVQLLESGGGLVQPGGSLRLSCSASGF-FSTYSMHWVRQAPGKGLEYVSAITGEGDSAFYADSVKGRFTISR
DNSKNTLYFEMNSLRPEDTAVYYCV----GGYSNFYYYTMDVWGQGTTVTVSS
>VH.6
QVQLVESGGGLVQPGGSLRLSCSASGFSFSTYSMHWVKQAPGKGLEYVSAITGEGDSAFYADSVKGRFTISR
DNSKNTLYFEMNSLRPEDTAVYYCV----GGYTNFYYYTMDAWGQGTSVTVSS
QVQLVESGGGLVQPGGSLRLSCSASGFSFSTYSMHWVKQAPGKGLEYVSAITGEGDSAFYADSVKGRFTISR
DNSKNTLYFEMNSLRPEDTAVYYCV----GGYTNFYYYTMDAWGQGTSVTVSS

FIG. 1A

```
>anti-TCRD3:VL
DIQMTQSPSSLSASVGDRVTITCRASQSVSSAVAWYQQKPGKAPKLLIYSASSLYSGVPSRFSGSGSRSGTD
FTLTISSLQPEDFATYYCQQHGPFTW--LPTFGQGTKVEIK >VL.1
EIVLTQSPASLSLSPGERATLSCRATQSISTFLAWYQHKPGQAPRLLIYDASTRASGVPARFSGSRSGTD
FTLTISSLEPEDFAVYYCQQR---YNWPPYSFGQGTKVEIK >VL.2
--DIVMTQSPASLSLSPGERATLSCRATQSISTFLAWYQQKPGQAPRLLIYDASTRASGIPARFSGSRSGTD
FTLTITRLEPEDFAVYYCQQR---YNWPPYSFGQGTKLEIK >VL.3
EIVLTQSPASLSLSPGERATLSCRASQSISTFLAWYQHKPGQAPRLLIYDASTRATGVPARFSGSRSGTD
FTLTISTFLEPEDFAVYYCQQR---YNWPPYSFGQGTKVEIK >VL.4
--DIVMTQSPASLSLSPGERATLSCRATQSIVTFLAWYQQKPGQAPRLLIYDASTNASGIPARFSGSRSGTD
FTLTITRLEPEDFAVYYCQQR---YNWPPYSFGQGTKLEIK
```

FIG. 1B

FIG. 5
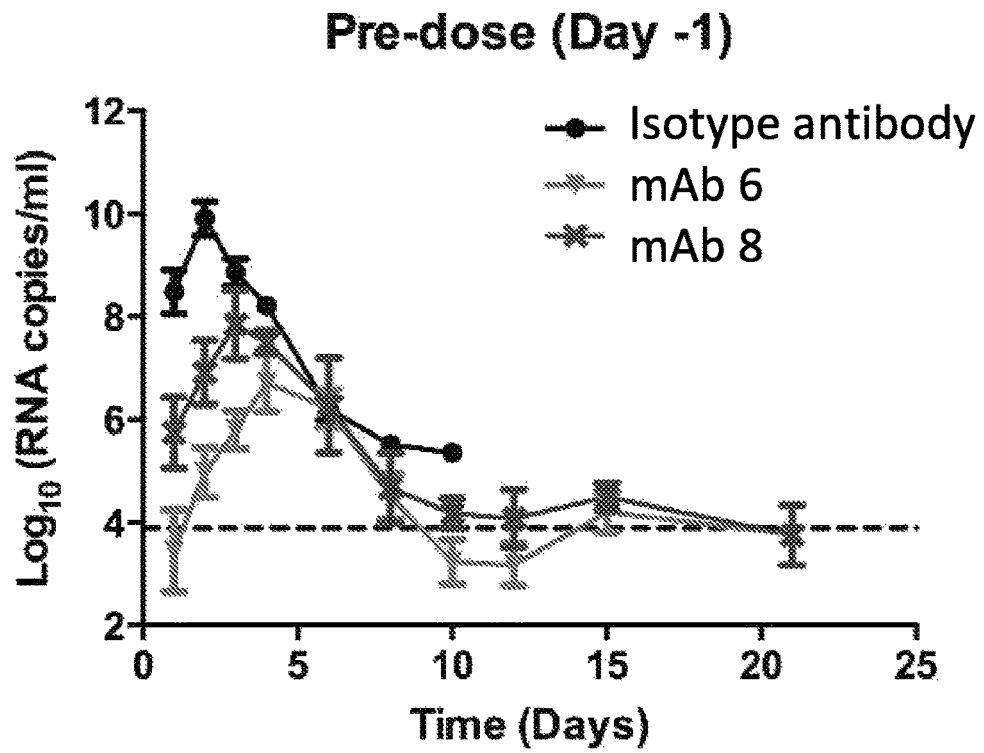
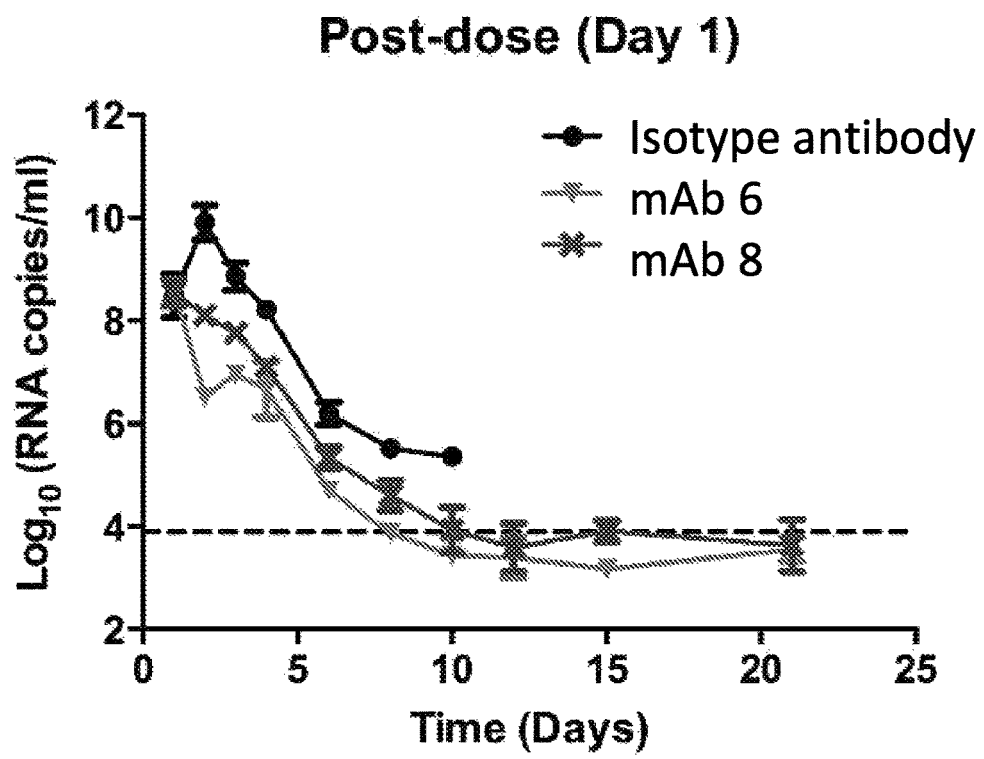

US 11,267,873 B2

ANTIBODIES THAT BIND ZIKA VIRUS ENVELOPE PROTEIN AND USES THEREOF

RELATED APPLICATIONS

This application is a 35 U.S.C. § 371 national stage filing of PCT Application No. PCT/US2017/056596, filed on Oct. 13, 2017, which claims the benefit of the priority date of U.S. Provisional Application No. 62/408,020, which was on filed Oct. 13, 2016. The entire content of each of the above-referenced patent applications is hereby incorporated by reference in its entirety.

REFERENCE TO SEQUENCE LISTING

The instant application contains a Sequence Listing which has been submitted electronically in ASCII format and is hereby incorporated by reference in its entirety. Said ASCII copy, created Apr. 12, 2019, is named "MITN-037US_Sequence-Listing.txt" and is 31533 Kilobytes in size.

BACKGROUND

Zika virus (ZIKV) is a vector-borne arbovirus transmitted by *Aedes aegypti* mosquito. ZIKV infection typically causes mild symptoms, including fever, rash, joint pain, and/or conjunctivitis. However, recent research indicates a link between infection and microcephaly in newborn babies, along with a link between infection and Guillain-barre syndrome in adults. There is an urgent need for effective counter measures as there are no approved vaccines or therapies against ZIKV.

Little is known about the virus, structure, or biology of ZIKV. ZIKV is a member of the virus family Flaviviridae, which includes Dengue (DV), West Nile, Japanese Encephalitis, Tick-born Encephalitis, and Yellow Fever virus. The envelope (E) protein of flavivirus mediates host cell entry and immune evasion. The E protein consists of three structural and functional domains. Antibodies against E protein domain III (E-DIII) have shown prophylactic and therapeutic effects in animal models infected with DV (Robinson, L., et al., *Cell* Vol. 162: 493-504, 2015). Therefore, antibody-based agents against ZIKV envelope protein provide a promising option for combating ZIKV outbreaks in humans.

SUMMARY

The present disclosure pertains to antibodies directed towards Zika virus envelope protein (EP). A systematic analysis of the Zika virus surface guided by the residue interatomic interactions network (or SIN) led to the identification of fusion loop epitope proximal (FLEP) region as being structurally constrained. A structure based computational approach yielded a set of promising scaffolds with potential to interact with the FLEP region. Following this, an anti-TDRD3 (Tudor Domain Containing 3) antibody was investigated due to its ability to interface with the FLEP region. A framework to compute the inter-residue atomic interaction between interacting amino acid pairs of the antigen-antibody interface was utilized, and interactions were rendered in a 2D graph format to analyze the connectivity network. Mutations in the CDRs and/or framework regions that contributed to more favorable contacts, as evaluated by the structural analysis and connectivity network, were identified and various amino acid residues which potentially mediate new or improved contacts were analyzed to identify CDR and/or framework mutations that would result in binding to Zika virus EP. The identified antibodies were found to treat and prevent Zika virus infection in a subject, as well as prevent vertical infection and fetal mortality in a pregnant subject.

Accordingly, the present disclosure relates to antibodies that bind Zika virus EP. Also provided herein are host cells and methods for treating Zika virus with these antibodies.

In some aspects, the isolated monoclonal antibody which specifically binds Zika virus envelope protein, or antigen binding portion thereof, comprises heavy and light chain CDRs, wherein (i) heavy chain CDR1 comprises GFX$_1$FSTY (SEQ ID NO: 54), wherein X$_1$ may or may not be present, and if present is a polar amino acid residue;

(ii) heavy chain CDR2 comprises X$_2$GEGDS (SEQ ID NO: 55), wherein X$_2$ is a polar amino acid residue;

(iii) heavy chain CDR3 comprises GYX$_3$NFYYYYTMDX$_4$ (SEQ ID NO: 56), wherein X$_3$ is a polar amino acid residue and X$_4$ is a nonpolar amino acid residue;

(iv) light chain CDR1 comprises RAX$_5$QSIX$_6$TFLA (SEQ ID NO: 57), wherein X$_5$ is a polar amino acid residue and X$_6$ is a polar amino acid residue or a hydrophobic amino acid residue;

(v) light chain CDR2 comprises DASTX$_7$AX$_8$ (SEQ ID NO: 58), wherein X$_7$ and X$_8$ are polar amino acids; and (vi) light chain CDR3 comprises QQRYNWPPYX$_9$ (SEQ ID NO: 59), wherein X$_9$ is a polar amino acid.

In other aspects, provided herein is an isolated monoclonal antibody, or antigen binding portion thereof, comprising heavy and light chain CDRs wherein (i) heavy chain CDR1 comprises GFX$_1$FSTY (SEQ ID NO: 54), wherein X$_1$ is selected from S and T;

(ii) heavy chain CDR2 comprises X$_2$GEGDS (SEQ ID NO: 55), wherein X$_2$ is selected from S and T;

(iii) heavy chain CDR3 comprises GYX$_3$NFYYYYTMDX$_4$ (SEQ ID NO: 56), wherein X$_3$ is selected from S and T and X$_4$ is selected from A and V;

(iv) light chain CDR1 comprises RAX$_5$QSIX$_6$TFLA (SEQ ID NO: 57), wherein X$_5$ is selected from S and T and X$_6$ is selected from S and V;

(v) light chain CDR2 comprises DASTX$_7$AX$_8$ (SEQ ID NO: 58), wherein X$_7$ is selected from R and N and X$_8$ is selected from S and T; and (vi) light chain CDR3 comprises QQRYNWPPYX$_9$ (SEQ ID NO: 59), wherein X$_9$ is selected from S and T.

In some aspects, the isolated monoclonal antibody, or antigen binding portion thereof, described herein, comprises (i) heavy chain CDR1 comprising GFX$_1$FSTY (SEQ ID NO: 54), wherein X$_1$ is not present;

(ii) heavy chain CDR2 comprising X$_2$GEGDS (SEQ ID NO: 55), wherein X$_2$ is selected from S and T;

(iii) heavy chain CDR3 comprising GYX$_3$NFYYYYTMDX$_4$ (SEQ ID NO: 56), wherein X$_3$ is selected from S and T and X$_4$ is selected from A and V;

(iv) light chain CDR1 comprising RAX$_5$QSIX$_6$TFLA (SEQ ID NO: 57), wherein X$_5$ is selected from S and T and X$_6$ is selected from S and V;

(v) light chain CDR2 comprising DASTX$_7$AX$_8$ (SEQ ID NO: 58), wherein X$_7$ is selected from R and N and X$_5$ is selected from S and T; and (vi) light chain CDR3 comprising QQRYNWPPYX$_9$ (SEQ ID NO: 59), wherein X$_9$ is selected from S and T.

In some aspects, the isolated monoclonal antibody, or antigen binding portion thereof, described herein, comprises, (i) heavy chain CDR1 comprising GFSFSTY (SEQ ID NO: 21);
(ii) heavy chain CDR2 comprising SGEGDS (SEQ ID NO: 27); and
(iii) heavy chain CDR3 comprising GYSNFYYYYTMDA (SEQ ID NO: 32).

In other aspects, the isolated monoclonal antibody, or antigen binding portion thereof, described herein, comprises
(i) heavy chain CDR1 comprising GFSFSTY (SEQ ID NO: 21);
(ii) heavy chain CDR2 comprising TGEGDS (SEQ ID NO: 28); and
(iii) heavy chain CDR3 comprising GYSNFYYYYTMDA (SEQ ID NO: 32).

In some aspects, the isolated monoclonal antibody, or antigen binding portion thereof, described herein, comprises
(i) heavy chain CDR1 comprising GFTFSTY (SEQ ID NO: 22);
(ii) heavy chain CDR2 comprising TGEGDS (SEQ ID NO: 28); and
(iii) heavy chain CDR3 comprising GYSNFYYYYTMDV (SEQ ID NO: 33).

In some aspects, the isolated monoclonal antibody, or antigen binding portion thereof, described herein, comprises
(i) heavy chain CDR1 comprising GFFSTY (SEQ ID NO: 23);
(ii) heavy chain CDR2 comprising TGEGDS (SEQ ID NO: 28); and
(iii) heavy chain CDR3 comprising GYTNFYYYYTMDA (SEQ ID NO: 34).

In other aspects, the isolated monoclonal antibody, or antigen binding portion thereof, described herein, comprises
(i) heavy chain CDR1 comprising GFSFSTY (SEQ ID NO: 21);
(ii) heavy chain CDR2 comprising TGEGDS (SEQ ID NO: 28); and
(iii) heavy chain CDR3 comprising GYTNFYYYYTMDA (SEQ ID NO: 34).

In some aspects, the isolated monoclonal antibody, or antigen binding portion thereof, described herein, comprises
(iv) light chain CDR1 comprising RATQSISTFLA (SEQ ID NO: 38);
(v) light chain CDR2 comprising DASTRAS (SEQ ID NO: 44); and
(vi) light chain CDR3 comprising QQRYNWPPYS (SEQ ID NO: 50).

In some aspects, the isolated monoclonal antibody, or antigen binding portion thereof, described herein, comprises
(iv) light chain CDR1 comprising RASQSISTFLA (SEQ ID NO: 39);
(v) light chain CDR2 comprising DASTRAT (SEQ ID NO: 45); and
(vi) light chain CDR3 comprising QQRYNWPPYT (SEQ ID NO: 51).

In other aspects, the isolated monoclonal antibody, or antigen binding portion thereof, described herein, comprises
(iv) light chain CDR1 comprising RATQSIVTFLA (SEQ ID NO: 40);
(v) light chain CDR2 comprising DASTNAS (SEQ ID NO: 46); and
(vi) light chain CDR3 comprising QQRYNWPPYS (SEQ ID NO: 50).

In some aspects, the isolated monoclonal antibody, or antigen binding portion thereof, described herein, comprises
(i) heavy chain CDR1 comprising GFSFSTY (SEQ ID NO: 21);
(ii) heavy chain CDR2 comprising SGEGDS (SEQ ID NO: 27);
(iii) heavy chain CDR3 comprising GYSNFYYYYTMDA (SEQ ID NO: 32);
(iv) light chain CDR1 comprising RATQSISTFLA (SEQ ID NO: 38);
(v) light chain CDR2 comprising DASTRAS (SEQ ID NO: 44); and
(vi) light chain CDR3 comprising QQRYNWPPYS (SEQ ID NO: 50).

In other aspects, the isolated monoclonal antibody, or antigen binding portion thereof, described herein, comprises
(i) heavy chain CDR1 comprising GFSFSTY (SEQ ID NO: 21);
(ii) heavy chain CDR2 comprising SGEGDS (SEQ ID NO: 27);
(iii) heavy chain CDR3 comprising GYSNFYYYYTMDA (SEQ ID NO: 32);
(iv) light chain CDR1 comprising RATQSIVTFLA (SEQ ID NO: 40);
(v) light chain CDR2 comprising DASTNAS (SEQ ID NO: 46); and
(vi) light chain CDR3 comprising QQRYNWPPYS (SEQ ID NO: 50).

In some aspects, the isolated monoclonal antibody, or antigen binding portion thereof, described herein, comprises
(i) heavy chain CDR1 comprising GFSFSTY (SEQ ID NO: 21);
(ii) heavy chain CDR2 comprising TGEGDS (SEQ ID NO: 28);
(iii) heavy chain CDR3 comprising GYSNFYYYYTMDA (SEQ ID NO: 32);
(iv) light chain CDR1 comprising RATQSISTFLA (SEQ ID NO: 38);
(v) light chain CDR2 comprising DASTRAS (SEQ ID NO: 44); and
(vi) light chain CDR3 comprising QQRYNWPPYS (SEQ ID NO: 50).

In other aspects, the isolated monoclonal antibody, or antigen binding portion thereof, described herein, comprises
(i) heavy chain CDR1 comprising GFTFSTY (SEQ ID NO: 22);
(ii) heavy chain CDR2 comprising TGEGDS (SEQ ID NO: 28);
(iii) heavy chain CDR3 comprising GYSNFYYYYTMDV (SEQ ID NO: 33);
(iv) light chain CDR1 comprising RASQSISTFLA (SEQ ID NO: 39);
(v) light chain CDR2 comprising DASTRAT (SEQ ID NO: 45); and
(vi) light chain CDR3 comprising QQRYNWPPYT (SEQ ID NO: 51).

In some aspects, the disclosure provides an isolated monoclonal antibody which specifically binds Zika virus envelope protein, or antigen binding portion thereof, comprising a heavy chain variable region as set forth in SEQ ID NO: 4, wherein
(i) heavy chain CDR1 comprises an amino acid substitution or deletion at N28, and amino acid substitutions at L29, S31, S32;
(ii) heavy chain CDR2 comprises amino acid substitutions at S52, S52A, S53, Y54, G55;
(iii) heavy chain CDR3 comprises an amino acid deletion at S99 and amino acid substitutions at K100, K100A, P100B, Y100C, F100D, S100E, G100F, W100G, A100H, and Y102; and wherein the heavy chain variable region comprises at least one amino acid deletion at R94, and at CDR3 residues T95, V96, and R97, and combinations thereof, numbering according to Chothia. In some aspects, the heavy chain variable region further comprises at least one amino acid substitution at V5, Y33, A49, S50, T57, A71, T73, A78, S82B, L82C, A93, L108 and combinations thereof, numbering according to Chothia. In some aspects, the heavy chain variable region further comprises an amino acid substitution at T68, numbering according to Chothia. In some aspects, the heavy chain variable region further comprises at least one amino acid substitution at A23, W47, Y58, L80, Q81, A84, and combinations thereof, numbering according to Chothia. In some aspects, the heavy chain variable region further comprises at least one amino acid substitution at E1, A23, R38, W47, Y58, L80, Q81, A84, and combinations thereof, numbering according to Chothia. In some aspects, the heavy chain variable region further comprises at least one amino acid substitution at E1, A23, R38, W47, Y58, T68, L80, Q81, A84, and combinations thereof, numbering according to Chothia.

In any of the foregoing aspects, the isolated monoclonal antibody, or antigen binding portion thereof, described herein, comprising a heavy chain variable region as set forth in SEQ ID NO: 4, comprises
(i) heavy chain CDR1 comprising N28S or N28T, L29F, S31T, S32Y;
(ii) heavy chain CDR2 comprising S52T, S52AG, S53E, Y54G, G55D;
(iii) heavy chain CDR3 comprising K100Y, K100AS or K100AT, P100BN, Y100CF, F100DY, S100EY, G100FY, W100GY, A100HT, and Y102A or Y102V.

In some aspects, the heavy chain variable region comprises amino acid deletions at R94, and at CDR3 residues T95, V96, and R97, numbering according to Chothia.

In any of the foregoing aspects, the isolated monoclonal antibody, or antigen binding portion thereof, described herein, comprises a light chain variable region comprising an amino acid sequence set forth in SEQ ID NO: 5, wherein
(i) light chain CDR1 comprises amino acid substitutions at S26, V29, S31, A32, and V33;
(ii) light chain CDR2 comprises amino acid substitutions at S50, S53, L54, Y55 and optionally S56; and
(iii) light chain CDR3 comprises amino acid substitutions at H91, P93, F94, Y95, L95B, F96, and T97 and an amino acid deletion at G92.

In any of the foregoing aspects, the isolated monoclonal antibody, or antigen binding portion thereof, described herein, comprises
(i) light chain CDR1 comprising S26T, V29I, S31V, A32F, and V33L;
(ii) light chain CDR2 comprising S50D, S53T, L54R or L54N, Y55A and, optionally S56T; and
(ii) light chain CDR3 comprising amino acid substitutions at H91R, P93Y, F94N, Y95W, L95BP, F96Y, and T97S.

In any of the foregoing aspects, the light chain variable region further comprises at least one amino acid substitution at D1, Q3, M4, S9, A13, V15, D17, V19, I21, Y22, Q38, K42, K45, S60, Q79, T85, and combinations thereof, numbering according to Chothia. In some aspects, the light chain variable region further comprises at least one amino acid substitution at S10, V58, S76, S77, V104, and combinations thereof, numbering according to Chothia.

In some aspects, the disclosure provides an isolated monoclonal antibody, or antigen binding portion thereof, which binds to Zika virus envelope protein and comprises heavy and light chain variable regions, wherein the heavy and light chain amino acid sequences are selected from the group consisting of:
(a) SEQ ID NOs: 4 and 14, respectively;
(b) SEQ ID NOs: 4 and 15, respectively;
(c) SEQ ID NOs: 9 and 16, respectively;
(d) SEQ ID NOs: 4 and 16, respectively;
(e) SEQ ID NOs: 4 and 17, respectively;
(f) SEQ ID NOs: 8 and 14, respectively;
(g) SEQ ID NOs: 7 and 17, respectively;
(h) SEQ ID NOs: 6 and 15, respectively;
(i) SEQ ID NOs: 6 and 5, respectively;
(j) SEQ ID NOs: 7 and 5, respectively;
(k) SEQ ID NOs: 8 and 5, respectively;
(l) SEQ ID NOs: 9 and 5, respectively;
(m) SEQ ID NOs: 10 and 5, respectively;
(n) SEQ ID NOs: 11 and 5, respectively;
(o) SEQ ID NOs: 6 and 14, respectively;
(p) SEQ ID NOs: 6 and 16, respectively;
(q) SEQ ID NOs: 6 and 17, respectively;
(r) SEQ ID NOs: 7 and 14, respectively;
(s) SEQ ID NOs: 7 and 15, respectively;
(t) SEQ ID NOs: 7 and 16, respectively;
(u) SEQ ID NOs: 8 and 15, respectively;
(v) SEQ ID NOs: 8 and 16, respectively;
(w) SEQ ID NOs: 8 and 17, respectively;
(x) SEQ ID NOs: 9 and 14, respectively;
(y) SEQ ID NOs: 9 and 15, respectively;
(z) SEQ ID NOs: 9 and 17, respectively;
(aa) SEQ ID NOs: 10 and 14, respectively;
(bb) SEQ ID NOs: 10 and 15, respectively;
(cc) SEQ ID NOs: 10 and 16, respectively;
(dd) SEQ ID NOs: 10 and 17, respectively;
(ee) SEQ ID NOs: 11 and 14, respectively;
(ff) SEQ ID NOs: 11 and 15, respectively;
(gg) SEQ ID NOs: 11 and 16, respectively; and
(hh) SEQ ID NOs: 11 and 17, respectively.

In other aspects, the disclosure provides an isolated monoclonal antibody, or antigen binding portion thereof, which binds to Zika virus envelope protein, comprising heavy and light chain CDRs selected from the group consisting of:
(a) heavy chain CDR1, CDR2 and CDR3 sequences set forth in SEQ ID NOs: 20, 26 and 31, respectively, and light chain CDR1, CDR2 and CDR3 sequences set forth in SEQ ID NOs: 38, 44 and 50, respectively;
(b) heavy chain CDR1, CDR2 and CDR3 sequences set forth in SEQ ID NOs: 22, 28 and 33, respectively, and light chain CDR1, CDR2 and CDR3 sequences set forth in SEQ ID NOs: 39, 45 and 51, respectively;
(c) heavy chain CDR1, CDR2 and CDR3 sequences set forth in SEQ ID NOs: 20, 26 and 31, respectively, and light chain CDR1, CDR2 and CDR3 sequences set forth in SEQ ID NOs: 39, 45 and 51, respectively;
(d) heavy chain CDR1, CDR2 and CDR3 sequences set forth in SEQ ID NOs: 20, 26 and 31, respectively, and light chain CDR1, CDR2 and CDR3 sequences set forth in SEQ ID NOs: 40, 46 and 50, respectively;
(e) heavy chain CDR1, CDR2 and CDR3 sequences set forth in SEQ ID NOs: 21, 28 and 32, respectively, and light chain CDR1, CDR2 and CDR3 sequences set forth in SEQ ID NOs: 38, 44 and 50, respectively;
(f) heavy chain CDR1, CDR2 and CDR3 sequences set forth in SEQ ID NOs: 21, 27 and 32, respectively, and light chain CDR1, CDR2 and CDR3 sequences set forth in SEQ ID NOs: 40, 46 and 50, respectively;

(g) heavy chain CDR1, CDR2 and CDR3 sequences set forth in SEQ ID NOs: 21, 27 and 32, respectively, and light chain CDR1, CDR2 and CDR3 sequences set forth in SEQ ID NOs: 38, 44 and 50, respectively;

(h) heavy chain CDR1, CDR2 and CDR3 sequences set forth in SEQ ID NOs: 21, 27 and 32, respectively, and light chain CDR1, CDR2 and CDR3 sequences set forth in SEQ ID NOs: 37, 43 and 49, respectively;

(i) heavy chain CDR1, CDR2 and CDR3 sequences set forth in SEQ ID NOs: 21, 28 and 32, respectively, and light chain CDR1, CDR2 and CDR3 sequences set forth in SEQ ID NOs: 37, 43 and 49, respectively;

(j) heavy chain CDR1, CDR2 and CDR3 sequences set forth in SEQ ID NOs: 22, 28 and 33, respectively, and light chain CDR1, CDR2 and CDR3 sequences set forth in SEQ ID NOs: 37, 43 and 49, respectively;

(k) heavy chain CDR1, CDR2 and CDR3 sequences set forth in SEQ ID NOs: 23, 28 and 34, respectively, and light chain CDR1, CDR2 and CDR3 sequences set forth in SEQ ID NOs: 37, 43 and 49, respectively;

(l) heavy chain CDR1, CDR2 and CDR3 sequences set forth in SEQ ID NOs: 21, 28 and 34, respectively, and light chain CDR1, CDR2 and CDR3 sequences set forth in SEQ ID NOs: 37, 43 and 49, respectively;

(m) heavy chain CDR1, CDR2 and CDR3 sequences set forth in SEQ ID NOs: 21, 27 and 32, respectively, and light chain CDR1, CDR2 and CDR3 sequences set forth in SEQ ID NOs: 39, 45 and 51, respectively;

(n) heavy chain CDR1, CDR2 and CDR3 sequences set forth in SEQ ID NOs: 21, 28 and 32, respectively, and light chain CDR1, CDR2 and CDR3 sequences set forth in SEQ ID NOs: 39, 45 and 51, respectively;

(o) heavy chain CDR1, CDR2 and CDR3 sequences set forth in SEQ ID NOs: 21, 28 and 32, respectively, and light chain CDR1, CDR2 and CDR3 sequences set forth in SEQ ID NOs: 40, 46 and 50, respectively;

(p) heavy chain CDR1, CDR2 and CDR3 sequences set forth in SEQ ID NOs: 22, 28 and 33, respectively, and light chain CDR1, CDR2 and CDR3 sequences set forth in SEQ ID NOs: 38, 44 and 50, respectively;

(q) heavy chain CDR1, CDR2 and CDR3 sequences set forth in SEQ ID NOs: 22, 28 and 33, respectively, and light chain CDR1, CDR2 and CDR3 sequences set forth in SEQ ID NOs: 40, 46 and 50, respectively;

(r) heavy chain CDR1, CDR2 and CDR3 sequences set forth in SEQ ID NOs: 23, 28 and 34, respectively, and light chain CDR1, CDR2 and CDR3 sequences set forth in SEQ ID NOs: 38, 44 and 50, respectively;

(s) heavy chain CDR1, CDR2 and CDR3 sequences set forth in SEQ ID NOs: 23, 28 and 34, respectively, and light chain CDR1, CDR2 and CDR3 sequences set forth in SEQ ID NOs: 39, 45 and 51, respectively;

(t) heavy chain CDR1, CDR2 and CDR3 sequences set forth in SEQ ID NOs: 23, 28 and 34, respectively, and light chain CDR1, CDR2 and CDR3 sequences set forth in SEQ ID NOs: 40, 46 and 50, respectively;

(u) heavy chain CDR1, CDR2 and CDR3 sequences set forth in SEQ ID NOs: 21, 28 and 34, respectively, and light chain CDR1, CDR2 and CDR3 sequences set forth in SEQ ID NOs: 38, 44 and 50, respectively;

(v) heavy chain CDR1, CDR2 and CDR3 sequences set forth in SEQ ID NOs: 21, 28 and 34, respectively, and light chain CDR1, CDR2 and CDR3 sequences set forth in SEQ ID NOs: 39, 45 and 51, respectively; and (w) heavy chain CDR1, CDR2 and CDR3 sequences set forth in SEQ ID NOs: 21, 28 and 34, respectively, and light chain CDR1, CDR2 and CDR3 sequences set forth in SEQ ID NOs: 40, 46 and 50, respectively.

In some aspects, the disclosure provides an isolated monoclonal antibody, or antigen binding portion thereof, which binds to Zika virus envelope protein and comprises heavy and light chain variable regions, wherein the heavy chain variable region comprises an amino acid sequence which is at least 90% identical to the amino acid sequence selected from the group consisting of SEQ ID NOs: 4, 6, 7, 8, 9, 10 and 11; and wherein the light chain variable region comprises an amino acid sequence which is at least 90% identical to the amino acid sequence selected from the group consisting of SEQ ID NOs: 5, 14, 15, 16, and 17, provided that the monoclonal antibody does not comprise SEQ ID NOs: 4 and 5.

In some aspects, the isolated monoclonal antibody, or antigen binding portion thereof, described herein, comprises heavy chain and light chain sequences having at least 90% identity to the heavy and light chain amino acid sequences selected from the group consisting of:

(a) SEQ ID NOs: 4 and 14, respectively;
(b) SEQ ID NOs: 4 and 15, respectively;
(c) SEQ ID NOs: 9 and 16, respectively;
(d) SEQ ID NOs: 4 and 16, respectively;
(e) SEQ ID NOs: 4 and 17, respectively;
(f) SEQ ID NOs: 8 and 14, respectively;
(g) SEQ ID NOs: 7 and 17, respectively;
(h) SEQ ID NOs: 6 and 15, respectively;
(i) SEQ ID NOs: 6 and 5, respectively;
(j) SEQ ID NOs: 7 and 5, respectively;
(k) SEQ ID NOs: 8 and 5, respectively;
(l) SEQ ID NOs: 9 and 5, respectively;
(m) SEQ ID NOs: 10 and 5, respectively;
(n) SEQ ID NOs: 11 and 5, respectively;
(o) SEQ ID NOs: 6 and 14, respectively;
(p) SEQ ID NOs: 6 and 16, respectively;
(q) SEQ ID NOs: 6 and 17, respectively;
(r) SEQ ID NOs: 7 and 14, respectively;
(s) SEQ ID NOs: 7 and 15, respectively;
(t) SEQ ID NOs: 7 and 16, respectively;
(u) SEQ ID NOs: 8 and 15, respectively;
(v) SEQ ID NOs: 8 and 16, respectively;
(w) SEQ ID NOs: 8 and 17, respectively;
(x) SEQ ID NOs: 9 and 14, respectively;
(y) SEQ ID NOs: 9 and 15, respectively;
(z) SEQ ID NOs: 9 and 17, respectively;
(aa) SEQ ID NOs: 10 and 14, respectively;
(bb) SEQ ID NOs: 10 and 15, respectively;
(cc) SEQ ID NOs: 10 and 16, respectively;
(dd) SEQ ID NOs: 10 and 17, respectively;
(ee) SEQ ID NOs: 11 and 14, respectively;
(ff) SEQ ID NOs: 11 and 15, respectively;
(gg) SEQ ID NOs: 11 and 16, respectively; and
(hh) SEQ ID NOs: 11 and 17, respectively.

Some aspects of the disclosure relate to any of the preceding isolated monoclonal antibodies, or antigen binding portions thereof, in which the antibody is a humanized antibody.

Other aspects of the disclosure relate to any of the preceding isolated monoclonal antibodies, or antigen binding portions thereof, in which the antibody has neutralizing activity against Zika virus.

Some aspects of the disclosure relate to any of the preceding isolated monoclonal antibodies, or antigen binding portions thereof, in which the antibody is selected from the group consisting of an IgG1, an IgG2, an IgG3, an IgG4, an IgM, an IgA1, an IgA2, an IgD, and an IgE antibody. In some aspects of the disclosure, any of the preceding isolated monoclonal antibodies, or antigen binding portions thereof, is an IgG1 antibody.

Other aspects of the disclosure relate to a pharmaceutical composition comprising any of the preceding isolated monoclonal antibodies, or antigen binding portions thereof, and a pharmaceutically acceptable carrier.

Another aspect of the disclosure relates to a method for treating Zika virus infection in a subject in need thereof, comprising administering an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier.

Another aspect of the disclosure relates to a method for preventing Zika virus infection in a subject, comprising administering an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier.

In other aspects, the disclosure relates to methods for treating or preventing vertical infection to a fetus in a pregnant subject, comprising administering an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier. In some aspects, the disclosure relates to methods for reducing or reducing the risk of vertical infection to a fetus in a pregnant subject, comprising administering an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier.

In another aspect, the disclosure relates to methods for treating or preventing fetal Zika virus infection, comprising administering to a pregnant subject in need thereof, an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier. In some aspects, the disclosure relates to methods for reducing or reducing the risk of fetal Zika virus infection, comprising administering to a pregnant subject an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier.

Another aspect of the disclosure relates to methods for treating or preventing fetal mortality in a pregnant subject, comprising administering to the subject an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier. In some aspects, the disclosure relates to methods for reducing or reducing the risk of fetal mortality in a pregnant subject, comprising administering an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier.

In other aspects, the disclosure relates to methods for treating or preventing placental Zika virus infection, comprising administering to a pregnant subject in need thereof, an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier. In some aspects, the disclosure relates to methods for reducing or reducing the risk of placental Zika virus infection, comprising administering to a pregnant subject an effective amount of any of the preceding isolated monoclonal antibodies, or antigen binding portions thereof, or a pharmaceutical composition comprising any of the preceding isolated monoclonal antibodies, or antigen binding portions thereof, and a pharmaceutically acceptable carrier.

In any of the foregoing methods, the pregnant subject is infected with Zika virus. In some aspects, the pregnant subject is at risk of being infected with Zika virus.

Some aspects of the disclosure relate to a nucleic acid comprising a nucleotide sequence encoding the light chain, heavy chain, or both light and heavy chains of any of the preceding isolated monoclonal antibodies, or antigen binding portions thereof. In some aspects, the disclosure relates to an expression vector comprising the nucleic acid. In further aspects, the disclosure relates to a cell transformed with the expression vector.

BRIEF DESCRIPTION OF THE FIGURES

FIG. 1A shows the heavy chain sequence for anti-TDRD3 antibody (top) and the heavy chain sequences for the anti-Zika antibodies generated (bottom). Modifications are bold and underlined. The anti-TDRD3 antibody heavy chain variable region sequence is set forth as SEQ ID NO: 4. The generated anti-Zika virus antibody heavy chain variable region sequences are set forth as: VH.1 (SEQ ID NO: 6); VH.2 (SEQ ID NO: 7); VH.3 (SEQ ID NO: 8); VH.4 (SEQ ID NO: 9); VH.5 (SEQ ID NO: 10); and VH.6 (SEQ ID NO: 11).

FIG. 1B shows the light chain sequence for anti-TDRD3 antibody (top) and the light chain sequences for the anti-Zika antibodies generated (bottom). Modifications are bold and underlined. The anti-TDRD3 antibody light chain variable region sequence is set forth as SEQ ID NO: 5. The generated anti-Zika virus antibody light chain variable region sequences are set forth as: VL.1 (SEQ ID NO: 14); VL.2 (SEQ ID NO: 15); VL.3 (SEQ ID NO: 16); VL.4 (SEQ ID NO: 17).

Figure 2:
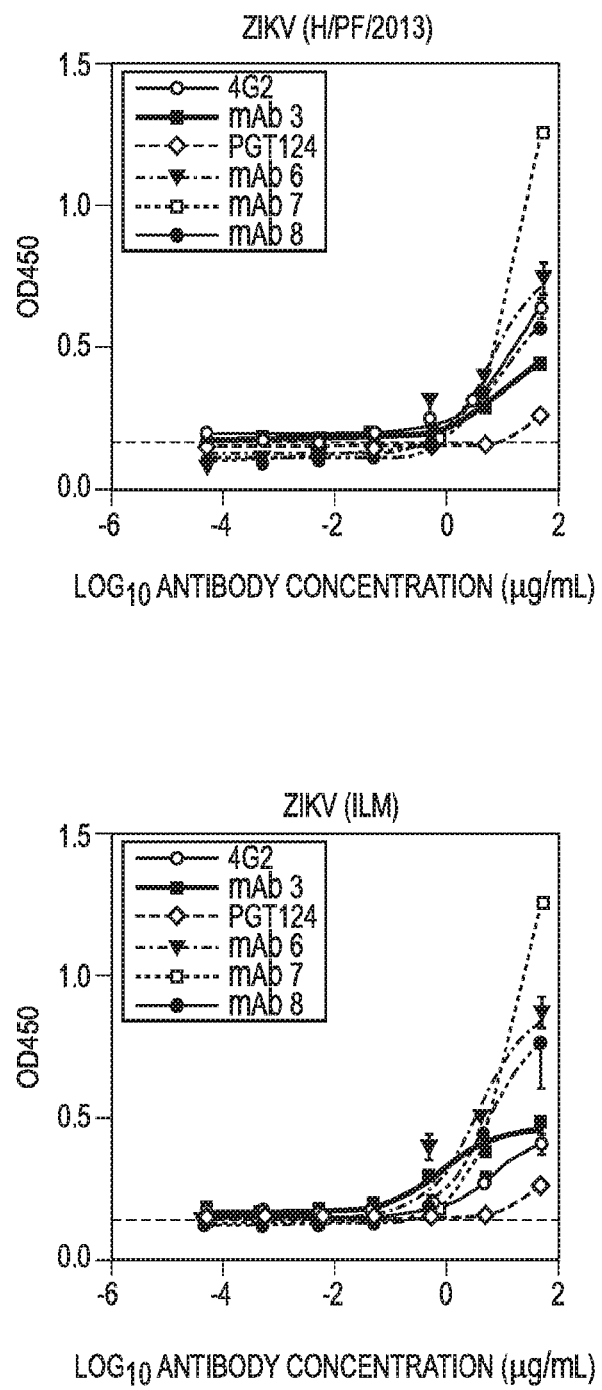
FIG. 2 shows binding data of anti-Zika antibodies to different strains of Zika virus as measured by a sandwich ELISA.

FIGS. 3A and 3B are graphs showing the percent neutralization by anti-Zika antibodies determined in a plaque reduction neutralization test using the Zika virus ILM strain (Brazil Paraiba 2015) (3A) or H/PF/2013 strain (3B).

FIGS. 4A-4D are graphs showing body weight over time (4A and 4B) and survival over time (4C and 4D) in mice with Zika virus infection (H/PF/2013 strain) treated either prophylactically (4A and 4C) or therapeutically (4B and 4D) with anti-Zika antibodies.

FIG. 5 is graphs depicting viral load over time in mice with Zika virus infection (H/PF/2013 strain) treated either prophylactically (top) or therapeutically (bottom) with anti-Zika antibodies.
Figure 2:
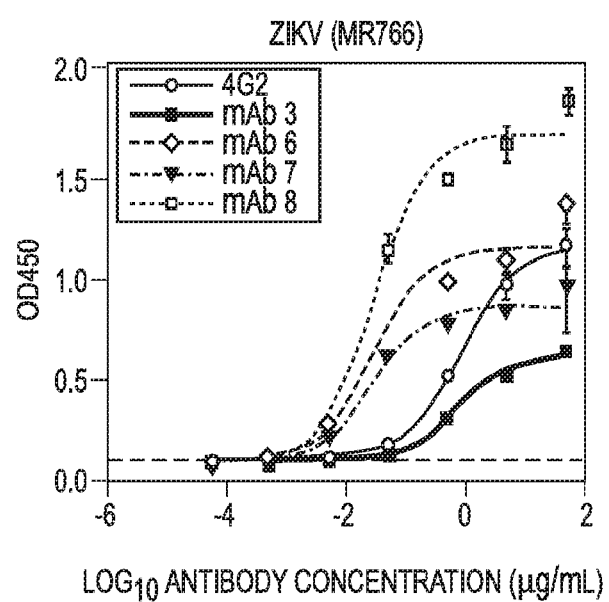

FIG. 8A is a schematic providing the study design for assessing vertical infection and fetal mortality in pregnant A129 mice infected with Zika virus (H/PF/2013 strain).

FIGS. 8B-8F provide graphs showing the results of the study described in FIG. 8A. Specifically, levels of viral RNA in the mothers at day 2 (8B) or day 7 (8C), percent fetus survival as measured by percent lethality (8D), and viral RNA in fetuses (8E) or placenta (8F) from mice treated with an isotype control IgG or mAb 8 are shown.

DETAILED DESCRIPTION

Definitions

Terms used in the claims and specification are defined as set forth below unless otherwise specified.

The term "Zika virus", refers to members of the family Flaviviridae, and is normally associated with mild symptoms including fever, rash joint pain or conjunctivitis, but has recently been linked to microcephaly in newborn babies by mother-to-child transmission and Guillain-Barre syndrome. The genome of Zika virus consists of a single strand of positive sense RNA that is approximately 11 kb in length. Zika virions, like virions of other flaviviruses, contain 10 functionally distinct proteins, including three structural proteins incorporated into the virus particle.

The term "Zika virus envelope protein ("E" or "EP")" refers to the protein responsible for viral entry and virion budding. It is composed of three distinct domains. E Domain I (E-DI) is the central domain that organizes the entire E protein structure. E Domain II (E-DII) is formed from two extended loops projecting from E-DI and lies in a pocket at the E-DI and E Domain III (E-DIII). E-DIII is an immunoglobulin-like domain that forms small protrusions on the surface of an otherwise smooth spherical mature virus particle, and is thought to interact with cellular receptors on target cells. At the distal end of E-DII is a glycine-rich, hydrophobic sequences referred to as the "fusion loop." The fusion loop encompasses residues 98 to 110 and is highly conserved among flaviviruses. In certain embodiments, "Zika virus envelope protein" refers to the fusion loop. In certain embodiments, the fusion loop has the amino acid sequence set forth in SEQ ID NO: 3.

The term "antibody" as referred to herein includes whole antibodies and any antigen binding fragment (i.e., "antigen-binding portion") or single chain thereof. An "antibody" refers, in certain embodiments, to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., Zika virus EP). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "monoclonal antibody," as used herein, refers to an antibody which displays a single binding specificity and affinity for a particular epitope. Accordingly, the term "human monoclonal antibody" refers to an antibody which displays a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

The term "human antibody" includes antibodies having variable and constant regions (if present) of human germline immunoglobulin sequences. Human antibodies of the disclosure can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) *Handbook of Experimental Pharmacology* 113:49-101; Lonberg, N. and Huszar, D. (1995) *Intern. Rev. Immunol.* Vol. 13: 65-93, and Harding, F. and Lonberg, N. (1995) *Ann. N.Y. Acad. Sci* 764:536-546). However, the term "human antibody" does not include antibodies in which CDR sequences derived from the germline of another mammalian species, such as a mouse, have been grafted onto human framework sequences (i.e., humanized antibodies).

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, "neutralizing antibody" refers to an antibody, for example, a monoclonal antibody, capable of disrupting a formed viral particle or inhibiting formatting of a viral particle or prevention of binding to or infection of mammalian cells by a viral particle. In some embodiments, the antibodies described herein neutralize Zika virus.

As used herein, "diagnostic antibody" or "detection antibody" or "detecting antibody" refers to an antibody, for example, a monoclonal antibody, capable of detecting the presence of an antigenic target within a sample. As will be appreciated by one of skill in the art, such diagnostic antibodies preferably have high specificity for their antigenic target.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino acid sequence for comparison purposes, the region shares at least 80-90%, preferably at least 90-95%, more preferably at least 95-99% identity (i.e., local sequence identity) with the human framework or constant region sequence, allowing, for example, for conservative substitutions, consensus sequence substitutions, germline substitutions, back-mutations, and the like. The introduction of conservative substitutions, consensus sequence substitutions, germline substitutions, back-mutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably at least 90-95%, more preferably, 96%, 97%, 98%, or 99% identical to that of a non-human organism, e.g., a non-human mammal.

Referring to the well-recognized nomenclature for amino acids, the three letter code, or one letter code, is used, including the codes "Xaa" or "X" to indicate any amino acid residue. Thus, Xaa or X may typically represent any of the 20 naturally occurring amino acids.

Preferably, residue positions which are not identical differ by conservative amino acid substitutions. For purposes of classifying amino acids substitutions as conservative or nonconservative, amino acids are grouped as follows: Group I (hydrophobic sidechains): leu, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

A mutation (e.g., a back-mutation) is said to substantially affect the ability of a heavy or light chain to direct antigen binding if it affects (e.g., decreases) the binding affinity of an intact immunoglobulin or antibody (or antigen binding fragment thereof) comprising said chain by at least an order of magnitude compared to that of the antibody (or antigen binding fragment thereof) comprising an equivalent chain lacking said mutation. A mutation "does not substantially affect (e.g., decrease) the ability of a chain to direct antigen binding" if it affects (e.g., decreases) the binding affinity of an intact immunoglobulin or antibody (or antigen binding fragment thereof) comprising said chain by only a factor of two, three, or four of that of the antibody (or antigen binding fragment thereof) comprising an equivalent chain lacking said mutation.

In certain embodiments, humanized immunoglobulins or antibodies bind antigen with an affinity that is within a factor of three, four, or five of that of the corresponding nonhumanized antibody. For example, if the nonhumanized antibody has a binding affinity of $10^9$ $M^{-1}$, humanized antibodies will have a binding affinity of at least 3 times $10^9$ $M^{-1}$, 4 times $10^9$ $M^{-1}$ or $10^9$ $M^{-1}$. When describing the binding properties of an immunoglobulin or antibody chain, the chain can be described based on its ability to "direct antigen (e.g., Zika virus EP) binding". A chain is said to "direct antigen binding" when it confers upon an intact immunoglobulin or antibody (or antigen binding fragment thereof) a specific binding property or binding affinity.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species. The terms "humanized immunoglobulin" or "humanized antibody" are not intended to encompass chimeric immunoglobulins or antibodies, as defined infra. Although humanized immunoglobulins or antibodies are chimeric in their construction (i.e., comprise regions from more than one species of protein), they include additional features (i.e., variable regions comprising donor CDR residues and acceptor framework residues) not found in chimeric immunoglobulins or antibodies, as defined herein.

An "isolated antibody," as used herein, is intended to refer to an antibody which is substantially free of other antibodies having different antigenic specificities (e.g., an isolated antibody that specifically binds to Zika virus EP is substantially free of antibodies that specifically bind antigens other than Zika virus EP). An isolated antibody is typically substantially free of other cellular material and/or chemicals. In certain embodiments of the disclosure, a combination of "isolated" antibodies having different Zika virus EP specificities is combined in a well-defined composition.

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from Zika virus EP are tested for reactivity with the given anti-EP antibody. Methods of determining spatial conformation of epitopes include techniques in the art and those described herein, for example, x-ray crystallography and 2-dimensional nuclear magnetic resonance (see, e.g., *Epitope Mapping Protocols in Methods in Molecular Biology*, Vol. 66, G. E. Morris, Ed. (1996)).

Antibodies that recognize the same epitope can be identified in a simple immunoassay showing the ability of one antibody to block the binding of another antibody to a target antigen, i.e., a competitive binding assay. Competitive binding is determined in an assay in which the immunoglobulin under test inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242 (1983)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., Mol. Immunol. 25(1):7 (1988)); solid phase direct biotin-avidin EIA (Cheung et al., Virology 176:546 (1990)); and direct labeled RIA. (Moldenhauer et al., Scand. J. Immunol. 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70% 70-75% or more.

The term "epitope mapping" refers to the process of identification of the molecular determinants for antibody-antigen recognition. Numerous methods for epitope mapping are known in the art, such as x-ray analysis, protease mapping, hydrogen/deuterium exchange mass spectrometry (HDX-MS), 2D nuclear magnetic resonance, alanine scanning, and deep mutational scanning.

To facilitate engineering of antibodies that target the Zika virus envelope protein (EP), epitope hotspots were determined by analyzing the percent buried surface area of interface residues. In some embodiments, the anti-Zika virus antibodies described herein bind an epitope on the fusion loop comprising residues D98, R99 and W101 (SEQ ID NO: 3).

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

As used herein, the terms "specific binding," "selective binding," "selectively binds," and "specifically binds," refer to antibody binding to an epitope on a predetermined antigen. Typically, the antibody binds with an equilibrium dissociation constant ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE 2000 instrument using recombinant Zika virus EP as the analyte and the antibody as the ligand and binds to the predetermined antigen with an affinity that is at least two-fold greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

The term "$K_D$," as used herein, is intended to refer to the dissociation equilibrium constant of a particular antibody-antigen interaction.

The term "kd" as used herein, is intended to refer to the off rate constant for the dissociation of an antibody from the antibody/antigen complex.

The term "ka" as used herein, is intended to refer to the on rate constant for the association of an antibody with the antigen.

The term "EC50," as used herein, refers to the concentration of an antibody or an antigen-binding portion thereof, which induces a response, either in an in vitro or an in vivo assay, which is 50% of the maximal response, i.e., halfway between the maximal response and the baseline.

As used herein, "isotype" refers to the antibody class (e.g., IgM or IgG1) that is encoded by heavy chain constant region genes. In one embodiment, a human monoclonal antibody of the disclosure is of the IgG1 isotype. In certain embodiments, the human IgG1 has a heavy chain constant domain sequence as set forth in SEQ ID NO: 1 and a light chain constant domain sequence as set forth in SEQ ID NO: 2.

The term "binds to Zika virus EP," refers to the ability of an antibody described herein to bind to Zika virus EP, for example, expressed on the surface of a cell or which is attached to a solid support.

The term "nucleic acid molecule," as used herein, is intended to include DNA molecules and RNA molecules. A nucleic acid molecule may be single-stranded or double-stranded, but preferably is double-stranded DNA.

The present disclosure also encompasses "conservative sequence modifications" of the sequences set forth in SEQ ID NOs: 4-53 i.e., amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into SEQ ID NOs: 4-53 by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-EP antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)).

Alternatively, in certain embodiments, mutations can be introduced randomly along all or part of an anti-EP antibody coding sequence, such as by saturation mutagenesis, and the resulting modified anti-EP antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at gcg.com), using a NWSgap-dna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules of the disclosure. BLAST protein searches can be performed with the XBLAST program, score=50, wordlength=3 to obtain amino acid sequences homologous to the protein molecules of the disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

When given an amino acid sequence, one versed in the art can make conservative substitutions to the nucleotide sequence encoding it without altering the amino acid sequence, given the redundancy in the genetic code. The nucleic acid compositions, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The terms "treat," "treating," and "treatment," as used herein, refer to therapeutic or preventative measures described herein. The methods of "treatment" employ administration to a subject, in need of such treatment, a human antibody of the present disclosure, for example, a subject in need of an enhanced immune response against a particular antigen (e.g., Zika virus) or a subject who ultimately may acquire such a disorder, in order to prevent, cure, delay, reduce the severity of, or ameliorate one or more symptoms of the disorder or recurring disorder, or in order to prolong the survival of a subject beyond that expected in the absence of such treatment.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts effective for this use will depend upon the severity of the disorder being treated and the general state of the patient's own immune system.

The term "patient" includes human and other mammalian subjects that receive either prophylactic or therapeutic treatment.

As used herein, the term "subject" includes any human or non-human animal. For example, the methods and compositions of the present disclosure can be used to treat a subject with an immune disorder. The term "non-human animal" includes all vertebrates, e.g., mammals and non-mammals, such as non-human primates, sheep, dog, cow, chickens, amphibians, reptiles, etc. In some embodiments, the subject is pregnant.

As used herein, the term "vertical infection" refers to mother-to-child transmission of a pathogen (e.g., Zika virus). In some embodiments, the anti-Zika virus EP antibodies described herein prevent vertical infection in a pregnant subject.

Various aspects of the disclosure are described in further detail in the following subsections.

Production of Antibodies to Zika Virus Envelope Protein

The present disclosure encompasses antibodies that bind Zika virus EP. In some embodiments, antibodies that bind Zika virus EP are optimized monoclonal antibodies which include CDRs, or optimized CDRs, based on an anti-TDRD3 (Tudor Domain Containing 3) human monoclonal antibody. Provided herein are isolated monoclonal antibodies or antigen binding portions thereof, comprising heavy and light chain variable region sequences comprising (further described in Tables 2 and 3):

(a) a heavy chain comprising CDR1, CDR2 and CDR3 sequences set forth in SEQ ID NOs: 20, 26 and 31, respectively, and a light chain comprising CDR1, CDR2 and CDR3 sequences set forth in SEQ ID NOs: 38, 44 and 50, respectively;

(b) a heavy chain comprising CDR1, CDR2 and CDR3 sequences set forth in SEQ ID NOs: 22, 28 and 33, respectively, and a light chain comprising CDR1, CDR2 and CDR3 sequences set forth in SEQ ID NOs: 39, 45 and 51, respectively;

(c) a heavy chain comprising CDR1, CDR2 and CDR3 sequences set forth in SEQ ID NOs: 20, 26 and 31, respectively, and a light chain comprising CDR1, CDR2 and CDR3 sequences set forth in SEQ ID NOs: 39, 45 and 51, respectively;

(d) a heavy chain comprising CDR1, CDR2 and CDR3 sequences set forth in SEQ ID NOs: 20, 26 and 31, respectively, and a light chain comprising CDR1, CDR2 and CDR3 sequences set forth in SEQ ID NOs: 40, 46 and 50, respectively;

(e) a heavy chain comprising CDR1, CDR2 and CDR3 sequences set forth in SEQ ID NOs: 21, 28 and 32, respectively, and a light chain comprising CDR1, CDR2 and CDR3 sequences set forth in SEQ ID NOs: 38, 44 and 50, respectively;

(f) a heavy chain comprising CDR1, CDR2 and CDR3 sequences set forth in SEQ ID NOs: 21, 27 and 32, respectively, and a light chain comprising CDR1, CDR2 and CDR3 sequences set forth in SEQ ID NOs: 40, 46 and 50, respectively;

(g) a heavy chain comprising CDR1, CDR2 and CDR3 sequences set forth in SEQ ID NOs: 21, 27 and 32, respectively, and a light chain comprising CDR1, CDR2 and CDR3 sequences set forth in SEQ ID NOs: 38, 44 and 50, respectively;

(h) a heavy chain comprising CDR1, CDR2 and CDR3 sequences set forth in SEQ ID NOs: 21, 27 and 32, respectively, and a light chain comprising CDR1, CDR2 and CDR3 sequences set forth in SEQ ID NOs: 37, 43 and 49, respectively;

(i) a heavy chain comprising CDR1, CDR2 and CDR3 sequences set forth in SEQ ID NOs: 21, 28 and 32, respectively, and a light chain comprising CDR1, CDR2 and CDR3 sequences set forth in SEQ ID NOs: 37, 43 and 49, respectively;

(j) a heavy chain comprising CDR1, CDR2 and CDR3 sequences set forth in SEQ ID NOs: 22, 28 and 33, respectively, and a light chain comprising CDR1, CDR2 and CDR3 sequences set forth in SEQ ID NOs: 37, 43 and 49, respectively;

(k) a heavy chain comprising CDR1, CDR2 and CDR3 sequences set forth in SEQ ID NOs: 23, 28 and 34, respectively, and a light chain comprising CDR1, CDR2 and CDR3 sequences set forth in SEQ ID NOs: 37, 43 and 49, respectively;

(l) a heavy chain comprising CDR1, CDR2 and CDR3 sequences set forth in SEQ ID NOs: 21, 28 and 34, respectively, and a light chain comprising CDR1, CDR2 and CDR3 sequences set forth in SEQ ID NOs: 37, 43 and 49, respectively;

(m) a heavy chain comprising CDR1, CDR2 and CDR3 sequences set forth in SEQ ID NOs: 21, 27 and 32, respectively, and a light chain comprising CDR1, CDR2 and CDR3 sequences set forth in SEQ ID NOs: 39, 45 and 51, respectively;

(n) a heavy chain comprising CDR1, CDR2 and CDR3 sequences set forth in SEQ ID NOs: 21, 28 and 32, respectively, and a light chain comprising CDR1, CDR2 and CDR3 sequences set forth in SEQ ID NOs: 39, 45 and 51, respectively;

(o) a heavy chain comprising CDR1, CDR2 and CDR3 sequences set forth in SEQ ID NOs: 21, 28 and 32, respectively, and a light chain comprising CDR1, CDR2 and CDR3 sequences set forth in SEQ ID NOs: 40, 46 and 50, respectively;

(p) a heavy chain comprising CDR1, CDR2 and CDR3 sequences set forth in SEQ ID NOs: 22, 28 and 33, respectively, and a light chain comprising CDR1, CDR2 and CDR3 sequences set forth in SEQ ID NOs: 38, 44 and 50, respectively;

(q) a heavy chain comprising CDR1, CDR2 and CDR3 sequences set forth in SEQ ID NOs: 22, 28 and 33, respectively, and a light chain comprising CDR1, CDR2 and CDR3 sequences set forth in SEQ ID NOs: 40, 46 and 50, respectively;

(r) a heavy chain comprising CDR1, CDR2 and CDR3 sequences set forth in SEQ ID NOs: 23, 28 and 34, respectively, and a light chain comprising CDR1, CDR2 and CDR3 sequences set forth in SEQ ID NOs: 38, 44 and 50, respectively;

(s) a heavy chain comprising CDR1, CDR2 and CDR3 sequences set forth in SEQ ID NOs: 23, 28 and 34, respectively, and a light chain comprising CDR1, CDR2 and CDR3 sequences set forth in SEQ ID NOs: 39, 45 and 51, respectively;

(t) a heavy chain comprising CDR1, CDR2 and CDR3 sequences set forth in SEQ ID NOs: 23, 28 and 34, respectively, and a light chain comprising CDR1, CDR2 and CDR3 sequences set forth in SEQ ID NOs: 40, 46 and 50, respectively;

(u) a heavy chain comprising CDR1, CDR2 and CDR3 sequences set forth in SEQ ID NOs: 21, 28 and 34, respectively, and a light chain comprising CDR1, CDR2 and CDR3 sequences set forth in SEQ ID NOs: 38, 44 and 50, respectively;

(v) a heavy chain comprising CDR1, CDR2 and CDR3 sequences set forth in SEQ ID NOs: 21, 28 and 34, respectively, and a light chain comprising CDR1, CDR2 and CDR3 sequences set forth in SEQ ID NOs: 39, 45 and 51, respectively; and (w) a heavy chain comprising CDR1, CDR2 and CDR3 sequences set forth in SEQ ID NOs: 21, 28 and 34, respectively, and a light chain comprising CDR1, CDR2 and CDR3 sequences set forth in SEQ ID NOs: 40, 46 and 50, respectively.

In some embodiments, antibodies that bind Zika virus EP are optimized monoclonal antibodies which include heavy and/or light chain variable regions, or optimized heavy and/or light chain variable regions, based on an anti-TDRD3 human monoclonal antibody. Also provided herein, are isolated monoclonal antibodies or antigen binding portions thereof, comprising heavy and light chain variable sequences comprising:

(a) SEQ ID NOs: 4 and 14, respectively;
(b) SEQ ID NOs: 4 and 15, respectively;
(c) SEQ ID NOs: 9 and 16, respectively;
(d) SEQ ID NOs: 4 and 16, respectively;
(e) SEQ ID NOs: 4 and 17, respectively;
(f) SEQ ID NOs: 8 and 14, respectively;
(g) SEQ ID NOs: 7 and 17, respectively;
(h) SEQ ID NOs: 6 and 15, respectively;
(i) SEQ ID NOs: 6 and 5, respectively;
(j) SEQ ID NOs: 7 and 5, respectively;
(k) SEQ ID NOs: 8 and 5, respectively;
(l) SEQ ID NOs: 9 and 5, respectively;
(m) SEQ ID NOs: 10 and 5, respectively;
(n) SEQ ID NOs: 11 and 5, respectively;
(o) SEQ ID NOs: 6 and 14, respectively;
(p) SEQ ID NOs: 6 and 16, respectively;
(q) SEQ ID NOs: 6 and 17, respectively;
(r) SEQ ID NOs: 7 and 14, respectively;
(s) SEQ ID NOs: 7 and 15, respectively;
(t) SEQ ID NOs: 7 and 16, respectively;
(u) SEQ ID NOs: 8 and 15, respectively;

(v) SEQ ID NOs: 8 and 16, respectively;
(w) SEQ ID NOs: 8 and 17, respectively;
(x) SEQ ID NOs: 9 and 14, respectively;
(y) SEQ ID NOs: 9 and 15, respectively;
(z) SEQ ID NOs: 9 and 17, respectively;
(aa) SEQ ID NOs: 10 and 14, respectively;
(bb) SEQ ID NOs: 10 and 15, respectively;
(cc) SEQ ID NOs: 10 and 16, respectively;
(dd) SEQ ID NOs: 10 and 17, respectively;
(ee) SEQ ID NOs: 11 and 14, respectively;
(ff) SEQ ID NOs: 11 and 15, respectively;
(gg) SEQ ID NOs: 11 and 16, respectively; and
(hh) SEQ ID NOs: 11 and 17, respectively.

Monoclonal antibodies described herein can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

Accordingly, in certain embodiments, a hybridoma method is used for producing an antibody that binds Zika virus EP. In this method, a mouse or other appropriate host animal can be immunized with a suitable antigen in order to elicit lymphocytes that produce or are capable of producing antibodies that will specifically bind to the antigen used for immunization. Alternatively, lymphocytes may be immunized in vitro. Lymphocytes can then be fused with myeloma cells using a suitable fusing agent, such as polyethylene glycol, to form a hybridoma cell (Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, DMEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

In certain embodiments, antibodies and antibody portions that bind Zika virus EP can be isolated from antibody phage libraries generated using the techniques described in, for example, McCafferty et al., Nature, 348:552-554 (1990). Clackson et al., Nature, 352:624-628 (1991), Marks et al., J. Mol. Biol., 222:581-597 (1991) and Hoet et al (2005) Nature Biotechnology 23, 344-348; U.S. Pat. Nos. 5,223,409; 5,403,484; and U.S. Pat. No. 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al. Additionally, production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)) may also be used.

In certain embodiments, the antibody that binds Zika virus EP is produced using the phage display technique described by Hoet et al., supra. This technique involves the generation of a human Fab library having a unique combination of immunoglobulin sequences isolated from human donors and having synthetic diversity in the heavy-chain CDRs is generated. The library is then screened for Fabs that bind to Zika virus EP.

The preferred animal system for generating hybridomas which produce antibodies of the disclosure is the murine system. Hybridoma production in the mouse is well known in the art, including immunization protocols and techniques for isolating and fusing immunized splenocytes.

In certain embodiments, antibodies directed against Zika virus EP are generated using transgenic or transchromosomal mice carrying parts of the human immune system rather than the mouse system. In some embodiments, antibodies described herein are generated using transgenic mice, referred to herein as "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. Vol. 13: 65-93, and Harding, F. and Lonberg, N. (1995) Ann. N.Y. Acad. Sci 764:536-546). The preparation of HuMAb mice is described in detail below and in Taylor, L. et al. (1992) Nucleic Acids Research 20:6287-6295; Chen, J. et al. (1993) International Immunology 5: 647-656; Tuaillon et al. (1993) Proc. Natl. Acad. Sci USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Lonberg et al., (1994) Nature 368(6474): 856-859; Lonberg, N. (1994) Handbook of Experimental Pharmacology 113:49-101; Taylor, L. et al. (1994) International Immunology 6: 579-591; Lonberg, N. and Huszar, D. (1995) Intern. Rev. Immunol. Vol. 13: 65-93; Harding, F. and Lonberg, N. (1995) Ann. N.Y. Acad. Sci 764:536-546; Fishwild, D. et al. (1996) Nature Biotechnology 14: 845-851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992).

In certain embodiments, antibodies described herein can be raised using a mouse that carries human immunoglobulin sequences on transgenes and transchomosomes, such as a mouse that carries a human heavy chain transgene and a human light chain transchromosome. Such mice, referred to in the art as "KM mice", are described in detail in PCT Publication WO 02/43478 to Ishida et al.

Still further, alternative transgenic animal systems expressing human immunoglobulin genes are available in the art and can be used to raise anti-Zika virus EP antibodies of the disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-Zika virus EP antibodies described herein. For example, mice carrying both a human heavy chain transchromosome and a human light chain tranchromosome, referred to in the art as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-Zika virus EP antibodies of the disclosure.

Additional mouse systems described in the art for raising human antibodies also can be applied to raising anti-Zika virus EP antibodies of the disclosure, including but not limited to (i) the VelocImmune® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the mAbs described herein can be produced in plants using deconstructed viral vectors, as described in Olinger et al., *PNAS* 2012; 109, 18030-18035, herein incorporated by reference. In certain embodiments, the mAbs are produced in tobacco plants.

In certain embodiments, chimeric antibodies can be prepared based on the sequence of a murine monoclonal antibodies described herein. A chimeric antibody refers to an antibody whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. A typical chimeric antibody is thus a hybrid protein consisting of the V or antigen-binding domain from a mouse antibody and the C or effector domain from a human antibody.

Production of Humanized Antibodies

The term "humanized antibody" refers to an antibody comprising at least one chain comprising variable region framework residues substantially from a human antibody chain (referred to as the acceptor immunoglobulin or antibody) and at least one complementarity determining region substantially from a mouse antibody, (referred to as the donor immunoglobulin or antibody). See, Queen et al., Proc. Natl. Acad. Sci. USA 86:10029-10033 (1989), U.S. Pat. Nos. 5,530,101, 5,585,089, 5,693,761, 5,693,762, Selick et al., WO 90/07861, and Winter, U.S. Pat. No. 5,225,539 (incorporated by reference in their entirety for all purposes). The constant region(s), if present, are also substantially or entirely from a human immunoglobulin.

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993) and Carter et al., WO 92/22653.

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining an immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIA-CORE) and/or solid-phase ELISA analysis.

Certain amino acids from the human variable region framework residues are selected for substitution based on their possible influence on CDR conformation and/or binding to antigen. The unnatural juxtaposition of murine CDR regions with human variable framework region can result in unnatural conformational restraints, which, unless corrected by substitution of certain amino acid residues, lead to loss of binding affinity.

The selection of amino acid residues for substitution is determined, in part, by computer modeling. Computer hardware and software are described herein for producing three-dimensional images of immunoglobulin molecules. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

The selection of amino acid residues for substitution can also be determined, in part, by examination of the characteristics of the amino acids at particular locations, or empirical observation of the effects of substitution or mutagenesis of particular amino acids. For example, when an amino acid differs between a murine variable region framework residue and a selected human variable region framework residue, the human framework amino acid should usually be substituted by the equivalent framework amino acid from the mouse antibody when it is reasonably expected that the amino acid:
 (1) noncovalently binds antigen directly,
 (2) is adjacent to a CDR region,
 (3) otherwise interacts with a CDR region (e.g., is within about 3-6 angstroms of a CDR region as determined by computer modeling), or
 (4) participates in the VL-VH interface.

Residues which "noncovalently bind antigen directly" include amino acids in positions in framework regions which have a good probability of directly interacting with amino acids on the antigen according to established chemical forces, for example, by hydrogen bonding, Van der Waals forces, hydrophobic interactions, and the like.

CDR and framework regions are as defined by Kabat et al. or Chothia et al., supra. When framework residues, as defined by Kabat et al., supra, constitute structural loop residues as defined by Chothia et al., supra, the amino acids present in the mouse antibody may be selected for substitution into the humanized antibody. Residues which are "adjacent to a CDR region" include amino acid residues in positions immediately adjacent to one or more of the CDRs in the primary sequence of the humanized immunoglobulin chain, for example, in positions immediately adjacent to a CDR as defined by Kabat, or a CDR as defined by Chothia (See e.g., Chothia and Lesk J M B 196:901 (1987)). These amino acids are particularly likely to interact with the amino acids in the CDRs and, if chosen from the acceptor, to distort the donor CDRs and reduce affinity. Moreover, the adjacent amino acids may interact directly with the antigen (Amit et al., Science, 233:747 (1986), which is incorporated herein by reference) and selecting these amino acids from the donor may be desirable to keep all the antigen contacts that provide affinity in the original antibody.

Residues that "otherwise interact with a CDR region" include those that are determined by secondary structural analysis to be in a spatial orientation sufficient to affect a CDR region. In certain embodiments, residues that "otherwise interact with a CDR region" are identified by analyzing a three-dimensional model of the donor immunoglobulin (e.g., a computer-generated model). A three-dimensional model, typically of the original donor antibody, shows that certain amino acids outside of the CDRs are close to the CDRs and have a good probability of interacting with amino acids in the CDRs by hydrogen bonding, Van der Waals forces, hydrophobic interactions, etc. At those amino acid positions, the donor immunoglobulin amino acid rather than the acceptor immunoglobulin amino acid may be selected. Amino acids according to this criterion will generally have a side chain atom within about 3 angstrom units (A) of some atom in the CDRs and must contain an atom that could interact with the CDR atoms according to established chemical forces, such as those listed above.

In the case of atoms that may form a hydrogen bond, the 3 Angstroms is measured between their nuclei, but for atoms that do not form a bond, the 3 Angstroms is measured between their Van der Waals surfaces. Hence, in the latter case, the nuclei must be within about 6 Angstroms (3 Angstroms plus the sum of the Van der Waals radii) for the atoms to be considered capable of interacting. In many cases the nuclei will be from 4 or 5 to 6 Angstroms apart. In determining whether an amino acid can interact with the CDRs, it is preferred not to consider the last 8 amino acids of heavy chain CDR 2 as part of the CDRs, because from the viewpoint of structure, these 8 amino acids behave more as part of the framework.

Amino acids that are capable of interacting with amino acids in the CDRs, may be identified in yet another way. The solvent accessible surface area of each framework amino acid is calculated in two ways: (1) in the intact antibody, and (2) in a hypothetical molecule consisting of the antibody with its CDRs removed. A significant difference between these numbers of about 10 square angstroms or more shows that access of the framework amino acid to solvent is at least partly blocked by the CDRs, and therefore that the amino acid is making contact with the CDRs. Solvent accessible surface area of an amino acid may be calculated based on a three-dimensional model of an antibody, using algorithms known in the art (e.g., Connolly, J. Appl. Cryst. 16:548 (1983) and Lee and Richards, J. Mol. Biol. 55:379 (1971), both of which are incorporated herein by reference). Framework amino acids may also occasionally interact with the CDRs indirectly, by affecting the conformation of another framework amino acid that in turn contacts the CDRs.

The amino acids at several positions in the framework are known to be capable of interacting with the CDRs in many antibodies (Chothia and Lesk, supra, Chothia et al., supra and Tramontano et al., J. Mol. Biol. 215:175 (1990), all of which are incorporated herein by reference). Notably, the amino acids at positions 2, 48, 64 and 71 of the light chain and 26-30, 71 and 94 of the heavy chain (numbering according to Kabat) are known to be capable of interacting with the CDRs in many antibodies. The amino acids at positions 35 in the light chain and 93 and 103 in the heavy chain are also likely to interact with the CDRs. At all these numbered positions, choice of the donor amino acid rather than the acceptor amino acid (when they differ) to be in the humanized immunoglobulin is preferred. On the other hand, certain residues capable of interacting with the CDR region, such as the first 5 amino acids of the light chain, may sometimes be chosen from the acceptor immunoglobulin without loss of affinity in the humanized immunoglobulin.

Residues which "participate in the VL-VH interface" or "packing residues" include those residues at the interface between VL and VH as defined, for example, by Novotny and Haber, Proc. Natl. Acad. Sci. USA, 82:4592-66 (1985) or Chothia et al, supra. Generally, unusual packing residues should be retained in the humanized antibody if they differ from those in the human frameworks.

In general, one or more of the amino acids fulfilling the above criteria is substituted. In some embodiments, all or most of the amino acids fulfilling the above criteria are substituted. Occasionally, there is some ambiguity about whether a particular amino acid meets the above criteria, and alternative variant immunoglobulins are produced, one of which has that particular substitution, the other of which does not. Alternative variant immunoglobulins so produced can be tested in any of the assays described herein for the desired activity, and the preferred immunoglobulin selected.

Usually the CDR regions in humanized antibodies are substantially identical, and more usually, identical to the corresponding CDR regions of the donor antibody. Although not usually desirable, it is sometimes possible to make one or more conservative amino acid substitutions of CDR residues without appreciably affecting the binding affinity of the resulting humanized immunoglobulin. By conservative substitutions is intended combinations such as gly, ala; val, ile, leu; asp, glu; asn, gln; ser, thr; lys, arg; and phe, tyr.

Additional candidates for substitution are acceptor human framework amino acids that are unusual or "rare" for a human immunoglobulin at that position. These amino acids can be substituted with amino acids from the equivalent position of the mouse donor antibody or from the equivalent positions of more typical human immunoglobulins. For example, substitution may be desirable when the amino acid in a human framework region of the acceptor immunoglobulin is rare for that position and the corresponding amino acid in the donor immunoglobulin is common for that position in human immunoglobulin sequences; or when the amino acid in the acceptor immunoglobulin is rare for that position and the corresponding amino acid in the donor immunoglobulin is also rare, relative to other human sequences. These criteria help ensure that an atypical amino acid in the human framework does not disrupt the antibody structure. Moreover, by replacing an unusual human acceptor amino acid with an amino acid from the donor antibody that happens to be typical for human antibodies, the humanized antibody may be made less immunogenic.

The term "rare", as used herein, indicates an amino acid occurring at that position in less than about 20% but usually less than about 10% of sequences in a representative sample of sequences, and the term "common", as used herein, indicates an amino acid occurring in more than about 25% but usually more than about 50% of sequences in a representative sample. For example, all human light and heavy chain variable region sequences are respectively grouped into "subgroups" of sequences that are especially homologous to each other and have the same amino acids at certain critical positions (Kabat et al., supra). When deciding whether an amino acid in a human acceptor sequence is "rare" or "common" among human sequences, it will often be preferable to consider only those human sequences in the same subgroup as the acceptor sequence.

Additional candidates for substitution are acceptor human framework amino acids that would be identified as part of a CDR region under the alternative definition proposed by Chothia et al., supra. Additional candidates for substitution are acceptor human framework amino acids that would be identified as part of a CDR region under the AbM and/or contact definitions.

Additional candidates for substitution are acceptor framework residues that correspond to a rare or unusual donor framework residue. Rare or unusual donor framework residues are those that are rare or unusual (as defined herein) for murine antibodies at that position. For murine antibodies, the subgroup can be determined according to Kabat and residue positions identified which differ from the consensus. These donor specific differences may point to somatic mutations in the murine sequence which enhance activity. Unusual residues that are predicted to affect binding are retained, whereas residues predicted to be unimportant for binding can be substituted.

Additional candidates for substitution are non-germline residues occurring in an acceptor framework region. For example, when an acceptor antibody chain (i.e., a human antibody chain sharing significant sequence identity with the donor antibody chain) is aligned to a germline antibody chain (likewise sharing significant sequence identity with the donor chain), residues not matching between acceptor chain framework and the germline chain framework can be substituted with corresponding residues from the germline sequence.

Other than the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. Thus, in one embodiment the variable framework region of the humanized immunoglobulin shares at least 85% sequence identity to a human variable framework region sequence or consensus of such sequences. In another embodiment, the variable framework region of the humanized immunoglobulin shares at least 90%, preferably 95%, more preferably 96%, 97%, 98% or 99% sequence identity to a human variable framework region sequence or consensus of such sequences. In general, however, such substitutions are undesirable.

The humanized antibodies preferably exhibit a specific binding affinity for antigen of at least $10^7$, $10^8$, $10^9$ or $10^{10}$ $M^{-1}$. Usually the upper limit of binding affinity of the humanized antibodies for antigen is within a factor of three, four or five of that of the donor immunoglobulin. Often the lower limit of binding affinity is also within a factor of three, four or five of that of donor immunoglobulin. Alternatively, the binding affinity can be compared to that of a humanized antibody having no substitutions (e.g., an antibody having donor CDRs and acceptor FRs, but no FR substitutions). In such instances, the binding of the optimized antibody (with substitutions) is preferably at least two- to three-fold greater, or three- to four-fold greater, than that of the unsubstituted antibody. For making comparisons, activity of the various antibodies can be determined, for example, by BIACORE (i.e., surface plasmon resonance using unlabeled reagents) or competitive binding assays.

Generation of Antibodies Having Modified Sequences

In certain embodiments, provided herein are antibodies comprising heavy and light chain variable region CDRs from an anti-TDRD3 monoclonal antibody (SEQ ID NOs: 4 and 5, respectively), wherein at least one CDR comprises an amino acid substitution, such that the antibody binds to Zika virus EP. In certain embodiments, the heavy chain variable region CDR has an amino acid substitution at position 28, 29, 31, 32, 52, 52A, 53, 54, 55, 100, 100A, 100B, 100C, 100D, 100E, 100F, 100G, 100H, 102, or combination thereof, numbering according to Chothia. In certain embodiments, the amino acid substitution at position 28 is serine. In certain embodiments, the amino acid substitution at position 28 is threonine. In certain embodiments, the amino acid at position 28 is deleted. In certain embodiments, the amino acid substitution at position 29 is phenylalanine. In certain embodiments, the amino acid substitution at position 31 is threonine. In certain embodiments, the amino acid substitution at position 32 is tyrosine. In certain embodiments, the amino acid substitution at position 52 is threonine. In certain embodiments, the amino acid substitution at position 52A is glycine. In certain embodiments, the amino acid substitution at position 53 is glutamic acid. In certain embodiments, the amino acid substitution at position 54 is glycine. In certain embodiments, the amino acid substitution at position 55 is aspartic acid. In certain embodiments, the amino acid at position 99 is deleted. In certain embodiments, the amino acid substitution at position 100 is serine tyrosine. In certain embodiments, the amino acid substitution at position 100A is serine. In certain embodiments, the amino acid substitution at position 100A is threonine. In certain embodiments, the amino acid substitution at position 100B is asparagine. In certain embodiments, the amino acid substitution at position 100C is phenylalanine. In certain embodiments, the amino acid substitution at position 100D is tyrosine. In certain embodiments, the amino acid substitution at position 100E is tyrosine. In certain embodiments, the amino acid substitution at position 100F is tyrosine. In certain embodiments, the amino acid substitution at position 100G is tyrosine. In certain embodiments, the amino acid substitution at position 100H is threonine. In certain embodiments, the amino acid substitution at position 102 is alanine. In certain embodiments, the amino acid substitution at position 102 is valine.

In certain embodiments, the light chain variable region CDR has an amino acid substitution at positions 26, 29, 31, 32, 33, 50, 53, 54, 55, 56, 91, 93, 94, 95, 95B, 96, 97, or combinations thereof, numbering according to Chothia. In certain embodiments, the amino acid substitution at position 26 is threonine. In certain embodiments, the amino acid substitution at position 29 is isoleucine. In certain embodiments, the amino acid substitution at position 31 is valine. In certain embodiments, the amino acid substitution at position 32 is phenylalanine. In certain embodiments, the amino acid substitution at position 33 is leucine. In certain embodiments, the amino acid substitution at position 50 is aspartic acid. In certain embodiments, the amino acid substitution at position 53 is threonine. In certain embodiments, the amino acid substitution at position 54 is arginine. In certain embodiments, the amino acid substitution at position 54 is asparagine. In certain embodiments, the amino acid substitution at position 55 is alanine. In certain embodiments, the amino acid substitution at position 56 is threonine. In certain embodiments, the amino acid substitution at position 91 is arginine. In certain embodiments, the amino acid substitution at position 93 is tyrosine. In certain embodiments, the amino acid substitution at position 94 is asparagine. In certain embodiments, the amino acid substitution at position 95 is tryptophan. In certain embodiments, the amino acid substitution at position 95B is proline. In certain embodiments, the amino acid substitution at position 96 is tyrosine. In certain embodiments, the amino acid substitution at position 97 is serine. In certain embodiments, a proline is added between amino acids at positions 95B and 96.

In certain embodiments, the antibodies described herein comprise heavy and light chain variable region CDRs, wherein heavy chain variable region CDR1 has the amino acid sequence GFX$_1$FSTY (SEQ ID NO: 54), wherein X$_1$ may or may not be present and is selected from serine and threonine; wherein heavy chain variable region CDR2 has the amino acid sequence X$_2$GEGDS (SEQ ID NO: 55), wherein X$_2$ is selected from serine and threonine; and wherein heavy chain variable region CDR3 has the amino acid sequence GYX$_3$NFYYYTMDX$_4$ (SEQ ID NO: 56), wherein X$_3$ is selected from serine and threonine, and X$_4$ is selected from alanine and valine.

In certain embodiments, heavy chain CDR1 has the amino acid sequence GFSFSTY (SEQ ID NO: 21). In certain embodiments, heavy chain CDR1 has the amino acid sequence GFTGSTY (SEQ ID NO: 22). In certain embodiments, heavy chain CDR1 has the amino acid sequence GFFSTY (SEQ ID NO: 23). In certain embodiments, heavy chain CDR2 has the amino acid sequence TGEGDS (SEQ ID NO: 28). In certain embodiments, heavy chain CDR2 has the amino acid sequence SGEGDS (SEQ ID NO: 27). In certain embodiments, heavy chain CDR3 has the amino acid sequence GYSNFYYYTMDA (SEQ ID NO: 32). In certain embodiments, heavy chain CDR3 has the amino acid sequence GYSNFYYYTMDV (SEQ ID NO: 33). In certain embodiments, heavy chain CDR3 has the amino acid sequence GYTNFYYYTMDA (SEQ ID NO: 34).

In certain embodiments, the antibodies described herein comprise heavy and light chain variable region CDRs, wherein light chain variable region CDR1 has the amino acid sequence RAX$_5$QSIX$_6$TFLA (SEQ ID NO: 57), wherein X$_5$ is selected from serine and threonine, and wherein X$_6$ is selected from serine and valine; wherein light chain variable region CDR2 has the amino acid sequence DASTX$_7$AX$_8$ (SEQ ID NO: 58), wherein X$_7$ is selected from arginine and asparagine, and X$_8$ is selected from serine and threonine; and wherein light chain variable region CDR3 has the amino acid sequence QQRYNWPPYX$_9$ (SEQ ID NO: 59), wherein X$_9$ is selected from serine and threonine.

In certain embodiments, light chain CDR1 has the amino acid sequence RATQSISTFLA (SEQ ID NO: 38). In certain embodiments, light chain CDR1 has the amino acid sequence RASQSISTFLA (SEQ ID NO: 39). In certain embodiments, light chain CDR1 has the amino acid sequence RATQSIVTFLA (SEQ ID NO: 40). In certain embodiments, light chain CDR2 has the amino acid sequence DASTRAS (SEQ ID NO: 44). In certain embodiments, light chain CDR2 has the amino acid sequence DASTRAT (SEQ ID NO: 45). In certain embodiments, light chain CDR2 has the amino acid sequence DASTNAS (SEQ ID NO: 46). In certain embodiments, light chain CDR3 has the amino acid sequence QQRYNWPPYS (SEQ ID NO: 50). In certain embodiments, light chain CDR3 has the amino acid sequence QQRYNWPPYT (SEQ ID NO: 51).

In certain embodiments, the anti-Zika virus EP antibodies described herein contain framework mutations in the variable region sequences. In some embodiments, the antibodies described herein comprise heavy and light chain variable region sequences, wherein the heavy chain variable region sequence comprises amino acid substitutions at positions 1, 5, 23, 33, 38, 47, 49, 50, 57, 58, 68, 71, 73, 78, 80, 81, 82B, 82C, 84, 93, 108, or combinations thereof, numbering according to Chothia. In certain embodiments, the amino acid substitution at position 1 is glutamine. In some embodiments, the amino acid substitution at position 5 is leucine. In some embodiments, the amino acid substitution at position 23 is serine. In some embodiments, the amino acid substitution at position 33 is serine. In some embodiments, the amino acid substitution at position 38 is lysine. In some embodiments, the amino acid substitution at position 47 is tyrosine. In some embodiments, the amino acid substitution at position 49 is serine. In some embodiments, the amino acid substitution at position 50 is alanine. In some embodiments, the amino acid substitution at position 57 is alanine. In some embodiments, the amino acid substitution at position 58 is phenylalanine. In some embodiments, the amino acid substitution at position 68 is glutamic acid. In some embodiments, the amino acid substitution at position 71 is arginine. In some embodiments, the amino acid substitution at position 73 is asparagine. In some embodiments, the amino acid substitution at position 78 is leucine. In some embodiments, the amino acid substitution at position 80 is phenylalanine. In some embodiments, the amino acid substitution at position 81 is glutamic acid. In some embodiments, the amino acid substitution at position 82(B) is lysine. In some embodiments, the amino acid substitution at position 82(C) is valine. In some embodiments, the amino acid substitution at position 84 is proline. In some embodiments, the amino acid substitution at position 93 is valine. In some embodiments, the amino acid substitution at position 108 is serine. In some embodiments, the amino acid substitution at position 108 is threonine. In some embodiments, the amino acid substitution at position 108 is methionine.

In certain embodiments, the anti-Zika virus EP antibodies described herein contain framework mutations in the variable region sequences. In some embodiments, the antibodies described herein comprise heavy and light chain variable region sequences, wherein the light chain variable region sequence comprises amino acid substitutions at positions 1, 3, 4, 9, 10, 13, 15, 17, 19, 21, 22, 38, 42, 45, 58, 60, 76, 77, 79, 85, 104, or combinations thereof, numbering according to Chothia. In some embodiments, the amino acid substitution at position 1 is glutamic acid. In some embodiments, the amino acid substitution at position 3 is valine. In some embodiments, the amino acid substitution at position 4 is leucine. In some embodiments, the amino acid substitution at position 9 is alanine. In some embodiments, the amino acid substitution at position 10 is threonine. In some embodiments, the amino acid substitution at position 13 is leucine. In some embodiments, the amino acid substitution at position 15 is proline. In some embodiments, the amino acid substitution at position 17 is glutamic acid. In some embodiments, the amino acid substitution at position 19 is alanine. In some embodiments, the amino acid substitution at position 21 is leucine. In some embodiments, the amino acid substitution at position 22 is serine. In some embodiments, the amino acid substitution at position 38 is histidine. In some embodiments, the amino acid substitution at position 42 is glutamine. In some embodiments, the amino acid substitution at position 45 is arginine. In some embodiments, the amino acid substitution at position 58 is isoleucine. In some embodiments, the amino acid substitution at position 60 is alanine. In some embodiments, the amino acid substitution at position 76 is threonine. In some embodiments, the amino acid substitution at position 77 is arginine. In some embodiments, the amino acid substitution at position 77 is threonine. In some embodiments, the amino acid substitution at position 79 is glutamic acid. In some embodiments, the amino acid substitution at position 85 is valine. In some embodiments, the amino acid substitution at position 104 is leucine.

In another embodiment, the variable region sequences, or portions thereof, of the anti-Zika virus EP antibodies described herein are modified to create structurally related anti-Zika virus EP antibodies that retain binding (i.e., to the same epitope as the unmodified antibody).

Accordingly, in one aspect of the disclosure, the CDR1, 2, and/or 3 regions of the engineered antibodies described above can comprise the exact amino acid sequence(s) as those of antibodies disclosed herein. However, in other aspects of the disclosure, the antibodies comprise derivatives from the exact CDR sequences of the antibodies disclosed herein, still retain the ability of to bind Zika virus EP effectively. Such sequence modifications may include one or more amino acid additions, deletions, or substitutions, e.g., conservative sequence modifications as described above. Sequence modifications may also be based on the consensus sequences described above for the particular CDR1, CDR2, and CDR3 sequences of antibodies disclosed herein.

Accordingly, in another embodiment, the engineered antibody may be composed of one or more CDRs that are, for example, 90%, 95%, 98% or 99.5% identical to one or more CDRs of antibodies disclosed herein. Ranges intermediate to the above-recited values, e.g., CDRs that are 90-95%, 95-98%, or 98-100% identical identity to one or more of the above sequences are also intended to be encompassed by the present disclosure.

In another embodiment, one or more residues of a CDR may be altered to modify binding to achieve a more favored on-rate of binding, a more favored off-rate of binding, or both, such that an idealized binding constant is achieved. Using this strategy, an antibody having ultra-high binding affinity of, for example, $10^{10}$ M$^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Thus, for variable region modification within the VH and/or VL CDR1, CDR2 and/or CDR3 regions, site-directed mutagenesis or PCR-mediated mutagenesis can be performed to introduce the mutation(s) and the effect on antibody binding, or other functional property of interest, can be evaluated in in vitro or in vivo assays. Preferably conservative modifications (as discussed herein) are introduced. The mutations can be amino acid substitutions, additions or deletions, but are preferably substitutions. Moreover, typically no more than one, two, three, four or five residues within a CDR region are altered.

In general, the framework regions of antibodies are usually substantially identical, and more usually, identical to the framework regions of the human germline sequences from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting immunoglobulin. Thus, in one embodiment the variable framework region of the antibody shares at least 85% sequence identity to a human germline variable framework region sequence or consensus of such sequences. In another embodiment, the variable framework region of the antibody shares at least 90%, 95%, 96%, 97%, 98% or 99% sequence identity to a human germline variable framework region sequence or consensus of such sequences.

Framework modifications can also be made to reduce immunogenicity of the antibody or to reduce or remove T cell epitopes that reside therein, as described for instance by Carr et al in US2003/0153043.

Engineered antibodies of the disclosure include those in which modifications have been made to framework residues within $V_H$ and/or $V_L$, e.g. to improve the properties of the antibody. Typically such framework modifications are made to decrease the immunogenicity of the antibody. For example, one approach is to "back-mutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, *Nature* 332:323-327; Jones, P. et al., 1986, *Nature* 321:522-525; and Queen, C. et al., 1989, *Proc. Natl. Acad. See. U.S.A.* 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, *J. Biol. Chem.* 266: 19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of a heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors were constructed so that PCR amplified V heavy and V kappa light chain cDNA sequences could be used to reconstruct complete heavy and light chain minigenes. These plasmids can be used to express completely human IgG$_1$κ or IgG$_4$κ antibodies.

Fully human, humanized, and chimeric antibodies described herein also include IgG2, IgG3, IgE, IgA, IgM, and IgD antibodies. Similar plasmids can be constructed for expression of other heavy chain isotypes, or for expression of antibodies comprising lambda light chains.

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 20, 26 and 31; and (2) light chain framework regions and light chain CDRs, where at least one of the light chain CDRs includes an amino acid sequence selected from the amino acid sequences of CDRs shown in SEQ ID NOs: 38, 44 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 22, 28 and 33; and (2) light chain framework regions and light chain CDRs, where at least one of the light chain CDRs includes an amino acid sequence selected from the amino acid sequences of CDRs shown in SEQ ID NOs: 39, 45 and 51; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 20, 26 and 31; and (2) light chain framework regions and light chain CDRs, where at least one of the light chain CDRs includes an amino acid sequence selected from the amino acid sequences of CDRs shown in SEQ ID NOs: 39, 45 and 51; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 20, 26 and 31; and (2) light chain framework regions and light chain CDRs, where at least one of the light chain CDRs includes an amino acid sequence selected from the amino acid sequences of CDRs shown in SEQ ID NOs: 40, 46 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 28 and 32; and (2) light chain framework regions and light chain CDRs, where at least one of the light chain CDRs includes an amino acid sequence selected from the amino acid sequences of CDRs shown in SEQ ID NOs: 38, 44 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 27 and 32; and (2) light chain framework regions and light chain CDRs, where at least one of the light chain CDRs includes an amino acid sequence selected from the amino acid sequences of CDRs shown in SEQ ID NOs: 40, 46 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 27 and 32; and (2) light chain framework regions and light chain CDRs, where at least one of the light chain CDRs includes an amino acid sequence selected from the amino acid sequences of CDRs shown in SEQ ID NOs: 38, 44 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 27 and 32; and (2) light chain framework regions and light chain CDRs, where at least one of the light chain CDRs includes an amino acid sequence selected from the amino acid sequences of CDRs shown in SEQ ID NOs: 37, 43 and 49; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 28 and 32; and (2) light chain framework regions and light chain CDRs, where at least one of the light chain CDRs includes an amino acid sequence selected from the amino acid sequences of CDRs shown in SEQ ID NOs: 37, 43 and 49; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 22, 28 and 33; and (2) light chain framework regions and light chain CDRs, where at least one of the light chain CDRs includes an amino acid sequence selected from the amino acid sequences of CDRs shown in SEQ ID NOs: 37, 43 and 49; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 23, 28 and 34; and (2) light chain framework regions and light chain CDRs, where at least one of the light chain CDRs includes an amino acid sequence selected from the amino acid sequences of CDRs shown in SEQ ID NOs: 37, 43 and 49; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 28 and 34; and (2) light chain framework regions and light chain CDRs, where at least one of the light chain CDRs includes an amino acid sequence selected from the amino acid sequences of CDRs shown in SEQ ID NOs: 37, 43 and 49; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 27 and 32; and (2) light chain framework regions and light chain CDRs, where at least one of the light chain CDRs includes an amino acid sequence selected from the amino acid sequences of CDRs shown in SEQ ID NOs: 39, 45 and 51; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 28 and 32; and (2) light chain framework regions and light chain CDRs, where at least one of the light chain CDRs includes an amino acid sequence selected from the amino acid sequences of CDRs shown in SEQ ID NOs: 39, 45 and 51; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 28 and 32; and (2) light chain framework regions and light chain CDRs, where at least one of the light chain CDRs includes an amino acid sequence selected from the amino acid sequences of CDRs shown in SEQ ID NOs: 40, 46 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 22, 28 and 33; and (2) light chain framework regions and light chain CDRs, where at least one of the light chain CDRs includes an amino acid sequence selected from the amino acid sequences of CDRs shown in SEQ ID NOs: 38, 44 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 22, 28 and 33; and (2) light chain framework regions and light chain CDRs, where at least one of the light chain CDRs includes an amino acid sequence selected from the amino acid sequences of CDRs shown in SEQ ID NOs: 40, 46 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 23, 28 and 34; and (2) light chain framework regions and light chain CDRs, where at least one of the light chain CDRs includes an amino acid sequence selected from the amino acid sequences of CDRs shown in SEQ ID NOs: 38, 44 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 23, 28 and 34; and (2) light chain framework regions and light chain CDRs, where at least one of the light chain CDRs includes an amino acid sequence selected from the amino acid sequences of CDRs shown in SEQ ID NOs: 40, 46 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 28 and 34; and (2) light chain framework regions and light chain CDRs, where at least one of the light chain CDRs includes an amino acid sequence selected from the amino acid sequences of CDRs shown in SEQ ID NOs: 38, 44 and 50; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 28 and 34; and (2) light chain framework regions and light chain CDRs, where at least one of the light chain CDRs includes an amino acid sequence selected from the amino acid sequences of CDRs shown in SEQ ID NOs: 39, 45 and 51; where the antibody binds to Zika virus EP. The ability of the antibody to bind Zika virus EP can be determined using standard binding assays (e.g., an ELISA or a FLISA).

In certain embodiments, methods for preparing an anti-Zika virus EP antibody are provided, including: preparing an antibody including (1) heavy chain framework regions and heavy chain CDRs, where at least one of the heavy chain CDRs includes an amino acid sequence selected from the amino acid sequences of CDRs shown in SEQ ID NOs: 21, 28 and 34; and (2) light chain framework regions and light chain CDRs, where at least one of the light chain CDRs includes an amino acid sequence selected from the amino acid sequences of CDRs shown in SEQ ID NOs: 40, 46 and 50; where the antibody binds to Zika virus EP. The ability of the antibody to bind Zika virus EP can be determined using standard binding assays (e.g., an ELISA or a FLISA).

Additional Antibody Modifications

Antibodies of the present disclosure can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al. (2000) Mol Immunol 37:697-706). Glycosylation has been known to occur at motifs containing an N-X-S/T sequence. In some instances, it is preferred to have an anti-Zika virus antibody that does not contain variable region glycosylation. This can be achieved either by selecting antibodies that do not contain the glycosylation motif in the variable region or by mutating residues within the glycosylation region.

For example, in certain embodiments, the glycosylation of an antibody is modified, e.g., the variable region is altered to eliminate one or more glycosylation sites resident in the variable region. More particularly, it is desirable in the sequence of the present antibodies to eliminate sites prone to glycosylation. This is achieved by altering the occurrence of one or more N-X-(S/T) sequences that occur in the parent variable region (where X is any amino acid residue), particularly by substituting the N residue and/or the S or T residue. In one embodiment, T95 is mutated to K95. In another embodiment, N47 is mutated to R47.

For example, aglycoslated antibodies can be made (i.e., which lack glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, the antibody can have an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, the cell lines Ms704, Ms705, and Ms709 lack the fucosyltransferase gene, FUT8 (α (1,6)-fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) Biotechnol Bioeng 82:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al. (2002) J. Biol. Chem. 277:26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. Patent application corresponding to Alston & Bird LLP, filed on Aug. 11, 2006. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). Alternatively, the fucose residues of the antibody can be cleaved off using a fucosidase enzyme; e.g., the fucosidase α-L-fucosidase removes fucosyl residues from antibodies (Tarentino et al. (1975) Biochem. 14:5516-23).

The variable segments of antibodies produced as described supra (e.g., the heavy and light chain variable regions of chimeric or humanized antibodies) are typically linked to at least a portion of an immunoglobulin constant region (Fc region), typically that of a human immunoglobulin. Human constant region DNA sequences can be isolated in accordance with well-known procedures from a variety of human cells, but preferably immortalized B cells (see Kabat et al., supra, and Liu et al., WO87/02671) (each of which is incorporated by reference in its entirety for all purposes). Ordinarily, the antibody will contain both light chain and heavy chain constant regions. The heavy chain constant region usually includes CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. When it is desired that the antibody (e.g., humanized antibody) exhibit cytotoxic activity, the constant domain is usually a complement fixing constant domain and the class is typically IgG1. Human isotype IgG1 is preferred. Light chain constant regions can be lambda or kappa. The humanized antibody may comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In certain embodiments, the antibody comprises a variable region that is mutated to improve the physical stability of the antibody. In one embodiment, the antibody is an IgG4 isotype antibody comprising a serine to proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system). For example, in certain embodiments, an anti-Zika virus EP antibody described herein can comprise the heavy chain variable region of any of the antibodies described herein linked to a human IgG4 constant region in which the Serine at a position corresponding to position 241 as described in Angal et al., supra, has been mutated to Proline. Thus, for the heavy chain variable regions linked to a human IgG4 constant region, this mutation corresponds to an S228P mutation by the EU index.

In certain embodiments, the hinge region of CH1 is modified such that the number of cysteine residues in the hinge region is altered, e.g., increased or decreased. This approach is described further in U.S. Pat. No. 5,677,425. The number of cysteine residues in the hinge region of CH1 is altered to, for example, facilitate assembly of the light and heavy chains or to increase or decrease the stability of the antibody.

In addition, the antibody can be pegylated, for example, to increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See, e.g., EP 0 154 316 and EP 0 401 384.

Immunizations

To generate fully human antibodies to Zika virus EP, transgenic or transchromosomal mice containing human immunoglobulin genes (e.g., HCo12, HCo7 or KM mice) can be immunized with a purified or enriched preparation of the Zika virus EP antigen and/or cells expressing Zika virus EP, as described, for example, by Lonberg et al. (1994) *Nature* 368(6474): 856-859; Fishwild et al. (1996) *Nature Biotechnology* 14: 845-851 and WO 98/24884. As described herein, HuMAb mice are immunized either with recombinant Zika virus EP proteins or cell lines expressing Zika virus EP as immunogens. Alternatively, mice can be immunized with DNA encoding Zika virus EP. Preferably, the mice will be 6-16 weeks of age upon the first infusion. For example, a purified or enriched preparation (5-50 µg) of the recombinant Zika virus EP antigen can be used to immunize the HuMAb mice intraperitoneally.

Cumulative experience with various antigens has shown that the HuMAb transgenic mice respond best when initially immunized intraperitoneally (IP) or subcutaneously (SC) with antigen in complete Freund's adjuvant, followed by every other week IP/SC immunizations (up to a total of 10) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-Zika virus EP human immunoglobulin can be used for fusions. Mice can be boosted intravenously with antigen 3 days before sacrifice and removal of the spleen.

Generation of Hybridomas Producing Monoclonal Antibodies to Zika Virus EP

To generate hybridomas producing monoclonal antibodies to Zika virus EP, splenocytes and lymph node cells from immunized mice can be isolated and fused to an appropriate immortalized cell line, such as a mouse myeloma cell line. The resulting hybridomas can then be screened for the production of antigen-specific antibodies. For example, single cell suspensions of splenic lymphocytes from immunized mice can be fused to SP2/0-Ag8.653 nonsecreting mouse myeloma cells (ATCC, CRL 1580) with 50% PEG (w/v). Cells can be plated at approximately $1 \times 10^5$ in flat bottom microtiter plate, followed by a two week incubation in selective medium containing besides usual reagents 10% fetal Clone Serum, 5-10% origen hybridoma cloning factor (IGEN) and 1×HAT (Sigma). After approximately two weeks, cells can be cultured in medium in which the HAT is replaced with HT. Individual wells can then be screened by ELISA for human anti-Zika virus EP monoclonal IgM and IgG antibodies. Once extensive hybridoma growth occurs, medium can be observed usually after 10-14 days. The antibody secreting hybridomas can be replated, screened again, and if still positive for IgG, anti-Zika virus EP monoclonal antibodies can be subcloned at least twice by limiting dilution. The stable subclones can then be cultured in vitro to generate antibody in tissue culture medium for characterization.

Generation of Transfectomas Producing Monoclonal Antibodies to Zika Virus EP

Antibodies described herein also can be produced in a host cell transfectoma using, for example, a combination of recombinant DNA techniques and gene transfection methods as is well known in the art (Morrison, S. (1985) *Science* 229:1202).

For example, in certain embodiments, the gene(s) of interest, e.g., human antibody genes, can be ligated into an expression vector such as a eukaryotic expression plasmid such as used by GS gene expression system disclosed in WO 87/04462, WO 89/01036 and EP 338 841 or other expression systems well known in the art. The purified plasmid with the cloned antibody genes can be introduced in eukaryotic host cells such as CHO-cells or NSO-cells or alternatively other eukaryotic cells like a plant derived cells, fungi or yeast cells. The method used to introduce these genes could be methods described in the art such as electroporation, lipofectine, lipofectamine or other. After introducing these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively these cloned antibody genes can be expressed in other expression systems such as *E. coli* or in complete organisms or can be synthetically expressed.

Expression of Recombinant Antibodies

Chimeric and humanized antibodies are typically produced by recombinant expression. Nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al., U.S. Pat. No. 4,704,362).

E. coli is one prokaryotic host particularly useful for cloning the polynucleotides (e.g., DNA sequences) described herein. Other microbial hosts suitable for use include bacilli, such as Bacillus subtilis, and other enterobacteriaceae, such as Salmonella, Serratia, and various Pseudomonas species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation. Other microbes, such as yeast, are also useful for expression.

Saccharomyces is a preferred yeast host, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian tissue cell culture may also be used to express and produce the polypeptides of described herein (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, preferably, myeloma cell lines, or transformed B-cells or hybridomas. Preferably, the cells are nonhuman. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., J. Immunol. 148:1149 (1992).

Alternatively, antibody-coding sequences can be incorporated in transgenes for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., Molecular Cloning: A Laboratory Manual (Cold Spring Harbor Press, 2nd ed., 1989) (incorporated by reference in its entirety for all purposes). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present disclosure can be purified according to standard procedures of the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

Antibody Fragments

Also contemplated within the scope of the instant disclosure are antibody fragments. In one embodiment, fragments of non-human, and/or chimeric antibodies are provided. In another embodiment, fragments of humanized antibodies are provided. Typically, these fragments exhibit specific binding to antigen with an affinity of at least $10^7$, and more typically $10^8$ or $10^9 M^{-1}$. Humanized antibody fragments include separate heavy chains, light chains, Fab, Fab', F(ab')2, Fabc, and Fv. Fragments are produced by recombinant DNA techniques, or by enzymatic or chemical separation of intact immunoglobulins.

Assays for Characterization of Antibodies

Antibodies described herein can be tested for binding to Zika virus envelope protein (EP) by, for example, standard ELISA. Briefly, serial dilutions of Zika virus envelope protein, or Zika virus itself, is mixed with antibodies described herein. These mixtures are incubated overnight at room temperature to allow equilibrium to be reached. An indirect ELISA is used to measure the concentration of unbound and singly bound antibody. Alternatively, microtiter plates are coated with purified Zika virus and then blocked with 5% nonfat dry milk in PBS. After washing, purified antibodies described herein are added to wells containing antigen and incubated for 2 hours at room temperature. Bound antibodies are detected using horseradish peroxidase conjugated anti-mouse IgG secondary antibodies and ABTS substrate (Kirkegaard and Perry Laboratories).

In some embodiments, the antibodies described herein bind Zika virus EP with a Kd value between 3 and 25 µg/mL as determined by ELISA. In some embodiments, the antibodies described herein bind Zika virus EP with a Kd value of at least 3 µg/mL as determined by ELISA. In some embodiments, the antibodies described herein bind Zika virus EP with a Kd value of at least 5 µg/mL as determined by ELISA. In some embodiments, the antibodies described herein bind Zika virus EP with a Kd value of at least 10 µg/mL as determined by ELISA. In some embodiments, the antibodies described herein bind Zika virus EP with a Kd value of at least 15 µg/mL as determined by ELISA. In some embodiments, the antibodies described herein bind Zika virus EP with a Kd value of at least 20 µg/mL as determined by ELISA. In some embodiments, the antibodies described herein bind Zika virus EP with a Kd value of at least 25 µg/mL as determined by ELISA.

An ELISA assay as described above can be used to screen for antibodies and, thus, hybridomas that produce antibodies that show positive reactivity with the Zika virus EP. Hybridomas that produce antibodies that bind, preferably with high affinity, to Zika virus EP can then be subcloned and further characterized. One clone from each hybridoma, which retains the reactivity of the parent cells (by ELISA), can then be chosen for making a cell bank, and for antibody purification.

The ELISA assay described above can also be used to confirm that framework mutation(s) do not affect the ability of the anti-EP antibodies disclosed herein to bind to EP.

To purify anti-Zika virus EP antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected anti-Zika virus EP monoclonal antibodies bind to unique epitopes, each antibody can be biotinylated using commercially available reagents (Pierce, Rockford, Ill.). Biotinylated MAb binding can be detected with a streptavidin labeled probe. Competition studies using unlabeled monoclonal antibodies and biotinylated monoclonal antibodies can be performed using Zika virus EP coated-ELISA plates as described above.

To determine the isotype of purified antibodies, isotype ELISAs can be performed using reagents specific for antibodies of a particular isotype. For example, plates are coated with anti-IgG, IgA, or IgM heavy-chain specific antibodies (100 ng/well) and incubated with hybridoma culture supernatants. The subtype of the mAb is detected by using anti-IgG1, IgG2a, IgG2b, IgG3, IgM, or IgA heavy-chain specific antibodies conjugated to alkaline phosphatase.

Anti-Zika virus EP antibodies can be further tested for reactivity with the Zika virus EP antigen by Western blotting. Briefly, unlabeled Zika virus EP is resolved on a 10% SDS-polyacrylaminde gel and transferred to PVDF membranes. After nonspecific bindings sites are blocked using nonfat dry milk in PBS containing 0.02% Tween-20, purified mAb (10 ug/ml) are added to the membranes for 1 hour at room temperature. Membranes are then incubated with horseradish peroxidase-conjugated goat anti-mouse IgA+IgG+IgM secondary antibodies for 1 hour and developed using ECL chemiluminescence kit (Amersham).

Methods for analyzing binding affinity, cross-reactivity, and binding kinetics of various anti-Zika virus EP antibodies include standard assays known in the art, for example, Biacore™ surface plasmon resonance (SPR) analysis using a Biacore™ 2000 SPR instrument (Biacore AB, Uppsala, Sweden).

To determine the neutralization of antibodies described herein, in vitro plaque reduction neutralization (PRNT) assays can be done. Briefly, plaque assays are done using confluent BHK-21 cells. Two-fold serial dilutions of antibodies described herein are mixed with 50 PFU of Zika virus at 37° C. for 1 hour. The mixture is applied to cell monoloayers and incubated for 4-7 days. Infection is quantified by 4G2 immunostaining followed by TMB peroxidase substrate (KPL) and absorbance is measured in a plate reader. 100% infection corresponds to the average OD600 in wells not exposed to antibody. In some embodiments, the output of the PRNT assay is PRNT50 (concentration of antibody that reduces plaque formation by 50%). In some embodiments, the antibodies described herein have a PRNT50 value of at least 0.03 µg/mL.

In some embodiments, anti-Zika virus EP antibodies reduce antibody-dependent enhancement (ADE) of infection. ADE is a phenomenon that has been proposed to mediate increased disease severity when infection occurs in a background of preexisting enhancing antibodies. Mechanistically, this occurs when enhancing antibodies bind the mature as well as immature virus particles and mediate virus entry via antibody engagement of Fcγ receptors present on host cells. Several FLE-directed antibodies have been described in literature including 4G2, E53, and the E-dimer epitope (EDE) directed mAbs (Dejnirattisai W, et al., 2015). Several studies have shown that when DENV is opsonized with antibody levels that are phagocytosed by Fcγ receptors, only antibodies that are able to inhibit virus fusion with phagosomal membranes will prevent infection and thus ADE (Chan K R et al., 2011, Wu R et al, 2012). Accordingly, in some embodiments, the ability of the anti-Zika virus EP antibodies described herein to engage the Zika virus FLE epitope at the E-dimer interface, results in reduction of ADE activity by fusion inhibition.

In some embodiments, reduction of ADE is tested by using cells that express leukocyte immunoglobulin like receptor B1 (LILRB1) and are thus highly susceptible to ADE. A non-limiting example of such cells is THP1.2S monocytes. Cells are incubated with an anti-Zika virus antibody described herein prior to infection. Virus replication is then measured by plaque assay using cells susceptible to viral infection. A non-limiting example of such cells is BHK21 cells. Plaque titers are then measured, and a reduction in plaque titers compared to a control indicates the anti-Zika virus EP antibody tested is effective in reducing ADE. Other methods of measuring ADE are known in the art and can be used to determine the effect of an anti-Zika virus EP antibody described herein on ADE.

Competitive Binding Antibodies

In certain embodiments, antibodies described herein compete (e.g., cross-compete) for binding to Zika virus EP with the particular anti-Zika virus EP antibodies described herein. Such competing antibodies can be identified based on their ability to competitively inhibit binding to Zika virus EP of one or more of mAbs described herein in standard Zika virus EP binding assays. For example, standard ELISA assays can be used in which a recombinant Zika virus EP is immobilized on the plate, one of the antibodies is fluorescently labeled and the ability of non-labeled antibodies to compete off the binding of the labeled antibody is evaluated. Additionally or alternatively, BIAcore analysis can be used to assess the ability of the antibodies to cross-compete. The ability of a test antibody to inhibit the binding of an anti-EP antibody described herein to Zika virus EP demonstrates that the test antibody can compete with the antibody for binding to Zika virus EP.

In certain embodiments, the competing antibody is an antibody that binds to the same epitope on Zika virus EP as the particular anti-EP monoclonal antibodies described herein. Standard epitope mapping techniques, such as x-ray crystallography and 2-dimensional nuclear magnetic resonance, can be used to determine whether an antibody binds to the same epitope as a reference antibody (see, e.g., Epitope Mapping Protocols in Methods in Molecular Biology, Vol. 66, G. E. Morris, Ed. (1996)).

In certain embodiments, the antibody that competes for binding to Zika virus EP and/or binds to the same epitope on Zika virus EP is a humanized antibody.

In some embodiments, the anti-Zika virus antibodies described herein bind an epitope on the fusion loop comprising residues D98, R99 and W101 (SEQ ID NO: 3). In some embodiments, the antibody that competes for binding to Zika virus EP binds the epitope on the fusion loop comprising residues D98, R99 and W101 (SEQ ID NO: 3).

Once a single, archtypal anti-EP mAb has been isolated that has the desired properties described herein, it is straightforward to generate other mAbs with similar properties, e.g., having the same epitope, by using art-known methods. For example, mice may be immunized with Zika virus as described herein, hybridomas produced, and the resulting mAbs screened for the ability to compete with the archtypal mAb for binding to Zika virus EP. Mice can also be immunized with a smaller fragment of Zika virus EP containing the epitope to which the archtypal mAb binds. The epitope can be localized by, e.g., screening for binding to a series of overlapping peptides spanning Zika virus EP. Alternatively, the method of Jespers et al., Biotechnology 12:899, 1994 may be used to guide the selection of mAbs having the same epitope and therefore similar properties to the archtypal mAb. Using phage display, first the heavy chain of the archtypal antibody is paired with a repertoire of (preferably human) light chains to select an Zika virus EP-binding mAb, and then the new light chain is paired with a repertoire of (preferably human) heavy chains to select an (preferably human) Zika virus EP-binding mAb having the same epitope as the archtypal mAb. Alternatively variants of the archetypal mAb can be obtained by mutagenesis of cDNA encoding the heavy and light chains of the antibody.

Epitope mapping, e.g., as described in Champe et al. (1995) J. Biol. Chem. 270:1388-1394, can be performed to determine whether the antibody binds an epitope of interest. "Alanine scanning mutagenesis," as described by Cunningham and Wells (1989) Science 244: 1081-1085, or some other form of point mutagenesis of amino acid residues in human Zika virus EP may also be used to determine the functional epitope for an anti-EP antibody described herein. Mutagenesis studies, however, may also reveal amino acid residues that are crucial to the overall three-dimensional structure of Zika virus EP but that are not directly involved in antibody-antigen contacts, and thus other methods may be necessary to confirm a functional epitope determined using this method.

The epitope bound by a specific antibody may also be determined by assessing binding of the antibody to peptides comprising fragments of Zika virus EP. A series of overlapping peptides encompassing the sequence of Zika virus EP may be synthesized and screened for binding, e.g. in a direct ELISA, a competitive ELISA (where the peptide is assessed for its ability to prevent binding of an antibody to Zika virus EP bound to a well of a microtiter plate), or on a chip. Such peptide screening methods may not be capable of detecting some discontinuous functional epitopes, i.e. functional epitopes that involve amino acid residues that are not contiguous along the primary sequence of the Zika virus EP polypeptide chain.

The epitope bound by antibodies described herein may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in Zika virus EP when free and when bound in a complex with an antibody of interest (Zinn-Justin et al. (1992) Biochemistry 31, 11335-11347; Zinn-Justin et al. (1993) Biochemistry 32, 6884-6891).

With regard to X-ray crystallography, crystallization may be accomplished using any of the known methods in the art (e.g. Giege et al. (1994) Acta Crystallogr. D50:339-350; McPherson (1990) Eur. J. Biochem. 189:1-23), including microbatch (e.g. Chayen (1997) Structure 5:1269-1274), hanging-drop vapor diffusion (e.g. McPherson (1976) J. Biol. Chem. 251:6300-6303), seeding and dialysis. It is desirable to use a protein preparation having a concentration of at least about 1 mg/mL and preferably about 10 mg/mL to about 20 mg/mL. Crystallization may be best achieved in a precipitant solution containing polyethylene glycol 1000-20,000 (PEG; average molecular weight ranging from about 1000 to about 20,000 Da), preferably about 5000 to about 7000 Da, more preferably about 6000 Da, with concentrations ranging from about 10% to about 30% (w/v). It may also be desirable to include a protein stabilizing agent, e.g. glycerol at a concentration ranging from about 0.5% to about 20%. A suitable salt, such as sodium chloride, lithium chloride or sodium citrate may also be desirable in the precipitant solution, preferably in a concentration ranging from about 1 mM to about 1000 mM. The precipitant is preferably buffered to a pH of from about 3.0 to about 5.0, preferably about 4.0. Specific buffers useful in the precipitant solution may vary and are well-known in the art (Scopes, Protein Purification: Principles and Practice, Third ed., (1994) Springer-Verlag, New York). Examples of useful buffers include, but are not limited to, HEPES, Tris, MES and acetate. Crystals may be grow at a wide range of temperatures, including 2° C., 4° C., 8° C. and 26° C.

Antibody:antigen crystals may be studied using well-known X-ray diffraction techniques and may be refined using computer software such as X-PLOR (Yale University, 1992, distributed by Molecular Simulations, Inc.; see e.g. Blundell & Johnson (1985) Meth. Enzymol. 114 & 115, H. W. Wyckoff et al., eds., Academic Press; U.S. Patent Application Publication No. 2004/0014194), and BUSTER (Bricogne (1993) Acta Cryst. D49:37-60; Bricogne (1997) Meth. Enzymol. 276A:361-423, Carter & Sweet, eds.; Roversi et al. (2000) Acta Cryst. D56:1313-1323), the disclosures of which are hereby incorporated by reference in their entireties.

Antibody competition assays, as described herein, can be used to determine whether an antibody "binds to the same epitope" as another antibody. Typically, competition of 50% or more, 60% or more, 70% or more, such as 70%, 71%, 72%, 73%, 74%, 75%, 80%, 85%, 90%, 95% or more, of an antibody known to interact with the epitope by a second antibody under conditions in which the second antibody is in excess and the first saturates all sites, is indicative that the antibodies "bind to the same epitope." To assess the level of competition between two antibodies, for example, radioimmunoassays or assays using other labels for the antibodies, can be used. For example, a Zika virus EP antigen can be incubated with a saturating amount of a first anti-EP antibody or antigen-binding fragment thereof conjugated to a labeled compound (e.g., $^3$H, $^{125}$I, biotin, or rubidium) in the presence the same amount of a second unlabeled anti-EP antibody. The amount of labeled antibody that is bound to the antigen in the presence of the unlabeled blocking antibody is then assessed and compared to binding in the absence of the unlabeled blocking antibody. Competition is determined by the percentage change in binding signals in the presence of the unlabeled blocking antibody compared to the absence of the blocking antibody. Thus, if there is a 50% inhibition of binding of the labeled antibody in the presence of the blocking antibody compared to binding in the absence of the blocking antibody, then there is competition between the two antibodies of 50%. Thus, reference to competition between a first and second antibody of 50% or more, 60% or more, 70% or more, such as 70%, 71%, 72%, 73%, 74%, 75%, 80%, 85%, 90%, 95% or more, means that the first antibody inhibits binding of the second antibody (or vice versa) to the antigen by 50%, 60%, 70%, 71%, 72%, 73%, 74%, 75%, 80%, 85%, 90%, 95% or more (compared to binding of the antigen by the second antibody in the absence of the first antibody). Thus, inhibition of binding of a first antibody to an antigen by a second antibody of 50%, 60%, 70%, 71%, 72%, 73%, 74%, 75%, 80%, 85%, 90%, 95% or more indicates that the two antibodies bind to the same epitope.

Testing Antibodies for Therapeutic Efficacy in Animal Models

Animal models are effective for testing the therapeutic efficacy of antibodies against Zika virus EP. In certain embodiments, rodents (i.e., mice) can be used for Zika infection. Briefly, mice are challenged with a strain of mouse adapted Zika virus (e.g., H/PF/2013 (French Polynesia 2013)) by intraperitoneal inoculation, approximately 300 times the dose lethal for 50% of adult mice. In certain embodiments, guinea pigs can be used for Zika infection. Guinea pigs are challenged with guinea pig-adapted virus. Additionally, in certain embodiments, non-human primates are used as an animal model of infection. In all animal models, antibodies can be administered 24 or 48 hours after infection to test for therapeutic efficacy. In some embodiments, antibodies are administered 24 or 48 hours before infection to test for prophylactic efficacy.

Efficacy of the antibodies to prevent or treat Zika virus is determined by analyzing the mortality rate, viral load, and/or body weight of the animals over time. In some embodiments, untreated animals infected with Zika virus die within 10-11 days post infection. In some embodiments, animals treated with the anti-Zika antibodies described herein before or after Zika virus infection, live significantly longer compared to untreated animals. In some embodiments, animals treated with the anti-Zika antibodies described herein before or after Zika virus infection, live up to 22 days. In some embodiments, animals treated with the anti-Zika antibodies described herein before or after Zika virus infection, maintain body weight over time compared to untreated animals. In some embodiments, animals treated with the anti-Zika antibodies described herein before or after Zika virus infection, have a reduced viral load compared to untreated animals.

In some embodiments, animal models (e.g., mice) are used to determine the efficacy of an anti-Zika virus EP antibody in treating or preventing vertical infection and fetal mortality in pregnancy. In some embodiments, animal models are used to determine the efficacy of an anti-Zika virus EP antibody in reducing or reducing the risk of vertical infection and fetal mortality in pregnancy. In some embodiments, pregnant animals are infected with an adapted Zika virus (e.g., H/PF/2013 for mice) intravenously. Anti-Zika virus EP antibodies described herein are administered before or after infection to test for therapeutic or prophylactic efficacy, respectively. In some embodiments, the efficacy of the antibodies is determined by measuring the viral load in the mother, fetus and placenta, along with determining the fetus survival rate. In some embodiments, mothers treated with the anti-Zika antibodies described herein have a reduced viral load. In some embodiments, fetuses from mothers treated with the anti-Zika antibodies described herein have a higher survival rate and reduced viral load. In some embodiments, the higher survival rate of fetuses is measured as reduction in percent lethality. In some embodiments, the placenta from mothers treated with the anti-Zika antibodies described herein has a reduced viral load. In some embodiments, fetuses from mothers treated with the anti-Zika virus antibodies described herein have normal embryo development. In some embodiments, fetuses from mothers treated with the anti-Zika virus antibodies described herein have normal embryo development, compared to untreated mothers. In some embodiments, the fetuses from untreated mothers are dead (i.e., 100% lethality).

Immunotoxins, Immunoconjugates and Antibody Derivatives

In another embodiment, the antibodies described herein are linked to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells.

Techniques for conjugating such therapeutic moiety to antibodies are well known in the art.

The toxin component of the immunotoxin can be, for example, a chemotherapeutic agent, a toxin such as an enzymatically active toxin of bacterial, fungal, plant or animal origin, or fragments thereof, or a small molecule toxin.

Additional toxins and fragments thereof which can be used include diphtheria A chain, nonbonding active fragments of diphtheria toxin, cholera toxin, botulinus toxin, exotoxin A chain (from *Pseudomonas aeruginosa*), ricin A chain, abrin A chain, modeccin A chain, alpha-sarcin, *Aleurites fordii* proteins, dianthin proteins, *phytolaca Americana* proteins (PAPI, PAPIL, and PAP-S), *Momordica charantia* inhibitor, curcin, crotin, *sapaonaria, officinalis* inhibitor, gelonin, saporin, mitogellin, restrictocin, phenomycin, enomycin, and the tricothcenes. Small molecule toxins include, for example, calicheamicins, maytansinoids, palytoxin and CC1065.

Antibodies described herein also can be used for diagnostic purposes, including sample testing and in vivo imaging, and for this purpose the antibody (or binding fragment thereof) can be conjugated to an appropriate detectable agent, to form an immunoconjugate. For diagnostic purposes, appropriate agents are detectable labels that include radioisotopes, for whole body imaging, and radioisotopes, enzymes, fluorescent labels and other suitable antibody tags for sample testing.

For Zika virus EP detection, the detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, luminescent markers, phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3,2'-(5'-chloro)tricyclo{3.3.1.1 3,7}decan}-4-yl) phenyl phosphate (CSPD), as well as CDP and CDP-Star® or other luminescent substrates well-known to those in the art, for example the chelates of suitable lanthanides such as Terbium(III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Compositions

In certain embodiments, a composition, e.g., a composition, containing one or more monoclonal antibodies described herein, formulated together with a carrier (e.g., a pharmaceutically acceptable carrier), is provided. In some embodiments, the compositions include a combination of multiple (e.g., two or more) isolated antibodies described herein. Preferably, each of the antibodies of the composition binds to a distinct, pre-selected epitope of Zika virus EP.

Pharmaceutical compositions described herein also can be administered in combination therapy, i.e., combined with other agents. For example, the combination therapy can include a composition described herein with at least one or more additional therapeutic agents. Co-administration with other antibodies is also encompassed by the disclosure.

As used herein, the terms "carrier" and "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, e.g., antibody, may be coated in a material to protect the compound from the action of acids and other natural conditions that may inactivate the compound.

A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A composition described herein can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

To administer a compound described herein by certain routes of administration, it may be necessary to coat the compound with, or co-administer the compound with, a material to prevent its inactivation. For example, the compound may be administered to a subject in an appropriate carrier, for example, liposomes, or a diluent. Acceptable diluents include saline and aqueous buffer solutions. Liposomes include water-in-oil-in-water CGF emulsions as well as conventional liposomes (Strejan et al. (1984) *J. Neuroimmunol.* 7:27).

Carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the antibodies described herein may be administered once or twice weekly by subcutaneous or intramuscular injection or once or twice monthly by subcutaneous or intramuscular injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations described herein include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred per cent, this amount will range from about 0.001 percent to about ninety percent of active ingredient, preferably from about 0.005 percent to about 70 percent, most preferably from about 0.01 percent to about 30 percent.

Formulations described herein which are suitable for vaginal administration also include pessaries, tampons, creams, gels, pastes, foams or spray formulations containing such carriers as are known in the art to be appropriate. Dosage forms for the topical or transdermal administration of compositions described herein include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds described herein are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, the compounds described herein, which may be used in a suitable hydrated form, and/or the pharmaceutical compositions described herein, are formulated into pharmaceutically acceptable dosage forms by conventional methods known to those of skill in the art.

Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds described herein employed in the pharmaceutical composition at levels lower than that required in order to achieve the desired therapeutic effect and gradually increase the dosage until the desired effect is achieved. In general, a suitable daily dose of a composition described herein will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound described herein to be administered alone, it is preferable to administer the compound as a pharmaceutical formulation (composition).

Therapeutic compositions can be administered with medical devices known in the art. For example, in certain embodiments, a therapeutic composition described herein can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the antibodies described herein can be formulated to ensure proper distribution in vivo. For example, the blood-brain barrier (BBB) excludes many highly hydrophilic compounds. To ensure that the therapeutic compounds described herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134), different species of which may comprise the formulations described herein, as well as components of the invented molecules; p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273. In one embodiment, the therapeutic compounds described herein are formulated in liposomes; in certain embodiments, the liposomes include a targeting moiety. In certain embodiments, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

Uses and Methods

In certain embodiments, the antibodies, bispecific molecules, and compositions described herein can be used to treat and/or prevent (e.g., immunize against) Zika virus infection. The ability of the antibodies described herein to bind the fusion loop within domain II of the envelope protein, suggests cross reactivity within the flavivirus family. Therefore, in some embodiments, the antibodies, bispecific molecules and compositions described herein can be used to treat and/or prevent (e.g., immunize against) any member of the flavivirus family.

For use in therapy, the antibodies described herein can be administered to a subject directly (i.e., in vivo), either alone or with other therapies such as an immunostimulatory agent. In all cases, the antibodies, compositions, and immunostimulatory agents and other therapies are administered in an effective amount to exert their desired therapeutic effect. The term "effective amount" refers to that amount necessary or sufficient to realize a desired biologic effect. One of ordinary skill in the art can empirically determine the effective amount of a particular molecule without necessitating undue experimentation.

Preferred routes of administration for vaccines include, for example, injection (e.g., subcutaneous, intravenous, parenteral, intraperitoneal, intrathecal). The injection can be in a bolus or a continuous infusion. Other routes of administration include oral administration.

Antibodies described herein also can be coadministered with adjuvants and other therapeutic agents. It will be appreciated that the term "coadministered" as used herein includes any or all of simultaneous, separate, or sequential administration of the antibodies and conjugates described herein with adjuvants and other agents, including administration as part of a dosing regimen. The antibodies are typically formulated in a carrier alone or in combination with such agents. Examples of such carriers include solutions, solvents, dispersion media, delay agents, emulsions and the like. The use of such media for pharmaceutically active substances is well known in the art. Any other conventional carrier suitable for use with the molecules falls within the scope of the instant disclosure.

In certain embodiments, the antibodies described herein can be utilized for prophylactic applications. In certain embodiments, prophylactic applications involve systems and methods for preventing, inhibiting progression of, and/or delaying the onset of Zika virus infection, and/or any other Zika virus-associated condition in individuals susceptible to and/or displaying symptoms of Zika virus infection. In certain embodiments, prophylactic applications involve systems and methods for preventing, inhibiting progression of, and/or delaying the development of microcephaly in newborn babies of mothers with Zika virus infection.

In some embodiments, the antibodies described herein are utilized for treating or preventing vertical transmission of Zika virus infection in a pregnant subject. In some embodiments, the antibodies described herein are utilized for reducing or reducing the risk of vertical transmission of Zika virus infection in a pregnant subject. In some embodiments, the antibodies are administered to a pregnant subject infected with Zika virus. In some embodiments, the antibodies are administered to a pregnant subject at risk of being infected with Zika virus. In some embodiments, the antibodies described herein are utilized for treating or preventing fetal mortality in a pregnant subject infected with Zika virus or at risk of being infected with Zika virus. In some embodiments, the antibodies described herein are utilized for reducing or reducing the risk of fetal mortality in a pregnant subject infected with Zika virus or at risk of being infected with Zika virus. In some embodiments, the antibodies described herein are utilized to reduce viral load in a pregnant subject, the fetus, and/or the placenta, wherein the pregnant subject is infected with Zika virus. Viral load can be measured as described herein.

Peptides and Compositions Based on Zika Virus Envelope Protein (EP) Epitopes

The antibodies described above are formulated into vaccine compositions. These vaccine compositions may be employed to immunize a subject in order to elicit a highly anti-Zika antibody immune response. Vaccine compositions are also useful to administer to subjects in need thereof to induce a protective immune response. Such vaccine compositions are well known in the art and include, for example, physiologically compatible buffers, preservatives, and saline and the like, as well adjuvants.

"Adjuvants" are agents that nonspecifically increase an immune response to a particular antigen, thus reducing the quantity of antigen necessary in any given vaccine, and/or the frequency of injection necessary in order to generate an adequate immune response to the antigen of interest. Suitable adjuvants for the vaccination of animals include, but are not limited to, Adjuvant 65 (containing peanut oil, mannide monooleate and aluminum monostearate); Freund's complete or incomplete adjuvant; mineral gels, such as aluminum hydroxide, aluminum phosphate and alum; surfactants, such as hexadecylamine, octadecylamine, lysolecithin, dimethyldioctadecylammonium bromide, N,N-dioctadecylN', N'-bis(2-hydroxymethyl) propanediamine, methoxyhexadecylglycerol and pluronic polyols; polyanions, such as pyran, dextran sulfate, poly IC, polyacrylic acid and carbopol; peptides, such as muramyl dipeptide, dimethylglycine and tuftsin; and oil emulsions. The protein or peptides could also be administered following incorporation into liposomes or other microcarriers. Information concerning adjuvants and various aspects of immunoassays are disclosed, e.g., in the series by P. Tijssen, Practice and Theory of Enzyme Immunoassays, 3rd Edition, 1987, Elsevier, N.Y., incorporated by reference herein.

The vaccine composition includes a sufficient amount of the desired immunogen, such as the peptides of the disclosure, to elicit an immune response. The amount administered can range from about 0.0001 g/kg to about 1.0 g/kg, relative to the mass of the animal. Any suitable vertebrate animal is readily employed to obtain polyclonal antiserum. Preferably, the animal is a mammal, and includes, but is not limited to, rodents, such as a mice, rats, rabbits, horses, canines, felines, bovines, ovines, e.g., goats and sheep, primates, e.g., monkeys, great apes and humans, and the like.

The vaccine composition is readily administered by any standard route, including intravenously, intramuscularly, subcutaneously, intraperitoneally, and/or orally. The artisan will appreciate that the vaccine composition is preferably formulated appropriately for each type of recipient animal and route of administration.

Other aspects of the disclosure relate to methods of treating or preventing of Zika virus infection by administering to a subject in need thereof an effective amount of a vaccine according to the disclosure.

The present disclosure is further illustrated by the following examples which should not be construed as further limiting. The contents of Sequence Listing, figures and all references, patents and published patent applications cited throughout this application are expressly incorporated herein by reference.

EXAMPLES

Example 1

Generation of Anti-Zika Virus EP Antibodies

To generate anti-Zika virus envelope protein (EP) antibodies, the FLEP-region located in the ectodomain II (E-DII) of the envelope protein was investigated. To determine which scaffold to employ, the RCSB Protein Data Bank (PDB) was utilized and over 500 antigen-antibody structural complexes were analyzed for interface formation. An anti-TDRD3 (Tudor Domain Containing 3) human antibody was identified as a scaffold with promising potential to interact with the FLEP-region of Zika virus. Therefore, this antibody was chosen for optimization to generate antibodies that target the Zika virus EP. The heavy and light chain variable regions of the anti-TDRD3 are shown in SEQ ID NOs: 4 and 5, respectively.

Antibodies targeting Zika virus EP were designed by computing the epitope-paratope connectivity network, as described in Robinson, L. et al., Cell, Vol. 162: 493-504 (2015). The antibodies were designed to target residues D98, R99 and W101 within the fusion loop. Briefly, the crystal structure of the anti-TDRD3 antibody in complex with the FLEP was used to determine the various inter-residue interatomic contacts across the antigen-antibody interface. The interactions between a CDR residue and its neighboring epitope residues were rendered in a 2D network graph to analyze the connectivity network. Mutations in the CDRs and/or framework regions that contributed to more favorable contacts, as evaluated by the structural analysis and connectivity network, were identified and various amino acid residues which potentially mediate new or improved contacts were analyzed. The variable regions and CDRs generated are shown in Tables 2 and 3 as well as in FIGS. 1A and 1B.

The antibodies were then expressed in Freestyle 293 cells by transient transfection with polyethyleneimine (PEI) and purified by protein A chromatography. The purified antibodies were quantified by IgG ELISA. Briefly, 96-well plates were coated overnight at 4° C. with appropriate antigen. The plates were washed and blocked with 1% blott (Santa Cruz Biotechnologies). Serial dilution of antibodies were added to the plate and incubated for 2 hours at room temperature. Antigen bound IgG was detected using RbaHu IgG HRP conjugated secondary antibody (Jackson ImmunoResearch) followed by TMB substrate (KPL) addition.

Example 2

Binding Affinity of Zika Virus EP Antibodies

To determine whether the antibodies generated were capable of binding to the Zika virus, a sandwich ELISA was used. Specifically, mAbs 3, 6, 7, and 8, as shown in Table 2, were tested. In addition, a fusion loop targeting pan-flavivirus antibody (4G2) and HIV-1 neutralizing antibody (PGT124) were utilized. The heavy and light variable region sequences for 4G2 are set forth in SEQ ID NOs: 12 and 18, respectively. The heavy and light variable region sequences for PGT124 are set forth in SEQ ID NOs: 13 and 19, respectively. The PGT124 antibody targets N-glycan which is present near the fusion loop epitope region of the Zika virus.

Microtiter plates were coated with 0.05 µg of purified mouse 4G2 in carbonate buffer (pH 9.6) overnight at 4° C. and blocked with 10% BSA for 2 hours at room temperature. Thereafter, 5×10$^4$ pfu of Zika virus were added. Specifically, the strains H/PF/2013 (French Polynesia 2013), ILM (Brazil Paraiba 2015), or MR766-NIID (Uganda 1947) were utilized. After 1 hour incubation at room temperature, serial two-fold dilutions of antibodies were added for 1 hour, followed by goat anti-human IgG Fc cross-adsorbed HRP-conjugated anti-human IgG for 45 minutes. Antibody binding was visualized by adding 3,3',5,5'-tetramethylbenzidene substrate and reaction was stopped after 10 minutes with sulphuric acid. In between the different steps, plates were washed twice with PBST (PBS+0.05% Tween). Absorbance was read at 450 nm using a plate reader. The results are shown in FIG. 2 and in Table 1 below.

TABLE 1

| Antibody | Kd µg/mL | | |
|---|---|---|---|
| | Zika strain H/PF/2013 | Zika strain ILM | Zika strain MR766 |
| 4G2 | 10.29 | 6.405 | 0.0422 |
| PGT124 | No/weak binding | 388.2 | No/weak binding |
| mAb 3 | 7.976 | 0.8088 | 0.02479 |
| mAb 6 | 6.542 | 3.847 | 0.02852 |
| mAb 7 | 6.341 | 5.208 | 0.02651 |
| mAb 8 | 22.99 | 19.32 | 0.02984 |

These results indicated the antibodies generated in Example 1 were capable of binding to various Zika virus strains.

Example 3

Neutralization of Zika Virus Envelope Protein Antibodies

To determine whether the anti-Zika virus antibodies could neutralize Zika virus in vitro, purified mAbs were evaluated for their ability to inhibit plaque formation by Zika virus. The plaque neutralization test (PRNT) was performed as previously described (Robinson, L. et al., Cell, Vol. 162: 493-504, 2015). Briefly, the PRNT was performed on BHK-21 cells. Serial two-fold dilution of sera containing mAbs 6 and 8 in RPMI maintenance media (MM) was incubated with 50 pfu of Zika virus (ILM strain or H/PF/2013 strain) in equal volumes for 1 hour before adding to BHK-21. After 1 hour incubation at 37° C., media was aspirated and cells were overlaid with 1% methyl cellulose in MM. After 5 days at 37° C., cells were fixed with 20% formaldehyde and stained with 1% crystal violet. PRNT50 values were determined using a sigmoid dose-response curve fit and reported as reciprocal values.

Figure 3A:
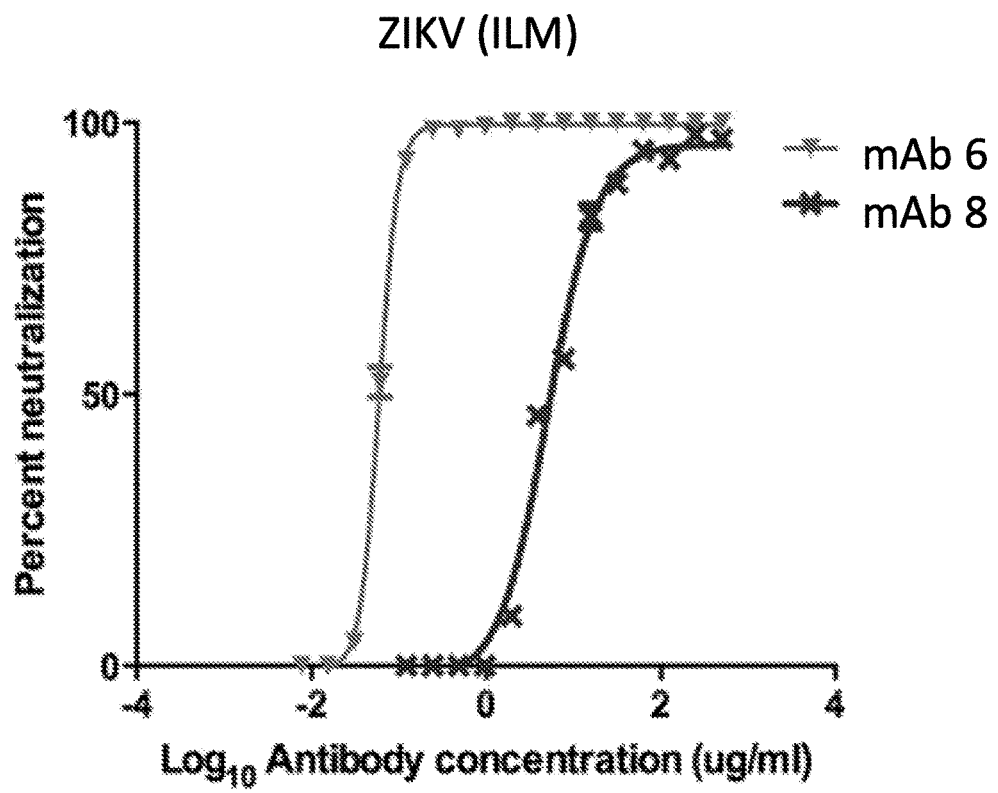
Figure 3B:
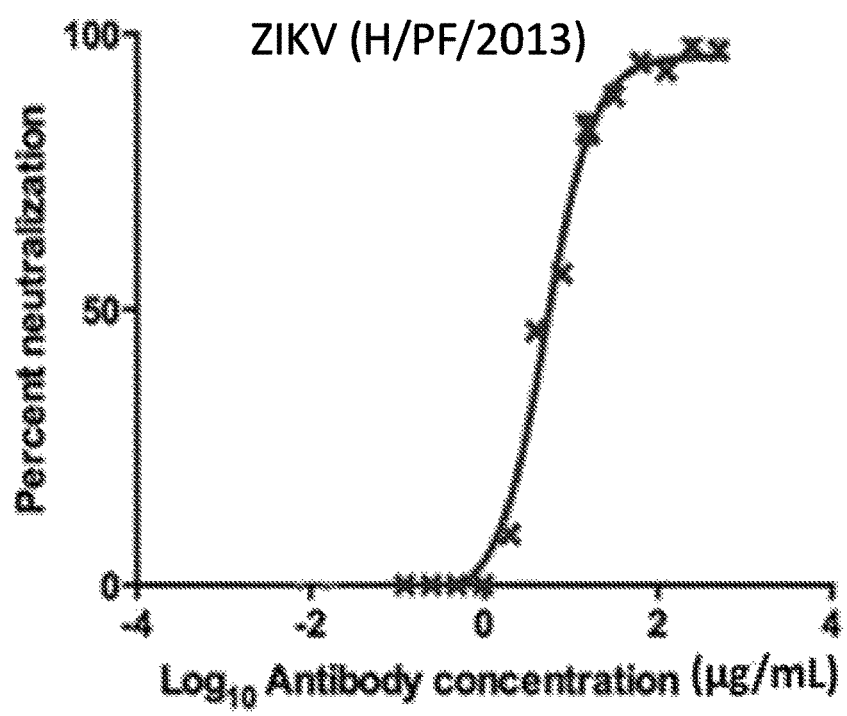

As shown in FIGS. 3A and 3B, mAbs 6 and 8 were capable of neutralizing Zika virus. The PRNT50 of mAb 8 was 5.122 µg/mL whereas the PRNT50 of mAb 6 was 0.0597 µg/mL for the ILM strain. The PRNT50 of mAb 8 was 5.092 µg/mL for the H/PF/2013 strain. These results indicated that antibodies generated against Zika virus could bind and neutralize the virus.

Example 4

In Vivo Prophylactic and Therapeutic Study

To determine whether antibodies capable of binding and neutralizing Zika virus in vitro had protective and therapeutic efficacy in vivo, mAbs 6 and 8 were tested in adult A129 mice (8-11 weeks old). A129 mice were infected intraperitoneally (ip) with H/PF/2013 strain (French Polynesia) at 10$^3$ pfu. To assess protective or prophylactic efficacy of mAbs, mice were injected ip with mAbs (50 µg) one day prior to infection. To assess therapeutic efficacy, mice were injected ip with mAbs (50 µg) one day after infection. Efficacy of mAb was monitored by assessing mortality, weight loss and viremia reduction. In short, mouse blood was collected from facial vein on days 1-8 post-infection to measure serum viremia level by real-time PCR. Weight was monitored daily until the mice succumbed to infection. Mouse survival was monitored until 20 days post-infection.

Figure 4B:
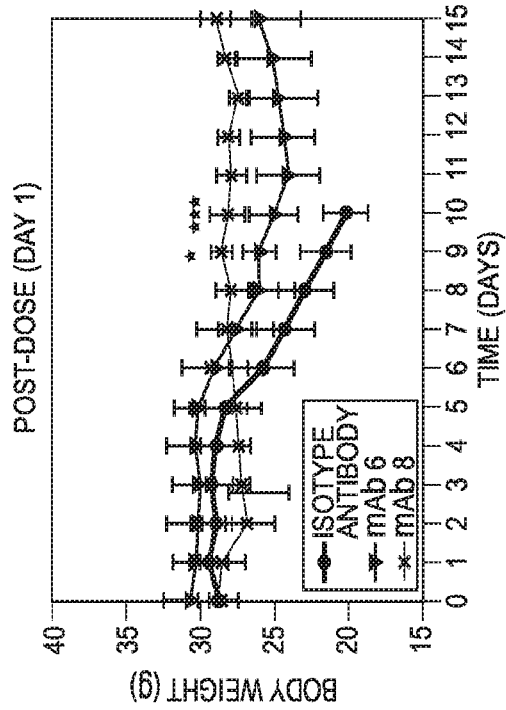
Figure 4D:
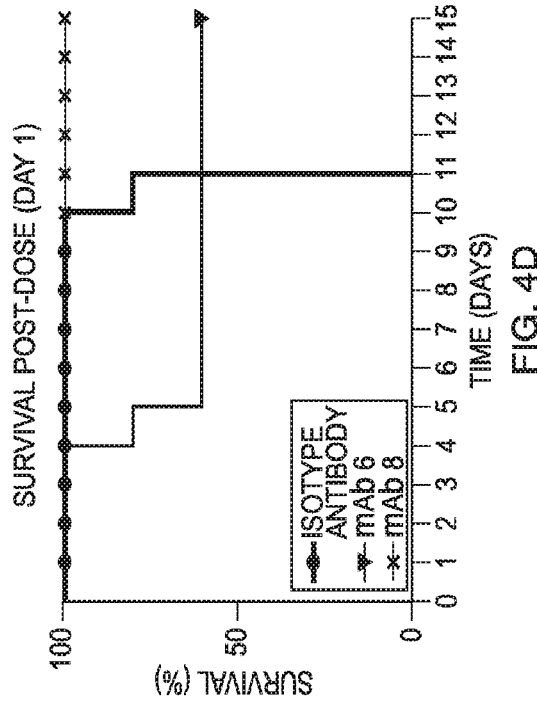
Figure 4A:
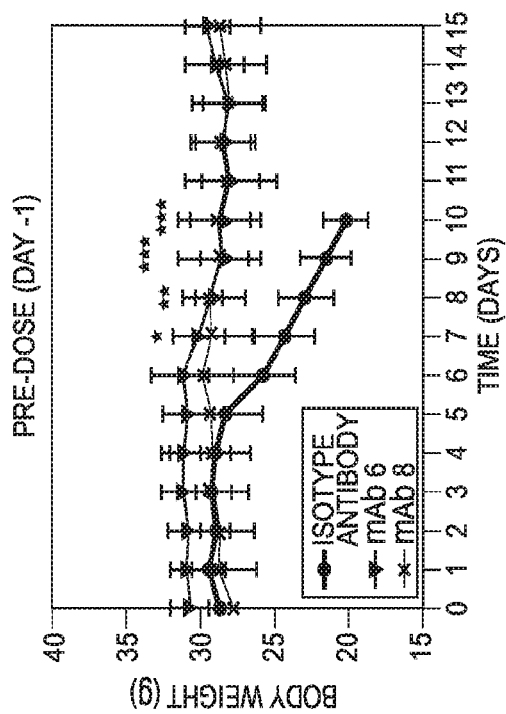
Figure 4C:
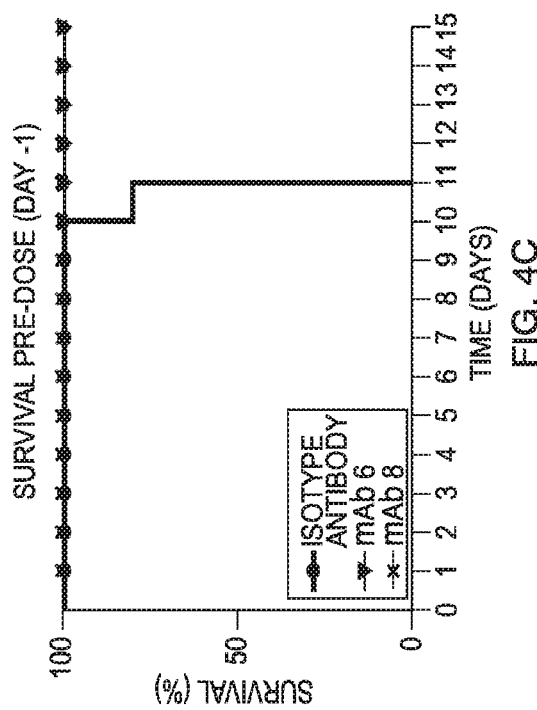

As shown in FIGS. 4C and 4D, virus infection caused 100% mortality by day 10 post-infection. In addition, the mice had symptoms of neuro-related disease (paralysis; data not shown). Treatment with mAb 6 or 8 significantly reduced the mortality rate and the loss in body weight in both prophylactic and treatment models (FIGS. 4A-4D). In addition, FIG. 5 shows mAbs 6 and 8 were able to reduce viremia in mice administered the antibody either prophylactically or therapeutically. Specifically, viral load was reduced by about 2-3 logs and delayed peak viremia.

The results indicated the anti-Zika virus antibodies generated had both prophylactic and therapeutic effects.

Example 5

In Vivo Dosage and Antibody-Dependent Enhancement Study

Figure 6A:
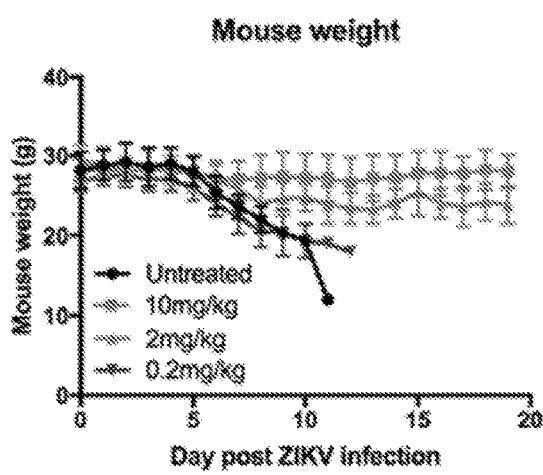
FIG. 6A is a line graph showing the weight, in grams, of mice over time treated with varying doses of mAb 8 administered a day after Zika virus infection (H/PF/2013 strain).
Figure 6B:
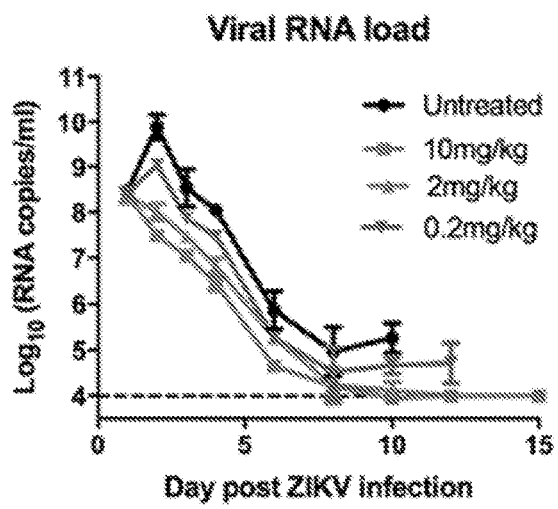
FIG. 6B is a line graph depicting viral load over time in mice treated with varying doses of mAb 8 administered a day after Zika virus infection (H/PF/2013 strain).
Figure 6C:
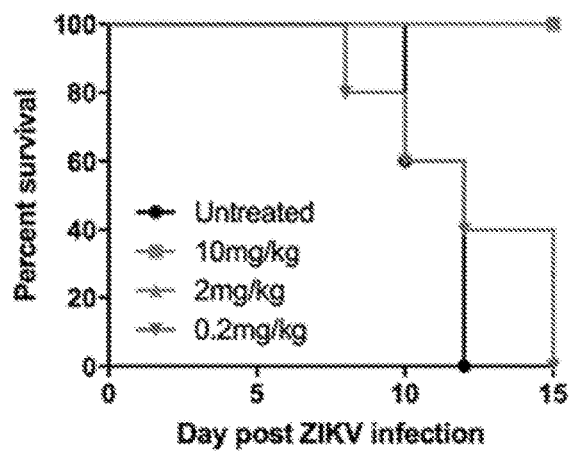
FIG. 6C is a Kaplan-Meier graph showing survival of mice treated with varying doses of mAb 8 administered a day after Zika virus infection (H/PF/2013 strain).

The effect of dosing of anti-Zika virus antibodies on weight loss, viremia and survival was evaluated. A129 mice were administered varying doses of mAb 8 (10 mg/kg, 2 mg/kg or 0.2 mg/kg) a day after infection with Zika virus (strain H/PF/2013). FIGS. 6A-6C show that at 2 mg/kg (~60

μg), mAb 8 reduced viremia and provided complete protection against weight loss and survival. Remarkably, there were no observable differences in viremia or accelerated death even when significantly lower doses (0.2 mg/kg~6 μg) of mAb 8 were administered. These results indicated that mAb 8 has the potential to provide partial protection, even at significantly low concentrations without increasing viremia associated with disease progression.

In addition, antibody-dependent enhancement (ADE) activity of anti-Zika virus mAb 8 was analyzed. ADE is a phenomenon that has been proposed to mediate increased disease severity when infection occurs in a background of preexisting enhancing antibodies. Mechanistically, this occurs when enhancing antibodies bind the mature as well as immature virus particles and mediate virus entry via antibody engagement of Fcγ receptors present on host cells. Several FLE-directed antibodies have been described in literature including 4G2, E53, and the E-dimer epitope (EDE) directed mAbs (Dejnirattisai W, et al., 2015). Several studies have shown that when DENV is opsonized with antibody levels that are phagocytosed by Fcγ receptors, only antibodies that are able to inhibit virus fusion with phagosomal membranes will prevent infection and thus ADE (Chan K R et al., 2011, Wu R et al, 2012). Accordingly, the ability of mAb8's engagement of the Zika virus FLE epitope at the E-dimer interface to reduce its ADE activity by fusion inhibition was tested.

Figure 7B:
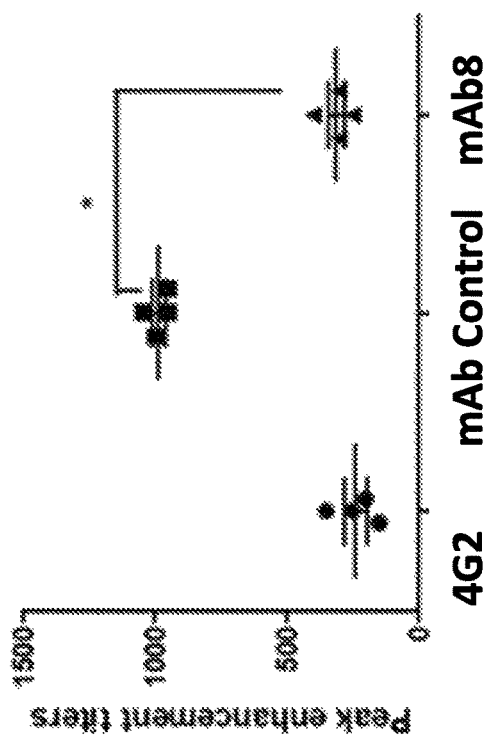
FIG. 7B provides a comparison of peak enhancement titers (viral titer at point of greatest enhancement observed) resulting from the various antibodies as indicated. *<0.05 (non-parametric, two-tailed student's T-test).
Figure 7A:
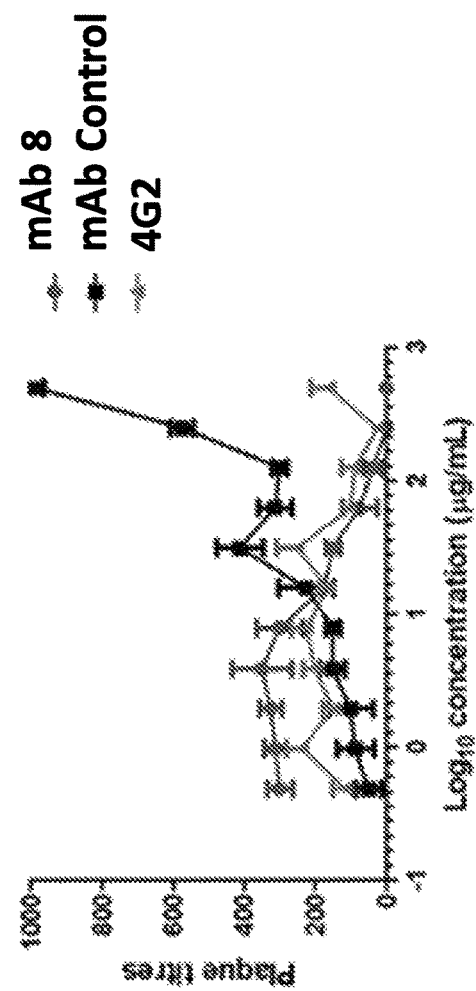
FIG. 7A is a graph depicting antibody-dependent enhancement activity of various antibodies in THP-1 cells infected with Zika virus (H/PF/2013 strain). Plaque titers resulting from opsonization with different concentrations of antibodies is shown.

Specifically, THP1.2S monocyte cells were utilized, which are known to express LILRB1 and are thus highly susceptible to ADE. An early design variant of mAb 8 which showed very weak binding and neutralization of ZIKV H/PF/2013 strain (Kd=50.85 ug/ml; PRNT50>500 ug/ml), was used as a control ("mAb control"). Different concentrations of antibody were incubated with ZIKV (strain H/PF/2013) for 1 hour prior to infecting THP1.2S monocytes. Seventy hours later the virus replication in culture supernatants was measured by plaque assay on BHK21 cells. As shown in FIG. 7A, all mAbs tested showed ADE in THP1.2S cells but mAb13 exhibited high ADE activity without any ZIKV neutralization activity despite high antibody concentrations. In contrast, mAb8 showed ADE of at least 3 fold lower viral titers at peak enhancement comparable with 4G2, which is another fusion loop antibody but which has no neutralization activity against ZIKV (FIG. 7B). These results indicated the anti-Zika virus EP antibodies generated in Example 1 were capable of reducing ADE.

Example 6

Efficacy on Maternal Transfer

Figure 8A:
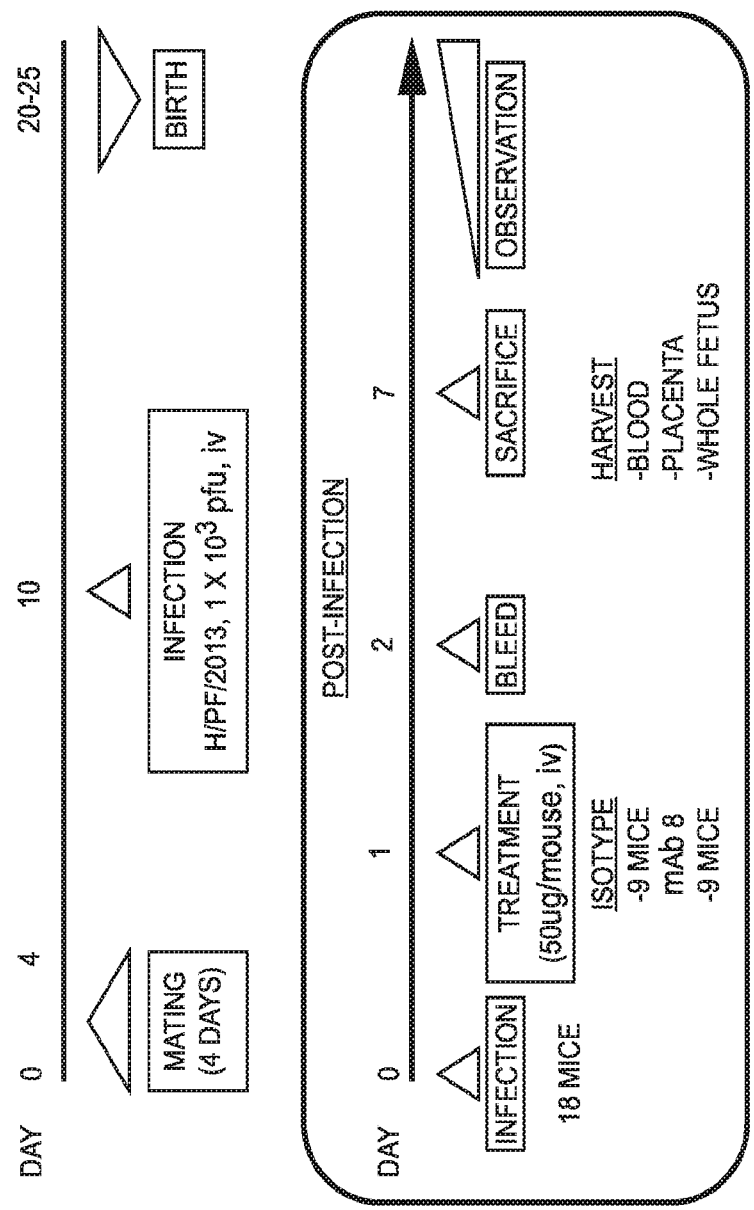

Placental and fetal infection, along with fetal mortality, has been observed in pregnant A129 mice infected with ZIKV. Accordingly, the potential of mAb 8 to prevent vertical infection and fetal mortality in pregnant A129 mice was evaluated. The overall study design is provided in FIG. 8A. Specifically, 18 pregnant A129 mice that were mated to male mice for 4 days (starting on day 0 evening and separated on day 4 morning), were infected with $10^3$ PFU of Zika virus (H/PF/2013 strain of Asian lineage) intravenously on day 10 (corresponding to embryo day 7-10, i.e., E7-E10). The mice were then treated with 50 μg of mAb 8 (n=9) or an isotype control IgG (n=9) for 24 hours (E8-E11) after infection. Mice were sacrificed on day 17 (E14-E17) and viral RNA levels were analyzed on day 12 (blood) and day 17 (blood, placenta and fetal compartments).

Figure 8C:
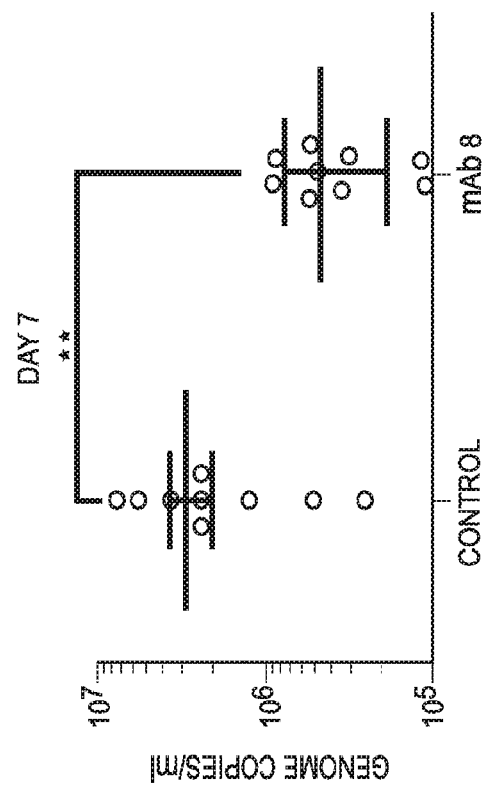
Figure 8B:
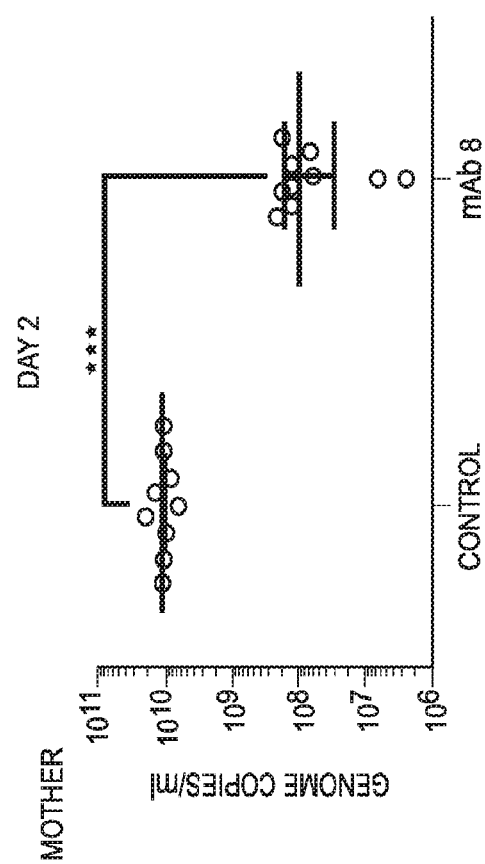
Figure 8E:
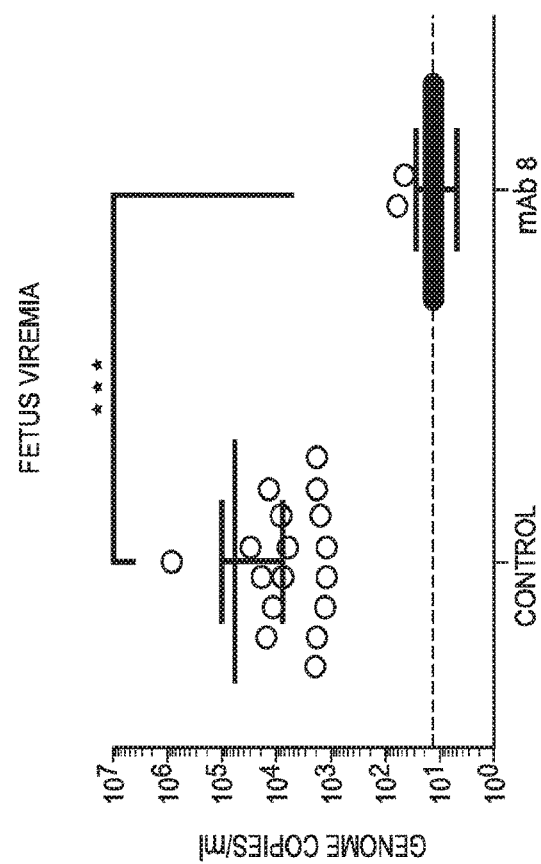
Figure 8D:
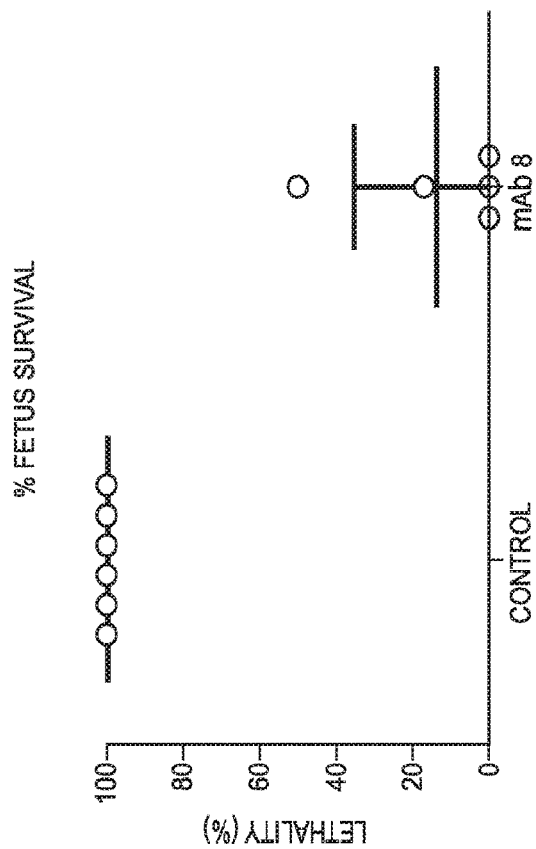
Figure 8F:
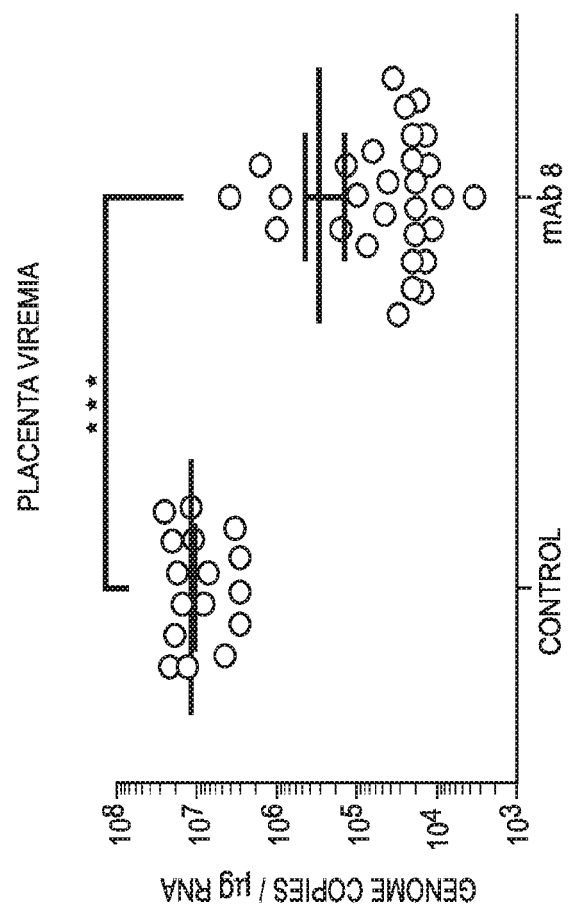

The results of the study are provided in FIGS. 8B-8H. When compared with isotype control IgG treated mice, the mAb 8 treated mice has substantially lower levels of viral RNA in blood on day 12 (p-value <0.0001; two-sided t-test) and day 17 (p-value=0.018; two-sided t-test) (FIGS. 8B and 8C). Significantly, mAb 8 treatment reduced placental (p-value <0.0001; two sided t-test) and fetal (p-value <0.0001; two-sided t-test) infection and provided protection against fetal mortality. In contrast, fetuses harvested from the control group had 100% lethality, with significant viremia in fetal and placental compartments (FIGS. 8D-8F). Fetuses harvested from mice treated with mAb 8 showed signs of normal embryo development without any developmental impairment. In contrast, fetuses from isotype control IgG treated mice were dead before harvesting, revealing a stark morphological difference compared with normal fetuses (data not shown). These results indicated the anti-Zika virus antibodies described herein are capable of preventing vertical infection and fetal mortality in pregnant mice.

Example 7

In Vivo Non-Human Primate Study

Cynomolgus macaques are used to test whether and how effectively an anti-EP mAb can improve survival when administered after high-dose ZIKV infection.

Zika virus (ZIKV) is produced on Vero cells in complete minimal essential medium (cMEM), 2% FBS, and 1% penicillin/streptomycin.

Macaques are randomized into groups on the basis of treatment regimens, plus one receiving only PBS as a positive control for infection. Each subject is infected with 1000 PFU (1 mL each into two sites intramuscularly) of ZIKV in Dulbecco's modified Eagle's medium (DMEM). Half of the groups begin treatment 24 hours post infection and the other half of the groups begin treatment 48 hours post infection. The subjects are treated intravenously with a mAb (25 mg/kg), one of the ZIKV-EP-specific neutralizing antibodies disclosed herein, as a 5 mL slow bolus in the saphenous vein. The subjects are monitored daily and scored for disease progression with an internal scoring protocol. Scoring rates changes in the subject's posture/activity, attitude, activity level, feces/urine output, food/water intake, weight, temperature, respiration, and scored disease manifestations such as a visible rash, hemorrhage, cyanosis, or flushed skin. Tests for weight, temperature, blood, and oropharyngeal, nasal, and rectal swabs are taken at days 1, 4, 7, 14, 21, and 28 post infections for the 24-hour group or at 2, 5, 8, 14, 21, and 28 days post infection for the 48-hour group, before the animals receive the mAb.

Example 8

Human Study

Humans infected with Zika virus are given a single anti-EP antibody disclosed herein. Ideally, the antibodies will be given 24 or 48 hours post infection. Subjects will be monitored for disease manifestations such as visible rash, fevers, or joint pain. In addition, newborns from pregnant women receiving an anti-EP antibody disclosed herein, will be monitored for microcephaly. Viral titers will also be monitored.

EQUIVALENTS

Those skilled in the art will recognize, or be able to ascertain using no more than routine experimentation, many equivalents of the specific embodiments of the disclosure described herein. Such equivalents are intended to be encompassed by the following claims.

TABLE 2

Antibody Pairs by SEQ ID Number

| Antibody | $V_H$ | $V_L$ | $V_H$ CDR CDR1 | CDR2 | CDR3 | $V_L$ CDR CDR1 | CDR2 | CDR3 |
|---|---|---|---|---|---|---|---|---|
| mAb 1 | 4 | 14 | 20 | 26 | 31 | 38 | 44 | 50 |
| mAb 2 | 4 | 15 | 20 | 26 | 31 | 38 | 44 | 50 |
| mAb 3 | 9 | 16 | 22 | 28 | 33 | 39 | 45 | 51 |
| mAb 4 | 4 | 16 | 20 | 26 | 31 | 39 | 45 | 51 |
| mAb 5 | 4 | 17 | 20 | 26 | 31 | 40 | 46 | 50 |
| mAb 6 | 8 | 14 | 21 | 28 | 32 | 38 | 44 | 50 |
| mAb 7 | 7 | 17 | 21 | 27 | 32 | 40 | 46 | 50 |
| mAb 8 | 6 | 15 | 21 | 27 | 32 | 38 | 44 | 50 |
| mAb 9 | 6 | 5 | 21 | 27 | 32 | 37 | 43 | 49 |
| mAb 10 | 7 | 5 | 21 | 27 | 32 | 37 | 43 | 49 |
| mAb 11 | 8 | 5 | 21 | 28 | 32 | 37 | 43 | 49 |
| mAb 12 | 9 | 5 | 22 | 28 | 33 | 37 | 43 | 49 |
| mAb 13 | 10 | 5 | 23 | 28 | 34 | 37 | 43 | 49 |
| mAb 14 | 11 | 5 | 21 | 28 | 34 | 37 | 43 | 49 |
| mAb 15 | 6 | 14 | 21 | 27 | 32 | 38 | 44 | 50 |
| mAb 16 | 6 | 16 | 21 | 27 | 32 | 39 | 45 | 51 |
| mAb 17 | 6 | 17 | 21 | 27 | 32 | 40 | 46 | 50 |
| mAb 18 | 7 | 14 | 21 | 27 | 32 | 38 | 44 | 50 |
| mAb 19 | 7 | 15 | 21 | 27 | 32 | 38 | 44 | 50 |
| mAb 20 | 7 | 16 | 21 | 27 | 32 | 39 | 45 | 51 |
| mAb 21 | 8 | 15 | 21 | 28 | 32 | 38 | 44 | 50 |
| mAb 22 | 8 | 16 | 21 | 28 | 32 | 39 | 45 | 51 |
| mAb 23 | 8 | 17 | 21 | 28 | 32 | 40 | 46 | 50 |
| mAb 24 | 9 | 14 | 22 | 28 | 33 | 38 | 44 | 50 |
| mAb 25 | 9 | 15 | 22 | 28 | 33 | 38 | 44 | 50 |
| mAb 26 | 9 | 17 | 22 | 28 | 33 | 40 | 46 | 50 |
| mAb 27 | 10 | 14 | 23 | 28 | 34 | 38 | 44 | 50 |
| mAb 28 | 10 | 15 | 23 | 28 | 34 | 38 | 44 | 50 |
| mAb 29 | 10 | 16 | 23 | 28 | 34 | 39 | 45 | 51 |
| mAb 30 | 10 | 17 | 23 | 28 | 34 | 40 | 46 | 50 |
| mAb 31 | 11 | 14 | 21 | 28 | 34 | 38 | 44 | 50 |
| mAb 32 | 11 | 15 | 21 | 28 | 34 | 38 | 44 | 50 |
| mAb 33 | 11 | 16 | 21 | 28 | 34 | 39 | 45 | 51 |
| mAb 34 | 11 | 17 | 21 | 28 | 34 | 40 | 46 | 50 |

TABLE 3

Summary Sequence Table

| SEQ ID NO | Description | Sequence |
|---|---|---|
| 1 | Human IgG1 Heavy Chain | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 2 | Human IgG2 Light Chain (kappa) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 3 | Zika virus fusion protein loop (residues 98-109 of E-DII) | DRGWGNGCGLFG |
| 4 | anti-TDRD3 $V_H$ Wild Type | EVQLVESGGGLVQPGGSLRLSCAAS<u>GFNLSSS</u>MHWVRQAPGKGLEWVASI<u>SSSYGS</u>TYYADSVKGRFTISADTSKNTAYLQMNSLRAEDTAVYYCAR<u>TVRGSKKPYFSGWAMDY</u>WGQGTLVTVSS |
| 5 | anti-TDRD3 $V_L$ Wild Type | DIQMTQSPSSLSASVGDRVTITC<u>RASQSVSSAVA</u>WYQQKPGKAPKLLIY<u>SASSLYS</u>GVPSRFSGSRSGTDFTLTISSLQPEDFATYYC<u>QQHGPFYW-L</u>FTFGQGTKVEIK |

TABLE 3-continued

Summary Sequence Table

| SEQ ID NO | Description | Sequence |
|---|---|---|
| 6 | V_H.1 | EVQLLESGGGLVQPGGSLRLSCAASGFSFSTYSMHWVRQAPG KGLEWVSAISGEGDSAYYADSVKGRFTISRDNSKNTLYLQMN KVRAEDTAVYYCV----GGYSNFYYYYTMDAWGQGTMVTVSS (V5L, N28S, L29F, S31T, S32Y, Y33S, A49S, S50A, S52(A)G, S53E, Y54G, G55D, T57A, A71R, T73N, A78L, S82(B)K, L82(C)V, A93V, S99G, K100Y, K100(A)S, P100(B)N, Y100(C)F, F100(D)Y, S100(E)Y, G100(F)Y, W100(G)Y, A100(H)T, Y102(A), L108M) |
| 7 | V_H.2 | EVQLLESGGGLVQPGGSLRLSCAASGFSFSTYSMHWVRQAPG KGLEWVSAISGEGDSAYYADSVKGRFEISRDNSKNTLYLQMN KVRAEDTAVYYCV----GGYSNFYYYYTMDAWGQGTMVTVSS (V5L, N28S, L29F, S31T, S32Y, Y33S, A49S, S50A, S52(A)G, S53E, Y54G, G55D, T57A, T68E, A71R, T73N, A78L, S82(B)K, L82(C)V, A93V, S99G, K100Y, K100(A)S, P100(B)N, Y100(C)F, F100(D)Y, SI00(E)Y, G100(F)Y, W100(G)Y, A100(H)T, Y102A, L108M) |
| 8 | V_H.3 | EVQLLESGGGLVQPGGSLRLSCSASGFSFSTYSMHWVRQAPG KGLEYVSAITGEGDSAFYADSVKGRFTISRDNSKNTLYLFEMNS LRPEDTAVYYCV----GGYSNFYYYYTMDAWGQGTSVTVSS (A23S, N28S, L29F, S31T, S32Y, Y33S, W47Y, A49S, S50A, S52T, S52(A)G, S53E, Y54G, G55D, T57A, Y58F, A71R, T73N, A78L, L80F, Q81E, A84P, A93V, S99G, K100Y, K100(A)S, P100(B)N, Y100(C)F, F100(D)Y, S100(E)Y, G100(F)Y, W100(G)Y, A100(H)T, Y102A, L108S) |
| 9 | V_H.4 | EVQLLESGGGLVQPGGSLRLSCSASGFTFSTYSMHWVRQAPG KGLEYVSAITGEGDSAFYADSVKGRFTISRDNSKNTLYFEMNS LRPEDTAVYYCV----GGYSNFYYYYTMDVWGQGTTVTVSS (A23S, N28T, L29F, S31T, S32Y, Y33S, W47Y, A49S, S50A, S52T, S52(A)G, S53E, Y54G, G55D, T57A, Y58F, A71R, T73N, A78L, L80F, Q81E, A84P, A93V, S99G, K100Y, K100(A)S, P100(B)N, Y100(C)F, F100(D)Y, S100(E)Y, G100(F)Y, W100(G)Y, A100(H)T, Y102V, L108T) |
| 10 | V_H.5 | QVQLVESGGGLVQPGGSLRLSCSASGFFSTYSMHWVKQAPGK GLEYVSAITGEGDSAFYADSVKGRFTISRDNSKNTLYFEMNSL RPEDTAVYYCV----GGYTNFYYYYTMDAWGQGTSVTVSS (EQ1, A23S, L29F, S31T, S32Y, Y33S, R38K, W47Y, A49S, S50A, S52T, S52(A)G, S53E, Y54G, G55D, T57A, Y58F, A71R, T73N, A78L, L80F, Q81E, A84P, A93V, S99G, K100Y, K100(A)T, P100(B)N, Y100(C)F, F100(D)Y, S100(E)Y, G100(F)Y, W100(G)Y, A100(H)T, Y102A, L108S) |
| 11 | V_H.6 | QVQLVESGGGLVQPGGSLRLSCSASGFSFSTYSMHWVKQAPG KGLEYVSAITGEGDSAFYADSVKGRFTISRDNSKNTLYFEMNS LRPEDTAVYYCV----GGYTNFYYYYTMDAWGQGTSVTVSS (EQ1, A23S, N28S, L29F, S31T, S32Y, Y33S, R38K, W47Y, A49S, S50A, S52T, S52(A)G, S53E, Y54G, G55D, T57A, Y58F, A71R, T73N, A78L, L80F, Q81E, A84P, A93V, S99G, K100Y, K100(A)T, P100(B)N, Y100(C)F, F100(D)Y, S100(E)Y, G100(F)Y, W100(G)Y, A100(H)T, Y102A, L108S) |
| 12 | v_H of fusion loop targeting pan-flavivirus antibody 4g2 | EVQLQQSGPELVKPGTSVKISCKTSGYTFTEYTIHWVKQSHGK SLAWIGGIDPNSGGTNYSPNFKGKATLTVDKSSSTAYMDLRSL SSEDSAVYFCARIYHYDGYFDVWGAGTAVTVSS |
| 13 | V_H of anti-HIV neutralizing antibody PGT124 | QVQLQESGPGLVRPSETLSVTCIVSGGSISNYYWTWIRQSPGKG LEWIGYISDRETTTYNPSLNSRAVISRDTSKNQLSLQLRSVTTA DTAIYFCATARRGQRIYGVVSFGEFFYYYYMDVWG KGTAVTVSS |

TABLE 3-continued

Summary Sequence Table

| SEQ ID NO | Description | Sequence |
|---|---|---|
| 14 | V$_L$.1 | EIVLTQSPASESLSPGERATLSCRATQSISTFLAWYQHKPGQA PRLLIYDASTRASGVPARFSGSRSGTDFTLTISSLEPEDFAVYYC QQR-YNWPPYSFGQGTKVEIK<br>(D1E, Q3V, M4L, S9A, A13L, V15P, D17E, V19A, I21L, Y22S, S26T, V29I, S31T, A32F, V33L, Q38H, K42Q, K45R, S50D, S53T, L54R, Y55A, S60A, Q79E, T85V, H91R, F94Y, Y95N, L95(b)P, F96Y, T97S) |
| 15 | V$_L$.2 | DIVMTQSPASLSLSPGERATLSCRATQSISTFLAWYQQKPGQ APRLLIYDASTRASGIPARFSGSRSGTDFTLTITRLEPEDFAVYY CQQR-YNWPPYSFGQGTKLEIK<br>(Q3V, S9A, A13L, V15P, D17E, V19A, I21L, Y22S, S26T, V29I, S31T, A32F, V33L, K42Q, K45R, S50D, S53T, L54R, Y55A, V58I, S60A, S76T, S77R, Q79E, T85V, H91R, F94Y, Y95N, L95(b)P, F96Y, T97S, V104L) |
| 16 | V$_L$.3 | EIVLTQSPATSELSPGERATLSCRAQSISTFLAWYQHKPGQA PRLLIYDASTRATGVPARFSGSRSGTDFTLTISTLEPEDFAVYY CQQR-YNWPPYTFGQGTKVEIK<br>(D1E, Q3V, M4L, S9A, S10T, A13L, V15P, D17E, V19A, I21L, Y22S, V29I, S31T, A32F, V33L, Q38H, K42Q, K45R, S50D, S53T, L54R, Y55A, S56T, S60A, S77T, Q79E, T85V, H91R, F94Y, Y95N, L95(b)P, F96Y) |
| 17 | V$_L$.4 | DIVMTQSPASLSLSPGERATLSCRATQSIVTFLAWYQQKPGQ APRLLIYDASTRASGIPARFSGSRSGTDFTLTITRLEPEDFAVYY CQQR-YNWPPYSFGQGTKLEIK<br>(Q3V, S9A, A13L, V15P, D17E, V19A, I21L, Y22S, S26T, V29I, S30V, S31T, A32F, V33L, K42Q, K45R, S50D, S53T, L54N, Y55A, V58I, S60A, S76T, S77R, Q79E, T85V, H91R, F94Y, Y95N, L93(b)P, F96Y, T97S, V104L) |
| 18 | V$_L$ of fusion loop targeting p TABLE 3-continued Summary Sequence Table

| SEQ ID NO | Description | Sequence |
|---|---|---|
| 31 | anti-TDRD3 $V_H$ CDR3 | TVRGSKKPYFSGWAMDY |
| 32 | $V_H$.1 CDR3 | ----GYSNFYYYYTMDA |
| 33 | $V_H$.4 CDR3 | ----GYSNFYYYYTMDV |
| 34 | $V_H$.5 CDR3 | ----GYTNFYYYYTMDA |
| 35 | 4g2 $V_H$ CDR3 | IYHYDGYFDV |
| 36 | PGT124 $V_H$ CDR3 | ARRGQRIYGVVSFGEFFYYYYMDV |
| 37 | anti-TDRD3 $V_L$ CDR1 | RASQSVSSAVA |
| 38 | $V_L$.1 CDR1 | RATQSISTFLA |
| 39 | $V_L$.3 CDR1 | RASQSISTFLA |
| 40 | $V_L$.4 CDR1 | RATQSIVTFLA |
| 41 | 4g2 $V_L$ CDR1 | KASQDINSYLT |
| 42 | PGT124 $V_L$ CDR1 | GRQALGSRAVQ |
| 43 | anti-TDRD3 $V_L$ CDR2 | SASSLYS |
| 44 | $V_L$.1 CDR2 | DASTRAS |
| 45 | $V_L$.3 CDR2 | DASTRAT |
| 46 | $V_L$.4 CDR2 | DASTNAS |
| 47 | 4g2 $V_L$ CDR2 | RANRLID |
| 48 | PGT124 $V_L$ CDR2 | NNQDRPS |
| 49 | anti-TDRD3 $V_L$ CDR3 | QQHGPFYWLFT |
| 50 | $V_L$.1 CDR3 | QQR--YNWPPYS |
| 51 | $V_L$.3 CDR3 | QQR--YNWPPYT |
| 52 | 4g2 $V_L$ CDR3 | LQYDEFPPT |
| 53 | PGT124 $V_L$ CDR3 | HMWDSRSGFSWS |
| 54 | $V_H$ CDR1 | GFX$_1$FSTY |
| 55 | $V_H$ CDR2 | X$_2$GEGDS |
| 56 | $V_H$ CDR3 | GYX$_3$NFYYYYTMDX$_4$ |
| 57 | $V_L$ CDR1 | RAX$_5$QSIX$_6$TFLA |
| 58 | $V_L$ CDR2 | DASTX7AX$_8$ |
| 59 | $V_L$ CDR3 | QQRYNWPPYX$_9$ |

The invention claimed is:

1. An isolated monoclonal antibody, or antigen binding portion thereof, which binds to Zika virus envelope protein and comprises heavy and light chain variable regions, wherein the heavy and light chain amino acid sequences are selected from the group consisting of:
   (a) SEQ ID NOs: 6 and 15, respectively;
   (b) SEQ ID NOs: 6 and 5, respectively;
   (c) SEQ ID NOs: 6 and 14, respectively;
   (d) SEQ ID NOs: 6 and 16, respectively; and
   (e) SEQ ID NOs: 6 and 17, respectively.

2. The isolated monoclonal antibody, or antigen binding portion thereof, of claim 1, having neutralizing activity against Zika virus.

3. The isolated monoclonal antibody, or antigen binding portion thereof, of claim 1, wherein the antibody is selected from the group consisting of an IgG1, an IgG2, an IgG3, an IgG4, an IgM, an IgA1, an IgA2, an IgD, and an IgE antibody.

4. The isolated monoclonal antibody, or antigen binding portion thereof, according to claim 3, wherein the antibody is an IgG1 antibody.

5. A pharmaceutical composition comprising an isolated monoclonal antibody, or antigen binding portion thereof, of claim 1, and a pharmaceutically acceptable carrier.

6. An isolated monoclonal antibody, or antigen binding portion thereof, which binds to Zika virus envelope protein and comprises heavy and light chain variable regions comprising the amino acid sequences of SEQ ID NOs: 6 and 15, respectively.

7. The isolated monoclonal antibody, or antigen binding portion thereof, of claim 6, having neutralizing activity against Zika virus.

8. The isolated monoclonal antibody, or antigen binding portion thereof, of claim 6, wherein the antibody is selected from the group consisting of an IgG1, an IgG2, an IgG3, an IgG4, an IgM, an IgA1, an IgA2, an IgD, and an IgE antibody.

9. The isolated monoclonal antibody, or antigen binding portion thereof, according to claim 7, wherein the antibody is an IgG1 antibody.

10. A pharmaceutical composition comprising an isolated monoclonal antibody or antigen binding portion thereof, of claim 6, and a pharmaceutically acceptable carrier.

11. An isolated monoclonal antibody, or antigen binding portion thereof, which binds to Zika virus envelope protein and comprises heavy and light chain variable regions comprising the amino acid sequences of SEQ ID NOs: 6 and 5, respectively.

12. The isolated monoclonal antibody, or antigen binding portion thereof, of claim 11, having neutralizing activity against Zika virus.

13. The isolated monoclonal antibody, or antigen binding portion thereof, of claim 11, wherein the antibody is selected from the group consisting of an IgG1, an IgG2, an IgG3, an IgG4, an IgM, an IgA1, an IgA2, an IgD, and an IgE antibody.

14. The isolated monoclonal antibody, or antigen binding portion thereof, according to claim 13, wherein the antibody is an IgG1 antibody.

15. A pharmaceutical composition comprising an isolated monoclonal antibody or antigen binding portion thereof, of claim 11, and a pharmaceutically acceptable carrier.

16. An isolated monoclonal antibody, or antigen binding portion thereof, which binds to Zika virus envelope protein and comprises heavy and light chain variable regions comprising the amino acid sequences of SEQ ID NOs: 6 and 14, respectively.

17. The isolated monoclonal antibody, or antigen binding portion thereof, of claim 16, having neutralizing activity against Zika virus.

18. The isolated monoclonal antibody, or antigen binding portion thereof, of claim 16, wherein the antibody is selected from the group consisting of an IgG1, an IgG2, an IgG3, an IgG4, an IgM, an IgA1, an IgA2, an IgD, and an IgE antibody.

19. The isolated monoclonal antibody, or antigen binding portion thereof, according to claim P, wherein the antibody is an IgG1 antibody.

20. A pharmaceutical composition comprising an isolated monoclonal antibody or antigen binding portion thereof, of claim 16, and a pharmaceutically acceptable carrier.

21. An isolated monoclonal antibody, or antigen binding portion thereof, which binds to Zika virus envelope protein and comprises heavy and light chain variable regions comprising the amino acid sequences of SEQ ID NOs: 6 and 16, respectively.

22. The isolated monoclonal antibody, or antigen binding portion thereof, of claim 21, having neutralizing activity against Zika virus.

23. The isolated monoclonal antibody, or antigen binding portion thereof, of claim 21, wherein the antibody is selected from the group consisting of an IgG1, an IgG2, an IgG3, an IgG4, an IgM, an IgA1, an IgA2, an IgD, and an IgE antibody.

24. The isolated monoclonal antibody, or antigen binding portion thereof, according to claim 23, wherein the antibody is an IgG1 antibody.

25. A pharmaceutical composition comprising an isolated monoclonal antibody or antigen binding portion thereof, of claim 21, and a pharmaceutically acceptable carrier.

26. An isolated monoclonal antibody, or antigen binding portion thereof, which binds to Zika virus envelope protein and comprises heavy and light chain variable regions comprising the amino acid sequences of SEQ ID NOs: 6 and 17, respectively.

27. The isolated monoclonal antibody, or antigen binding portion thereof, of claim 26, having neutralizing activity against Zika virus.

28. The isolated monoclonal antibody, or antigen binding portion thereof, of claim 26, wherein the antibody is selected from the group consisting of an IgG1, an IgG2, an IgG3, an IgG4, an IgM, an IgA1, an IgA2, an IgD, and an IgE antibody.

29. The isolated monoclonal antibody, or antigen binding portion thereof, according to claim 28, wherein the antibody is an IgG1 antibody.

30. A pharmaceutical composition comprising an isolated monoclonal antibody or antigen binding portion thereof, of claim 26, and a pharmaceutically acceptable carrier.

\* \* \* \* \*

SEQUENCE LISTING

<160> NUMBER OF SEQ ID NOS: 59

<210> SEQ ID NO 1
<211> LENGTH: 330
<212> TYPE: PRT
<213> ORGANISM: Homo sapiens
<220> FEATURE:
<221> NAME/KEY: misc_feature
<223> OTHER INFORMATION: Human IgG1 Heavy Chain

<400> SEQUENCE: 1

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 2
<211> LENGTH: 107

```
<212> TYPE: PRT
<213> ORGANISM: Homo sapiens
<220> FEATURE:
<221> NAME/KEY: misc_feature
<223> OTHER INFORMATION: Human IgG2 Light Chain (kappa)

<400> SEQUENCE: 2

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 3
<211> LENGTH: 12
<212> TYPE: PRT
<213> ORGANISM: Artificial Sequence
<220> FEATURE:
<223> OTHER INFORMATION: Synthetic: Zika virus fusion protein loop
      (residues 98-109 of E-DII)

<400> SEQUENCE: 3

Asp Arg Gly Trp Gly Asn Gly Cys Gly Leu Phe Gly
1               5                   10

<210> SEQ ID NO 4
<211> LENGTH: 126
<212> TYPE: PRT
<213> ORGANISM: Artificial Sequence
<220> FEATURE:
<223> OTHER INFORMATION: Synthetic: anti-TDRD3 VH Wild Type

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Leu Ser Ser Ser
            20                  25                  30

Tyr Met His Trp Val Arg Gln Ala Pro Gly Lys Gly Leu Glu Trp Val
        35                  40                  45

Ala Ser Ile Ser Ser Ser Tyr Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Thr Val Arg Gly Ser Lys Pro Tyr Phe Ser Gly Trp Ala
            100                 105                 110

Met Asp Tyr Trp Gly Gln Gly Thr Leu Val Thr Val Ser Ser
            115                 120                 125

<210> SEQ ID NO 5
```

<211> LENGTH: 109
<212> TYPE: PRT
<213> ORGANISM: Artificial Sequence
<220> FEATURE:
<223> OTHER INFORMATION: Synthetic: anti-TDRD3 VL Wild Type

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Gly Pro Phe Tyr Trp
                85                  90                  95

Leu Phe Thr Phe Gly Gln Gly Thr Lys Val Glu Ile Lys
            100                 105

<210> SEQ ID NO 6
<211> LENGTH: 122
<212> TYPE: PRT
<213> ORGANISM: Artificial Sequence
<220> FEATURE:
<223> OTHER INFORMATION: Synthetic: VH .1

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Thr Tyr
            20                  25                  30

Ser Met His Trp Val Arg Gln Ala Pro Gly Lys Gly Leu Glu Trp Val
        35                  40                  45

Ser Ala Ile Ser Gly Glu Gly Asp Ser Ala Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Lys Val Arg Ala Glu Asp Thr Ala Val Tyr Tyr Cys
                85                  90                  95

Val Gly Gly Tyr Ser Asn Phe Tyr Tyr Tyr Thr Met Asp Ala Trp
            100                 105                 110

Gly Gln Gly Thr Met Val Thr Val Ser Ser
        115                 120

<210> SEQ ID NO 7
<211> LENGTH: 122
<212> TYPE: PRT
<213> ORGANISM: Artificial Sequence
<220> FEATURE:
<223> OTHER INFORMATION: Synthetic: VH .2

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Thr Tyr
            20                  25                  30

```
Ser Met His Trp Val Arg Gln Ala Pro Gly Lys Gly Leu Glu Trp Val
            35                  40                  45

Ser Ala Ile Ser Gly Glu Gly Asp Ser Ala Tyr Tyr Ala Asp Ser Val
        50                  55                  60

Lys Gly Arg Phe Glu Ile Ser Arg Asp Asn Ser Lys Asn Thr Leu Tyr
65                  70                  75                  80

Leu Gln Met Asn Lys Val Arg Ala Glu Asp Thr Ala Val Tyr Tyr Cys
                85                  90                  95

Val Gly Gly Tyr Ser Asn Phe Tyr Tyr Tyr Thr Met Asp Ala Trp
            100                 105                 110

Gly Gln Gly Thr Met Val Thr Val Ser Ser
            115                 120

<210> SEQ ID NO 8
<211> LENGTH: 122
<212> TYPE: PRT
<213> ORGANISM: Artificial Sequence
<220> FEATURE:
<223> OTHER INFORMATION: Synthetic: VH .3

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Ser Thr Tyr
            20                  25                  30

Ser Met His Trp Val Arg Gln Ala Pro Gly Lys Gly Leu Glu Tyr Val
            35                  40                  45

Ser Ala Ile Thr Gly Glu Gly Asp Ser Ala Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Phe Glu Met Asn Ser Leu Arg Pro Glu Asp Thr Ala Val Tyr Tyr Cys
                85                  90                  95

Val Gly Gly Tyr Ser Asn Phe Tyr Tyr Tyr Thr Met Asp Ala Trp
            100                 105                 110

Gly Gln Gly Thr Ser Val Thr Val Ser Ser
            115                 120

<210> SEQ ID NO 9
<211> LENGTH: 122
<212> TYPE: PRT
<213> ORGANISM: Artificial Sequence
<220> FEATURE:
<223> OTHER INFORMATION: Synthetic: VH .4

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Thr Tyr
            20                  25                  30

Ser Met His Trp Val Arg Gln Ala Pro Gly Lys Gly Leu Glu Tyr Val
            35                  40                  45

Ser Ala Ile Thr Gly Glu Gly Asp Ser Ala Phe Tyr Ala Asp Ser Val
        50                  55                  60

Lys Gly Arg Phe Thr Ile Ser Arg Asp Asn Ser Lys Asn Thr Leu Tyr
65                  70                  75                  80

Phe Glu Met Asn Ser Leu Arg Pro Glu Asp Thr Ala Val Tyr Tyr Cys
                85                  90                  95
```

-continued

Val Gly Gly Tyr Ser Asn Phe Tyr Tyr Tyr Thr Met Asp Val Trp
            100                 105                 110

Gly Gln Gly Thr Thr Val Thr Val Ser Ser
            115                 120

<210> SEQ ID NO 10
<211> LENGTH: 121
<212> TYPE: PRT
<213> ORGANISM: Artificial Sequence
<220> FEATURE:
<223> OTHER INFORMATION: Synthetic: VH .5

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Phe Ser Thr Tyr Ser
            20                  25                  30

Met His Trp Val Lys Gln Ala Pro Gly Lys Gly Leu Glu Tyr Val Ser
        35                  40                  45

Ala Ile Thr Gly Glu Gly Asp Ser Ala Phe Tyr Ala Asp Ser Val Lys
    50                  55                  60

Gly Arg Phe Thr Ile Ser Arg Asp Asn Ser Lys Asn Thr Leu Tyr Phe
65                  70                  75                  80

Glu Met Asn Ser Leu Arg Pro Glu Asp Thr Ala Val Tyr Tyr Cys Val
                85                  90                  95

Gly Gly Tyr Thr Asn Phe Tyr Tyr Tyr Thr Met Asp Ala Trp Gly
            100                 105                 110

Gln Gly Thr Ser Val Thr Val Ser Ser
        115                 120

<210> SEQ ID NO 11
<211> LENGTH: 122
<212> TYPE: PRT
<213> ORGANISM: Artificial Sequence
<220> FEATURE:
<223> OTHER INFORMATION: Synthetic: VH .6

<400> SEQUENCE: 11

Gln Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Ser Thr Tyr
            20                  25                  30

Ser Met His Trp Val Lys Gln Ala Pro Gly Lys Gly Leu Glu Tyr Val
        35                  40                  45

Ser Ala Ile Thr Gly Glu Gly Asp Ser Ala Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Phe Glu Met Asn Ser Leu Arg Pro Glu Asp Thr Ala Val Tyr Tyr Cys
                85                  90                  95

Val Gly Gly Tyr Thr Asn Phe Tyr Tyr Tyr Thr Met Asp Ala Trp
            100                 105                 110

Gly Gln Gly Thr Ser Val Thr Val Ser Ser
            115                 120

<210> SEQ ID NO 12
<211> LENGTH: 119
<212> TYPE: PRT

```
<213> ORGANISM: Artificial Sequence
<220> FEATURE:
<223> OTHER INFORMATION: Synthetic: VH of fusion loop targeting
      pan-flavivirus antibody 4g2

<400> SEQUENCE: 12

Glu Val Gln Leu Gln Gln Ser Gly Pro Glu Leu Val Lys Pro Gly Thr
1               5                   10                  15

Ser Val Lys Ile Ser Cys Lys Thr Ser Gly Tyr Thr Phe Thr Glu Tyr
                20                  25                  30

Thr Ile His Trp Val Lys Gln Ser His Gly Lys Ser Leu Ala Trp Ile
            35                  40                  45

Gly Gly Ile Asp Pro Asn Ser Gly Gly Thr Asn Tyr Ser Pro Asn Phe
        50                  55                  60

Lys Gly Lys Ala Thr Leu Thr Val Asp Lys Ser Ser Thr Ala Tyr
65                  70                  75                  80

Met Asp Leu Arg Ser Leu Ser Ser Glu Asp Ser Ala Val Tyr Phe Cys
                85                  90                  95

Ala Arg Ile Tyr His Tyr Asp Gly Tyr Phe Asp Val Trp Gly Ala Gly
                100                 105                 110

Thr Ala Val Thr Val Ser Ser
        115

<210> SEQ ID NO 13
<211> LENGTH: 132
<212> TYPE: PRT
<213> ORGANISM: Artificial Sequence
<220> FEATURE:
<223> OTHER INFORMATION: Synthetic: VH of anti-HIV neutralizing
      antibody PGT124

<400> SEQUENCE: 13

Gln Val Gln Leu Gln Glu Ser Gly Pro Gly Leu Val Arg Pro Ser Glu
1               5                   10                  15

Thr Leu Ser Val Thr Cys Ile Val Ser Gly Ser Ile Ser Asn Tyr
                20                  25                  30

Tyr Trp Thr Trp Ile Arg Gln Ser Pro Gly Lys Gly Leu Glu Trp Ile
            35                  40                  45

Gly Tyr Ile Ser Asp Arg Glu Thr Thr Thr Tyr Asn Pro Ser Leu Asn
        50                  55                  60

Ser Arg Ala Val Ile Ser Arg Asp Thr Ser Lys Asn Gln Leu Ser Leu
65                  70                  75                  80

Gln Leu Arg Ser Val Thr Thr Ala Asp Thr Ala Ile Tyr Phe Cys Ala
                85                  90                  95

Thr Ala Arg Arg Gly Gln Arg Ile Tyr Gly Val Val Ser Phe Gly Glu
                100                 105                 110

Phe Phe Tyr Tyr Tyr Tyr Met Asp Val Trp Gly Lys Gly Thr Ala Val
            115                 120                 125

Thr Val Ser Ser
        130

<210> SEQ ID NO 14
<211> LENGTH: 108
<212> TYPE: PRT
<213> ORGANISM: Artificial Sequence
<220> FEATURE:
<223> OTHER INFORMATION: Synthetic: VL .1

<400> SEQUENCE: 14
```

Glu Ile Val Leu Thr Gln Ser Pro Ala Ser Leu Ser Leu Ser Pro Gly
1               5                   10                  15

Glu Arg Ala Thr Leu Ser Cys Arg Ala Thr Gln Ser Ile Ser Thr Phe
                20                  25                  30

Leu Ala Trp Tyr Gln His Lys Pro Gly Gln Ala Pro Arg Leu Leu Ile
            35                  40                  45

Tyr Asp Ala Ser Thr Arg Ala Ser Gly Val Pro Ala Arg Phe Ser Gly
    50                  55                  60

Ser Arg Ser Gly Thr Asp Phe Thr Leu Thr Ile Ser Ser Leu Glu Pro
65                  70                  75                  80

Glu Asp Phe Ala Val Tyr Tyr Cys Gln Gln Arg Tyr Asn Trp Pro Pro
                85                  90                  95

Tyr Ser Phe Gly Gln Gly Thr Lys Val Glu Ile Lys
                100                 105

<210> SEQ ID NO 15
<211> LENGTH: 108
<212> TYPE: PRT
<213> ORGANISM: Artificial Sequence
<220> FEATURE:
<223> OTHER INFORMATION: Synthetic: VL .2

<400> SEQUENCE: 15

Asp Ile Val Met Thr Gln Ser Pro Ala Ser Leu Ser Leu Ser Pro Gly
1               5                   10                  15

Glu Arg Ala Thr Leu Ser Cys Arg Ala Thr Gln Ser Ile Ser Thr Phe
                20                  25                  30

Leu Ala Trp Tyr Gln Gln Lys Pro Gly Gln Ala Pro Arg Leu Leu Ile
            35                  40                  45

Tyr Asp Ala Ser Thr Arg Ala Ser Gly Ile Pro Ala Arg Phe Ser Gly
    50                  55                  60

Ser Arg Ser Gly Thr Asp Phe Thr Leu Thr Ile Thr Arg Leu Glu Pro
65                  70                  75                  80

Glu Asp Phe Ala Val Tyr Tyr Cys Gln Gln Arg Tyr Asn Trp Pro Pro
                85                  90                  95

Tyr Ser Phe Gly Gln Gly Thr Lys Leu Glu Ile Lys
                100                 105

<210> SEQ ID NO 16
<211> LENGTH: 108
<212> TYPE: PRT
<213> ORGANISM: Artificial Sequence
<220> FEATURE:
<223> OTHER INFORMATION: Synthetic: VL .3

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Thr Phe
                20                  25                  30

Leu Ala Trp Tyr Gln His Lys Pro Gly Gln Ala Pro Arg Leu Leu Ile
            35                  40                  45

Tyr Asp Ala Ser Thr Arg Ala Thr Gly Val Pro Ala Arg Phe Ser Gly
    50                  55                  60

Ser Arg Ser Gly Thr Asp Phe Thr Leu Thr Ile Ser Thr Leu Glu Pro
65                  70                  75                  80

Glu Asp Phe Ala Val Tyr Tyr Cys Gln Gln Arg Tyr Asn Trp Pro Pro
                85                  90                  95

```
Tyr Thr Phe Gly Gln Gly Thr Lys Val Glu Ile Lys
            100                 105

<210> SEQ ID NO 17
<211> LENGTH: 108
<212> TYPE: PRT
<213> ORGANISM: Artificial Sequence
<220> FEATURE:
<223> OTHER INFORMATION: Synthetic: VL .4

<400> SEQUENCE: 17

Asp Ile Val Met Thr Gln Ser Pro Ala Ser Leu Ser Leu Ser Pro Gly
1               5                   10                  15

Glu Arg Ala Thr Leu Ser Cys Arg Ala Thr Gln Ser Ile Val Thr Phe
            20                  25                  30

Leu Ala Trp Tyr Gln Gln Lys Pro Gly Gln Ala Pro Arg Leu Leu Ile
        35                  40                  45

Tyr Asp Ala Ser Thr Asn Ala Ser Gly Ile Pro Ala Arg Phe Ser Gly
    50                  55                  60

Ser Arg Ser Gly Thr Asp Phe Thr Leu Thr Ile Thr Arg Leu Glu Pro
65                  70                  75                  80

Glu Asp Phe Ala Val Tyr Tyr Cys Gln Gln Arg Tyr Asn Trp Pro Pro
                85                  90                  95

Tyr Ser Phe Gly Gln Gly Thr Lys Leu Glu Ile Lys
            100                 105

<210> SEQ ID NO 18
<211> LENGTH: 108
<212> TYPE: PRT
<213> ORGANISM: Artificial Sequence
<220> FEATURE:
<223> OTHER INFORMATION: Synthetic: VL  of fusion loop targeting
      pan-flavivirus antibody 4g2

<400> SEQUENCE: 18

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Thr Trp Phe Gln Gln Lys Pro Gly Lys Ser Pro Lys Thr Leu Ile
        35                  40                  45

Tyr Arg Ala Asn Arg Leu Ile Asp Gly Val Pro Ser Arg Phe Ser Gly
    50                  55                  60

Ser Gly Ser Gly Gln Asp Tyr Ser Leu Thr Ile Ser Ser Leu Asp Tyr
65                  70                  75                  80

Glu Asp Met Gly Ile Tyr Tyr Cys Leu Gln Tyr Asp Glu Phe Pro Pro
                85                  90                  95

Thr Phe Gly Gly Gly Thr Lys Leu Glu Ile Lys Arg
            100                 105

<210> SEQ ID NO 19
<211> LENGTH: 111
<212> TYPE: PRT
<213> ORGANISM: Artificial Sequence
<220> FEATURE:
<223> OTHER INFORMATION: Synthetic: VL  of anti-HIV neutralizing
      antibody PGT124

<400> SEQUENCE: 19

Ser Tyr Val Ser Pro Leu Ser Val Ala Leu Gly Glu Thr Ala Arg Ile
```

```
                1               5                  10                  15
Ser Cys Gly Arg Gln Ala Leu Gly Ser Arg Ala Val Gln Trp Tyr Gln
                    20                  25                  30

His Lys Pro Gly Gln Ala Pro Ile Leu Leu Ile Tyr Asn Asn Gln Asp
        35                  40                  45

Arg Pro Ser Gly Ile Pro Glu Arg Phe Ser Gly Thr Pro Asp Ile Asn
        50                  55                  60

Phe Gly Thr Thr Ala Thr Leu Thr Ile Ser Val Glu Val Gly Asp
 65                 70                  75                  80

Glu Ala Asp Tyr Tyr Cys His Met Trp Asp Ser Arg Ser Gly Phe Ser
                    85                  90                  95

Trp Ser Phe Gly Gly Ala Thr Arg Leu Thr Val Leu Ser Gln Pro
                100                 105                 110

<210> SEQ ID NO 20
<211> LENGTH: 7
<212> TYPE: PRT
<213> ORGANISM: Artificial Sequence
<220> FEATURE:
<223> OTHER INFORMATION: Synthetic: anti-TDRD3 VH CDR1

<400> SEQUENCE: 20

Gly Phe Asn Leu Ser Ser Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic: VH.1 CDR1

<400> SEQUENCE: 21

Gly Phe Ser Phe Ser Thr Tyr
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic: VH.4 CDR1

<400> SEQUENCE: 22

Gly Phe Thr Phe Ser Thr Tyr
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic: VH.5CDR1

<400> SEQUENCE: 23

Gly Phe Phe Ser Thr Tyr
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic: 4g2 VH CDR1
```

<400> SEQUENCE: 24

Gly Tyr Thr Phe Thr Glu Tyr
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic: PGT124 VH CDR1

<400> SEQUENCE: 25

Gly Gly Ser Ile Ser Asn Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic: anti-TDRD3 VH CDR2

<400> SEQUENCE: 26

Ser Ser Ser Tyr Gly Ser
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic: VH.1 CDR2

<400> SEQUENCE: 27

Ser Gly Glu Gly Asp Ser
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic: VH.3 CDR2

<400> SEQUENCE: 28

Thr Gly Glu Gly Asp Ser
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic: 4g2 VH CDR2

<400> SEQUENCE: 29

Asp Pro Asn Ser Gly Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic: PGT124 VH CDR2

```
<400> SEQUENCE: 30

Ser Asp Arg Glu Thr
1               5

<210> SEQ ID NO 31
<211> LENGTH: 17
<212> TYPE: PRT
<213> ORGANISM: Artificial Sequence
<220> FEATURE:
<223> OTHER INFORMATION: Synthetic: anti-TDRD3 VH CDR3

<400> SEQUENCE: 31

Thr Val Arg Gly Ser Lys Lys Pro Tyr Phe Ser Gly Trp Ala Met Asp
1               5                   10                  15

Tyr

<210> SEQ ID NO 32
<211> LENGTH: 13
<212> TYPE: PRT
<213> ORGANISM: Artificial Sequence
<220> FEATURE:
<223> OTHER INFORMATION: Synthetic: VH.1 CDR3

<400> SEQUENCE: 32

Gly Tyr Ser Asn Phe Tyr Tyr Tyr Tyr Thr Met Asp Ala
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic: VH.4 CDR3

<400> SEQUENCE: 33

Gly Tyr Ser Asn Phe Tyr Tyr Tyr Tyr Thr Met Asp Val
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic: VH.5 CDR3

<400> SEQUENCE: 34

Gly Tyr Thr Asn Phe Tyr Tyr Tyr Tyr Thr Met Asp Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic: 4g2 VH CDR3

<400> SEQUENCE: 35

Ile Tyr His Tyr Asp Gly Tyr Phe Asp Val
1               5                   10

<210> SEQ ID NO 36
<211> LENGTH: 24
<212> TYPE: PRT
<213> ORGANISM: Artificial Sequence
<220> FEATURE:
<223> OTHER INFORMATION: Synthetic: PGT124 VH CDR3
```

```
<400> SEQUENCE: 36

Ala Arg Arg Gly Gln Arg Ile Tyr Gly Val Val Ser Phe Gly Glu Phe
1               5                   10                  15

Phe Tyr Tyr Tyr Tyr Met Asp Val
            20

<210> SEQ ID NO 37
<211> LENGTH: 11
<212> TYPE: PRT
<213> ORGANISM: Artificial Sequence
<220> FEATURE:
<223> OTHER INFORMATION: Synthetic: anti-TDRD3 VL CDR1

<400> SEQUENCE: 37

Arg Ala Ser Gln Ser Val Ser Ser Ala Val Ala
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic: VL.1 CDR1

<400> SEQUENCE: 38

Arg Ala Thr Gln Ser Ile Ser Thr Phe Leu Ala
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Synthetic: VL.3 CDR1

<400> SEQUENCE: 39

Arg Ala Ser Gln Ser Ile Ser Thr Phe Leu Ala
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic: VL.4 CDR1

<400> SEQUENCE: 40

Arg Ala Thr Gln Ser Ile Val Thr Phe Leu Ala
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic: 4g2 VL CDR1

<400> SEQUENCE: 41

Lys Ala Ser Gln Asp Ile Asn Ser Tyr Leu Thr
1               5                   10

<210> SEQ ID NO 42
<211> LENGTH: 11
<212> TYPE: PRT
<213> ORGANISM: Artificial Sequence
```

```
<220> FEATURE:
<223> OTHER INFORMATION: Synthetic: PGT124 VL CDR1

<400> SEQUENCE: 42

Gly Arg Gln Ala Leu Gly Ser Arg Ala Val Gln
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Synthetic: anti-TDRD3 VL CDR2

<400> SEQUENCE: 43

Ser Ala Ser Ser Leu Tyr Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic: VL.1 CDR2

<400> SEQUENCE: 44

Asp Ala Ser Thr Arg Ala Ser
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic: VL.3 CDR2

<400> SEQUENCE: 45

Asp Ala Ser Thr Arg Ala Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic: VL.4 CDR2

<400> SEQUENCE: 46

Asp Ala Ser Thr Asn Ala Ser
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic: 4g2 VL CDR2

<400> SEQUENCE: 47

Arg Ala Asn Arg Leu Ile Asp
1               5

<210> SEQ ID NO 48
<211> LENGTH: 7
<212> TYPE: PRT
<213> ORGANISM: Artificial Sequence
<220> FEATURE:
```

```
<223> OTHER INFORMATION: Synthetic: PGT124 VL CDR2

<400> SEQUENCE: 48

Asn Asn Gln Asp Arg Pro Ser
1               5

<210> SEQ ID NO 49
<211> LENGTH: 11
<212> TYPE: PRT
<213> ORGANISM: Artificial Sequence
<220> FEATURE:
<223> OTHER INFORMATION: Synthetic: anti-TDRD3 VL CDR3

<400> SEQUENCE: 49

Gln Gln His Gly Pro Phe Tyr Trp Leu Phe Thr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic: VL.1 CDR3

<400> SEQUENCE: 50

Gln Gln Arg Tyr Asn Trp Pro Pro Tyr Ser
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic: VL.3 CDR3

<400> SEQUENCE: 51

Gln Gln Arg Tyr Asn Trp Pro Pro Tyr Thr
1               5                   10

<210> SEQ ID NO 52
<211> LENGTH: 9
<212> TYPE: PRT
<213> ORGANISM: Artificial Sequence
<220> FEATURE:
<223> OTHER INFORMATION: Synthetic: 4g2 VL CDR3

<400> SEQUENCE: 52

Leu Gln Tyr Asp Glu Phe Pro Pro Thr
1               5

<210> SEQ ID NO 53
<211> LENGTH: 12
<212> TYPE: PRT
<213> ORGANISM: Artificial Sequence
<220> FEATURE:
<223> OTHER INFORMATION: Synthetic: PGT124 VL CDR3

<400> SEQUENCE: 53

His Met Trp Asp Ser Arg Ser Gly Phe Ser Trp Ser
1               5                   10

<210> SEQ ID NO 54
<211> LENGTH: 7
<212> TYPE: PRT
<213> ORGANISM: Artificial Sequence
<220> FEATURE:
<223> OTHER INFORMATION: Synthetic: VH CDR1
```

```
<220> FEATURE:
<221> NAME/KEY: misc_feature
<222> LOCATION: (3)..(3)
<223> OTHER INFORMATION: Xaa may or may not be present, and if present
      is a polar amino acid residue

<400> SEQUENCE: 54

Gly Phe Xaa Phe Ser Thr Tyr
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic: VH CDR2
<220> FEATURE:
<221> NAME/KEY: misc_feature
<222> LOCATION: (1)..(1)
<223> OTHER INFORMATION: Xaa is a polar amino acid residue

<400> SEQUENCE: 55

Xaa Gly Glu Gly Asp Ser
1               5

<210> SEQ ID NO 56
<211> LENGTH: 13
<212> TYPE: PRT
<213> ORGANISM: Artificial Sequence
<220> FEATURE:
<223> OTHER INFORMATION: Synthetic: VH CDR3
<220> FEATURE:
<221> NAME/KEY: misc_feature
<222> LOCATION: (3)..(3)
<223> OTHER INFORMATION: Xaa is a polar amino acid residue
<220> FEATURE:
<221> NAME/KEY: misc_feature
<222> LOCATION: (13)..(13)
<223> OTHER INFORMATION: Xaa is a nonpolar amino acid residue

<400> SEQUENCE: 56

Gly Tyr Xaa Asn Phe Tyr Tyr Tyr Tyr Thr Met Asp Xaa
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic: VL CDR1
<220> FEATURE:
<221> NAME/KEY: misc_feature
<222> LOCATION: (3)..(3)
<223> OTHER INFORMATION: Xaa is a polar amino acid residue
<220> FEATURE:
<221> NAME/KEY: misc_feature
<222> LOCATION: (7)..(7)
<223> OTHER INFORMATION: Xaa is a polar amino acid residue or a
      hydrophobic amino acid residue

<400> SEQUENCE: 57

Arg Ala Xaa Gln Ser Ile Xaa Thr Phe Leu Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Synthetic: VL CDR2
<220> FEATURE:
```

```
<221> NAME/KEY: misc_feature
<222> LOCATION: (5)..(5)
<223> OTHER INFORMATION: Xaa is a polar amino acid residue
<220> FEATURE:
<221> NAME/KEY: misc_feature
<222> LOCATION: (7)..(7)
<223> OTHER INFORMATION: Xaa is a polar amino acid residue

<400> SEQUENCE: 58

Asp Ala Ser Thr Xaa Ala Xaa
1               5

<210> SEQ ID NO 59
<211> LENGTH: 10
<212> TYPE: PRT
<213> ORGANISM: Artificial Sequence
<220> FEATURE:
<223> OTHER INFORMATION: Synthetic: VL CDR3
<220> FEATURE:
<221> NAME/KEY: misc_feature
<222> LOCATION: (10)..(10)
<223> OTHER INFORMATION: Xaa is a polar amino acid residue

<400> SEQUENCE: 59

Gln Gln Arg Tyr Asn Trp Pro Pro Tyr Xaa
1               5                   10
```